US006183997B1

(12) United States Patent
Hogrefe

(10) Patent No.: US 6,183,997 B1
(45) Date of Patent: Feb. 6, 2001

(54) POLYMERASE ENHANCING FACTOR (PEF) EXTRACTS PEF PROTEIN COMPLEXES ISOLATED PEF PROTEINS AND METHODS FOR PURIFYING AND IDENTIFYING SAME

(75) Inventor: Holly Hogrefe, San Diego, CA (US)

(73) Assignee: Stratagene, La Jolla, CA (US)

(*) Notice: Under 35 U.S.C. 154(b), the term of this patent shall be extended for 0 days.

(21) Appl. No.: 08/822,774

(22) Filed: Mar. 21, 1997

(51) Int. Cl.$^7$ .......... C12P 19/34
(52) U.S. Cl. .......... 435/91.2; 536/24.1; 536/23.7
(58) Field of Search .......... 435/91.2; 536/24.1, 536/23.7

(56) References Cited

U.S. PATENT DOCUMENTS

| | | | |
|---|---|---|---|
| 5,407,800 | 4/1995 | Gelfand et al. | 435/6 |
| 5,427,928 | 6/1995 | Slesarev | 435/91.5 |
| 5,436,149 | 7/1995 | Barnes | 435/194 |
| 5,556,772 | 9/1996 | Sorge et al. | 435/91.2 |

FOREIGN PATENT DOCUMENTS 0 745 687 12/1996 (EP) .

OTHER PUBLICATIONS

Sarkar, Gobinda et al., "Formamide can dramatically improve the specificity of PCR" Nucleic Acids Research, vol. 18, No. 24, 1990, p. 7465.

Richter, Oliver–Matthias H. et al., "Cloning and sequencing of the gene for the cytoplasmic inorganic pyrophosphatase . . . " Eur. J. Biochem. 209, 351–355 (1992).

Spitzer, Eric D., et al. "β–Alanine Auxotrphy Associated with dfp, a Locus Affecting DNA . . . " Journal of Bacteriology, vol. 170, No. 2, Feb. 1988, pp. 872–876.

Spitzer, Eric D. et al., "dfp Gene of *Escherichia coli* K–12, a Locus Affecting DNA . . . " Journal of Bacteriology, Dec. 1985, vol. 164, pp. 994–1003.*

Kelman, Zvi et al., "Structural and functional similarities of prokaryotic and eukaryotic DNA polymerase sliding clamps", Nucleic Acids Research, 1995, vol. 23, No. 18, pp. 3613–3620.*

Takamatsu, Satoko et al., "Mismatch DNA recognition protein from an extremely thermophilic bacterium, Thermus thermopilus HB8" Nucleic Acids Research, 1996, vol. 24, No. 4, pp. 640–647.*

Wagner, Robert et al., "Mutation detection using immobilized mismatch binding protein (MutS)" Nucleic Acids Research, 1995, vol. 23, No. 19, pp. 3944–3948.

Tabor, Stanley et al., "DNA sequence analysis with a modified bacteriophase T7 DNS polymerase" Proc. Natl. Acad. Sci. USA, vol. 84, Jul. 1987, p. 4767–4771.

Gottlieb, J. et al., "Interaction of Herpes Simplex Virus Type 1 DNA Polymerase and the UL42 Accessory Protein with a Model Primer Template" Journal of Virology, Aug. 1994, vol. 68, No. 8, pp. 4937–4945.

Tsurumi, Tatsuya et al., "Functional Interation between Epstein–Barr Virus DNA Polymerase Catalytic Subunit . . . " Journal of Virology, Dec. 1993, vol. 67, No. 12, pp. 7648–7653.

Chevet, Eric et al., "Low concentrations of tetramethylammonium chloride increase yield and specificity of PCR" Nucleic Acids Research, 1995, vol. 23, No. 16, pp. 3343–3344.

Hung, Ted et al., "A specificity enhancer for polymerase chain reaction" Nucleic Acids Research, vol. 18, No. 16, p. 4953.

Schwarz, Klaus et al., "Improved yields of long PCR products using gene 32 protein" Nucleic Acids Research, vol. 18, No. 4, p. 1079.

Young, Mark C. et al., "Structure and Function aof the Bacteriophage T4 DNA Polymerase Holoenzyme" Biochemistry, vol. 31, No. 37, Sep. 22, 1992, pp. 8675–8690.

Barnes, Wayne M., "PCR amplification of up to 35–kb DNA with high fidelity and high yield from . . . " Proc. Natl. Acad. Sci. USA. vol. 91, Mar. 1994, pp. 2216–2220.

Oncor Fidelity DNA Sequencing System Product Profile, Aug. 1995.

Randall, Dr. Sandra K. et al., "High–Resolution Sequencing of Double–Stranded DNA with the Fidelity DNA Sequencing System" Oncor Fidelity DNA Sequencing System Application Note.

Mukai, Hiroyuki et al., "Long and Accurate (LA) PCR with Greater Fidelity and Higher Yields Using TaKaRa LA" Oncor TaKaRa LA PCR Kit Application Note.

* cited by examiner

*Primary Examiner*—Scott W. Houtteman
(74) *Attorney, Agent, or Firm*—Finnegan, Henderson, Farabow, Garrett & Dunner, L.L.P.

(57) ABSTRACT

Novel extracts, proteins, and complexes are identified, purified, and analyzed, which improve the polymerization activity of nucleic acid polymerases. Included within the aspects of the invention are methods for identifying compositions with a polymerase enhancing activity, methods for purifying and using these compositions, and specific extracts, proteins, and complexes that function to enhance polymerase activity. Implications for numerous assays and techniques are described. For example, the invention can be used to enhance polymerase activity in a PCR process and to increase the sensitivity of a PCR-based assay.

41 Claims, 32 Drawing Sheets

— 6.2kb 1 2 3 4 5 6 7

ENHANCEMENT OF QUICKCHANGE MUTAGENESIS WITH PEF-CONTAINING HEPARIN SEPHAROSE FRACTIONS

| Polymerase | buffer/ [dNTP, μM each] | PEF (μl) | Amplification Yield | # cfu | % mutant |
|---|---|---|---|---|---|
| nPfu (#38) | nPfu/ 50 | 0 | + | 84 | 95 |
| | | 1 | + | 47 | 87 |
| | | 0.1 | + | 154 | 97 |
| | | 0.01 | ++ | 632 | 95 |
| | | 0.001 | + | 484 | 94 |
| cPfu (#24A) | nPfu/ 50 | 0 | + | 94 | 89 |
| | | 1 | + | 34 | 85 |
| | | 0.1 | + | 173 | 91 |
| | | 0.01 | ++ | 468 | 96 |
| | | 0.001 | + | 230 | 90 |

*FIG. 27*

POLYMERASE ENHANCING FACTOR (PEF) EXTRACTS PEF PROTEIN COMPLEXES ISOLATED PEF PROTEINS AND METHODS FOR PURIFYING AND IDENTIFYING SAME

BACKGROUND OF THE INVENTION

1. Field of the Invention

The invention relates to the fields of nucleic acid polymerases and nucleic acid polymerization reactions.

2. Introduction

The efficiency of a nucleic acid polymerization reaction has implications for numerous assays and techniques. For example, the ability to enhance polymerase activity in a PCR process increases the sensitivity of the PCR-based assay. We have identified, purified, and analyzed novel extracts, proteins, and complexes that improve the polymerization activity of nucleic acid polymerases. Included within the aspects of the present invention are methods for identifying compositions with a polymerase enhancing activity, methods for purifying and using these compositions, and specific extracts, proteins, and complexes that function to enhance polymerase activity.

3. Description of Related Art

Manipulating nucleic acids with polymerization reactions is a fundamental component of biotechnology-related research. These reactions permit researchers to replicate DNA or RNA in vitro, which in turn allows cloning or amplification of specific nucleic acids or groups of nucleic acids. Numerous other examples exist detailing the critical nature of a nucleic acid polymerization reaction or a nucleic acid polymerization enzyme in a particular technique, including sequencing nucleic acids, mutagenesis of nucleic acid sequences, and producing nucleic acid probes for hybridization. Of particular current interest are amplification reactions, such as PCR, that have greatly increased the rate at which researchers can perform nucleic acid related experimentation. Extremely rare nucleic acids can now be amplified and manipulated using these techniques, which necessarily involve nucleic acid polymerases.

Using techniques with an amplification step has driven concern for the efficiency, fidelity, and sensitivity of the polymerase used. This has resulted in efforts to both analyze and optimize polymerization conditions for a variety of applications. (Lundberg et al., Gene 108: 1–6 (1991); Eckert and Kunkel, PCR Methods Applic. 1: 17–24 (1991); Ling et al., PCR Methods Applic. 1: 63–69 (1991); Brail et al., Mutat. Res. 303: 75–82 (1994); Garrity and Wold, P.N.A.S. 89: 1021–1025 (1992); Taylor and Logan, Curr. Opin. Biotechnol. 6: 24–29 (1995)) In particular, quantitative amplification-based reactions rely upon the ability to efficiently amplify each nucleic acid species present in a sample. (See Ausubel, et al., Chapter 15, In: Current Protocols in Molecular Biology, John Wiley & Sons (1992) and supplements through 1995.) Thus, both a concern for the accuracy of and a need for new methods to enhance the performance of amplification-based nucleic acid techniques exists in the art.

One way in which these concerns and needs have been addressed is through the use of additives to the amplification reaction. Different additives act at different points in the amplification process. For example, formamide has been used to increase the specificity of PCR with GC rich target sequences, which are particularly susceptible to intramolecular hybridization that may prevent hybridization with a primer. (Sarkar, G. et al. Nucl. Acids Res. 18: 7465 (1990)).

It has also been reported that tetramethylammonium chloride increases yield and specificity of PCR reactions. (Chevet, E., et. al., Nucleic Acids Res. 23:3343–3334 (1995) .) Hung et al. report the reduction in multiple satellite bands from amplifying complex DNA when dimethyl sulfoxide (DMSO) is added. (Hung, T., et al. Nucl. Acids Res. 18: 4953(1990).) The multiple satellite bands often present problems in purifying the desired amplification product from the other DNA present.

Certain proteins have been used to stabilize hybridized nucleic acids during replication. For example, *E. coli* single-stranded DNA binding protein has been used to increase the yield and specificity of primer extension reactions and PCR reactions. (U.S. Pat. Nos. 5,449,603 and 5,534,407.) The gene 32 protein (single stranded DNA binding protein) of phage T4 apparently improves the ability to amplify larger DNA fragments (Schwartz, et al., Nucl. Acids Res. 18: 1079 (1990)) and enhances DNA polymerase fidelity (Huang, DNA Cell. Biol. 15: 589–594 (1996)). In addition, bacterial thioredoxin combined with T7 DNA polymerase (Sequence) has been used to increase processivity, but not at high temperatures such as those used in PCR.

Another way amplification-based assays and techniques have been improved is through the development of modified polymerases or the use of combinations of polymerases. (U.S. Pat. No. 5,566,772) For example, the TaKaRa long PCR kit employs two polymerases (Takara Shuzo Co., Ltd; Japan), and a number of polymerase combinations were also tested by Barnes (Proc. Nat. Acad. Sci. USA, 91:2216–2220 (1994). Truncated Taq and *T. flavus* DNA polymerase enzymes that apparently exhibit increased thermostability and fidelity in PCR have also been suggested. (U.S. Pat. No. 5,436,149.) Combinations of polymerases with and without 5'→3' exonuclease or 3'→5' proofreading activity have also been used. (U.S. Pat. No. 5,489,523)

Further, amplification-based assays and techniques have been improved through empirical testing of conditions, reagents, and reagent concentrations to optimize polymerization reactions with a particular enzyme. Temperature and length of amplification cycles, primer length, and pH, for example, are all conditions that can be optimized. (Barnes, Proc. Nat. Acad. Sci. USA, 91:2216–2220 (1994).)

However, accessory proteins can be even more useful in improving polymerase activity and/or the processivity of polymerases. "Processivity" in this context refers to the number of enzymatic reactions occurring each time an enzyme binds to its substrate. In the context of nucleic acid replication reactions, "processivity" means the number of bases that can be replicated when the polymerase binds to a priming site. An increase in processivity directly relates to longer replication products.

Intracellular replication has been shown to involve accessory proteins, as characterized in *E. coli*, human, and phage T4 systems. The accessory proteins interact with polymerases to improve activity and provide the high processivity necessary to replicate genomic DNA efficiently while avoiding unacceptable mutation rates. Since the accessory proteins can be used in combination with the other improvements noted above, the development and application of accessory proteins holds particular promise for enhancing the results of nucleic acid replication-based reactions.

Accessory proteins have been identified in eukaryotes, *E. coli*, and bacteriophage-T4 and are thought to form "sliding clamp" structures. (Kelman and O'Donnell, Nucl. Acids. Res. 23(18): 3613–3620 (1995).) These structures are thought to tether the polymerase to DNA, thereby increasing processivity. The sliding clamp structures, however, have largely been studied in vivo and in model systems. Only in the case of T4 polymerase has knowledge of the activity of such accessory proteins been used to improve polymerization-based techniques employed by researchers in the art. For example, accessory proteins of the T4 holoenzyme have been reported to improve processivity when added to polymerization systems using T4 polymerase. (Young et al., Biochem. 31(37): 8675–8690 (1992); Oncor Fidelity™ Sequencing System, Oncor; Gaithersburg, Md.) However, since the T4 accessory proteins are derived from bacteriophage, they are not likely to enhance polymerases from bacteria, archeabacteria, or eukaryotes. Thus, the use of T4 accessory proteins is believed to have been limited to techniques where T4 polymerase is used.

Accordingly, since present knowledge and use of accessory proteins has led to limited applications in replication-based techniques, there continues to exist a need in the art for new and more widely useful compositions for enhancing polymerase enzyme activity. The present invention meets this need.

SUMMARY OF THE INVENTION

The present invention comprises extracts, protein complexes, and related proteins that possess nucleic acid polymerase enhancing activity which are useful in a variety of replication reactions known in the art. Thus, the extracts, protein complexes, and related proteins of the invention function to enhance a wide spectrum of in vitro nucleic acid replication reactions by providing, inter alia, replication products of superior length, fidelity, or both, and higher yields. As used in this specification and appended claims "polymerase enhancing activity" means the ability to increase the rate, fidelity, and/or yield of a nucleic acid polymerization reaction mediated by a nucleic acid polymerase, or to expand or alter the range of conditions under which such reaction does or may proceed.

In one aspect of the invention, extracts of *Pyrococcus furiosus* (*Pfu*) cells are provided that enhance the activity of *Pfu* DNA polymerase. The extracts enhance nucleic acid replication product yields over a fairly broad range of concentrations and contain at least one polymerase enhancing factor. As used in this specification and in the appended claims, the term "PEF" includes purified naturally occurring polymerase enhancing factors and wholly or partially synthetic copies or active analogs thereof. In accordance with the invention, such extracts can be further purified by heparin affinity chromatography followed by sepharose gel purification. Additionally, PEFs can be identified and purified using the antibodies of this invention, discussed below. While *Pfu* cell samples were used and are specifically exemplified below, one skilled in the art will appreciate that other cell samples can be used to identify and purify PEFs. For example, other species of the archeabacteria Pyrococcus or Thermococus can be used as well as thermophilic bacteria cells and other bacteria cells.

In another aspect of the invention, PEF complexes are provided. The PEF complexes of the invention possess polymerase enhancing activity and generally comprise multiple protein subunits with a combined molecular weight of approximately 250 kD or above as determined by SDS-PAGE analysis and gel filtration of unheated PEF samples. An example of one PEF complex (P300) was purified from *Pfu* cell sample extracts. The predominant components of the complex are a 50 kD protein (P50) and a 45 kD protein (P45). However, the PEF complex contains other minor components with approximate apparent molecular weights of 150, 100, 85, 60, 55, 42, and 37 kD. At least two components (150 and 100) have been shown to be dimeric or polymeric forms of P50. Thus, the PEF complexes of the invention comprise protein components and function to enhance the activity of polymerases.

In another aspect of the invention, *Pfu* proteins possessing polymerase enhancing activity are provided. These proteins have molecular weights between approximately 42 and 60 kD. The 42–60 kD proteins may be used alone or in combination to enhance polymerase activity. Methods for purifying these proteins as well as the PEF extracts and PEF complexes from which they have been isolated are also provided.

The invention also involves two particular proteins, *Pfu* P50 and P45, which are predominant components of the PEF complex (P300). Detailed structural information on the *Pfu* P45 and P50 proteins are disclosed. The P50 protein is similar in structure to a bacterial flavoprotein. The P45 protein is similar in structure to dCTP deaminase. The structural information herein can be used to generate specific hybridization probes that detect the presence of nucleic acids encoding a protein that is part of the PEF complex, or related proteins from samples from other species. Furthermore, the structural information can be used to generate proteins from expression systems known in the art, synthetic proteins, partially synthetic proteins, or proteins made from a combination of natural proteins, expressed proteins, and synthetic proteins. In addition, polyclonal or monoclonal antibodies that bind to PEF components can be produced, for example from purified P45 or P50, purified PEF complexes (P300), or another PEF of the invention. These antibodies can then be employed in assays and kits, well known in the art, in order to identify the presence or absence of a PEF.

Kits for replicating nucleic acids and methods for using the PEF complexes, specific proteins of the complexes, and extracts containing PEF are also provided. In addition, the complexes, proteins, and extracts can be used in compositions comprising a polymerase. Ideally, the polymerase will be one that is enhanced by the complex, protein, or PEF. The PEF extracts, complexes and proteins of the present invention are particularly useful in mixtures with nucleic acid polymerases, such as native polymerases and those produced by recombinant DNA techniques, and kits containing such polymerases.

Also provided in the invention are methods for identifying proteins or complexes that influence nucleic acid polymerases. The source of the protein can be any bacterial or archeabacterial species. Certain embodiments involve methods for identifying proteins affecting polymerases used in amplification reactions, for example, alpha-type DNA polymerases such as DNA polymerases derived from Pyrococcus and Thermococcus species.

DESCRIPTION OF THE DRAWINGS

FIG. 2: lane 1, buffer; lanes 2,5 column fraction undiluted; lanes 3,6 column fraction diluted 1:10; lanes 4,7 column fraction diluted 1:100; FIG. 1: lane 1, buffer; lanes 2,4 column fraction diluted 1:10; lanes 3,5 column fraction diluted 1:100. In FIG. 2, lanes 5–7, cloned *Pfu* DNA polymerase has been omitted from the PCRs, while in FIG. 1, lanes 4 and 5, λAA742 template DNA has been omitted from the reactions.

FIG. 4 shows a duplicate of the master SDS-PAGE gel from which gel slices were excised. The following proteins were electrophoresed on both gels: lane A, 8 μl of native *Pfu* DNA polymerase (lot #24); lane B, pre-stained molecular weight markers (Novex); lane C, heparin sepharose fraction SCS #36 H.S. #78 4 μl (≈160 ng PEF). The samples were not pre-heated before loading, and the duplicate gel shown here was silver-stained. Gel slices 1–7 were recovered from lane A on the master gel, while slices 8–25 were recovered from lane C of the master gel. FIG. 3 shows the PCR enhancing activity of proteins eluted from SDS-PAGE gel slices 1–7 (native *Pfu* DNA pol.; lanes 1–7) and 9–20 (H.S. #78; lanes 9–20). The proteins were eluted as described in Example 2. One (1)μl of each gel slice, diluted 1:100 in cloned *Pfu* PCR buffer, was added to cloned *Pfu* PCRs as described in Example 1. In the left lanes of the gel is shown PCR product synthesis in the presence of 1 μl of buffer (–) or H.S. #78, diluted 1:1000 (0.001 μl), 1:10,000 (0.0001 μl), or 1:100,000 (0.00001 μl). DNA markers were electrophoresed in lane "m".

FIG. 16. A 1.9 kb lacI-lacZα target was amplified from plasmid DNA. 100 μl PCRs were conducted with 50 pg of pPRIAZ, 100 ng of primers (5'CAT AGC GAA TTC GCA AAA CCT TTC GCG GTA TGG 3' (SEQ. ID NO: 20); 5'ACT ACG GAA TTC CAC GGA AAA TGC CGC TCA TCC 3' (SEQ ID NO: 21)), and 5 U cloned *Pfu* DNA polymerase in the absence (duplicate samples #18) or the presence (duplicate lanes #19) of 0.5 μl of a PEF-containing heparin sepharose fraction (H.S. #75; prep. 4; ≈10 ng/μl PEF). PCR cycling was conducted on a GeneAmp PCR System 9600 (Perkin Elmer Cetus) using the following conditions: 30 s at 95° C. (1 cycle)/5 s at 95° C.; 1 min. at 55° C.; 2.5 min. at 72° C. (30 cycles). FIG. 17. A 10 kb target from lambda DNA was amplified. 100 μl PCRs were conducted with 250 ng of lambda DNA (Sigma), 250 ng of primers (F51-20 5'GGC-GTT-TCC-GTT-CTT-CTT-CG 3' (SEQ ID NO: 22) R10163-20 5'CCA-TCT-CAC-GCG-CCA-GTT-TC 3' (SEQ ID NO: 23)), and 5 U cloned *Pfu* DNA polymerase in the absence (lane 1) or the presence of 1 μl of a S200-purified PEF (prep. 3; 550 ng/μl PEF) diluted 1:500 (lane 2), 1:50 (lane 3), or 1:5 (lane 4). PCR cycling was conducted on a Robocycler 40 (Stratagene) using the following conditions: 95° C. for 1 min. (1 cycle)/95° C. for 1 min.; 62° C. for 1 min.; 72° C. for 10 min. (30 cycles). FIG. 18. Lanes 1–5, a 5.2 kb portion of the human α1 antitrypsin gene was amplified from genomic DNA. 25 μl PCRs were conducted with 62.5 ng of human genomic DNA (Promega), 50 ng of primers (F91-23 5'GAG GAG AGC AGG AAA GGT GGA AC (SEQ ID NO: 24); R5271-21 5'GCT GGG AGA AGA CTT CAC TGG) (SEQ ID NO: 25), and 0.6 U cloned *Pfu* DNA polymerase in the absence (lane 1) or the presence of 1 μl of S200 purified PEF (SCS #52; 0.7 ug/ul) diluted 1:1000 (lane 2), 1:10,000 (lane 3), 1:100,000 (lane 4) or 1:1,000,000 (lane 5). PCR cycling was conducted on a RoboCycler 96 (Stratagene) using the following conditions: 96° C. for 45 s (1 cycle)/96° C. for 45 s; 60° C. for 45 s; 72° C. for 14 min. (35 cycles)/72° C. for 10 min. (1 cycle).

In FIG. 21, 25 μl PCRs were conducted using the 6.2 kb test system (example 1) with 25 U/ml Pwo DNA polymerase and 1×cloned *Pfu* PCR buffer. 1 μl of S200-purified *P. furiosus* PEF (prep 1; 225 ng/μl) was added undiluted (lane 1) or diluted 1:10 (lane 2), 1:1000 (lane 3), 1:10,000 (lane 4). 1 μl of dilution buffer was added as a negative control (lane 5). In FIG. 22, a 10 kb lambda DNA target was amplified from lambda DNA (lanes 1–4; 5–7; 11–13) or mouse genomic DNA, containing 40 copies (lanes 8–10) or 1 copy (lanes 14–16) of a lambda DNA transgene. 100 μl PCRs were conducted with 250 ng of lambda DNA (Sigma) or 250 ng of mouse genomic DNA and 250 ng of primers (F51-20 5'GGC-GTT-TCC-GTT-CTT-CTT-CG (SEQ ID NO: 22); R10163-20 5'CCA-TCT-CAC-GCG-CCA-GTT-TC) (SEQ ID NO: 23). PCRs were conducted in Taq PCR buffer using 5 U Taq DNA polymerase (lanes 1–4) or 1 U JDF3 DNA polymerase (lanes 5–16). 1 μl of the following was added to PCRs: S200-purified PEF (prep. 3; 550 ng/μl PEF) diluted 1:500 (lanes 2, 12, 15), 1:100 (lanes 6,9), 1:50 (lane 3), 1:10 (lanes 7,10,13,16), or 1:5 (lane 4). 1 μl of dilution buffer was added as a negative control (lanes 1,5,8,11,14). PCR cycling was conducted on a Robocycler40 (Stratagene) using the following conditions: 95° C. for 1 min. (1 cycle)/95° C. for 1 min.; 62° C. for 1 min.; 72° C. for 10 min. for Taq or 5 min. for JDF3 (30 cycles). In FIG. 23, the 1.9 kb ligase gene was amplified from *P. furiosus* genomic DNA. 100 μl PCRs were conducted with 250 ng of DNA and 250 ng of primers (5'GAG CTT GCT CAA CTT TATC (SEQ ID NO: 26); 5'GAT AGA GAT AGT TTC TGG AGA CG) (SEQ ID NO: 27). PCRs were conducted with 10 U ES4 DNA polymerase in c*Pfu* PCR buffer (lanes 1,2), 1.5 U JDF3 DNA polymerase in Taq PCR buffer (lanes 3,4), 4 U *Pfu* DNA polymerase in cloned *Pfu* PCR buffer (lanes 5,6), 1 U Vent DNA polymerase in Vent PCR buffer (lanes 7,8), or 1 U Taq DNA polymerase in Taq PCR buffer (lanes 9,10). 1 μl of the following was added to PCRs: dilution buffer (lanes 1,3,5,7,9) or S200-purified PEF (prep. 3; 550 ng/μl PEF) diluted 1:100 (lanes 2,4,6,8,10). PCR cycling was conducted on a DNA Thermal Cycler 480 (Perkin Elmer Cetus) using the following conditions: 95° C. for 1 min.; 46° C. for 1 min.; 72° C. for 2 min. (30 cycles). In FIG. 24, a 2 kb DNA target was amplified from transgenic mouse genomic DNA. 100 μl PCRs were conducted with 250 ng of DNA and 250 ng of primers (F51-20 5'GGC GTT TCC GTT CTT CTT CG (SEQ ID NO: 22); R2092-23 5'CGG GAT ATC GAC ATT TCT GCA CC) (SEQ ID NO: 28). PCRs were conducted with 0.75 U Deep Vent DNA polymerase in Deep Vent PCR buffer (lanes 1–4). 1 μl of the following was added: dilution buffer (lane 1) or S200-purified PEF (prep. 3; 550 ng/μl PEF), diluted 1:500 (lane 2), 1:100 (lane 3), 1:50 (lane 4). PCR cycling was conducted on a Robocycler40 (Stratagene) using the following conditions: 95° C. for 1 min.(1 cycle)/95° C. for 1 min.; 62° C. for 1 min.; 72° C. for 2 min. (30 cycles).

An extension time of 7.5 minutes was used for PEF-containing reactions, while an extension time of 15 minutes was used for reactions lacking PEF.

FIG. 27. Enhancement of *Pfu* DNA polymerase-based QuikChange mutagenesis with *P. furiosus* PEF. QuikChange mutagenesis was performed using the kit control primers and plasmid template, with either native or cloned *Pfu* DNA polymerase. To the reactions was added 1 μl of dilution buffer or 1 μl of a PEF-containing heparin sepharose fraction (SCS #36 H.S. #78; prep. 2≈40 ng/μl), diluted as indicated. The relative amount of linear amplification product was assessed by the intensity of ethidium bromide-stained product bands on agarose gels. Supercompetent *E. coli* cells were transformed with the digested amplification products. The number of amp resistant colonies and the mutation frequencies were scored.

Figure 28:
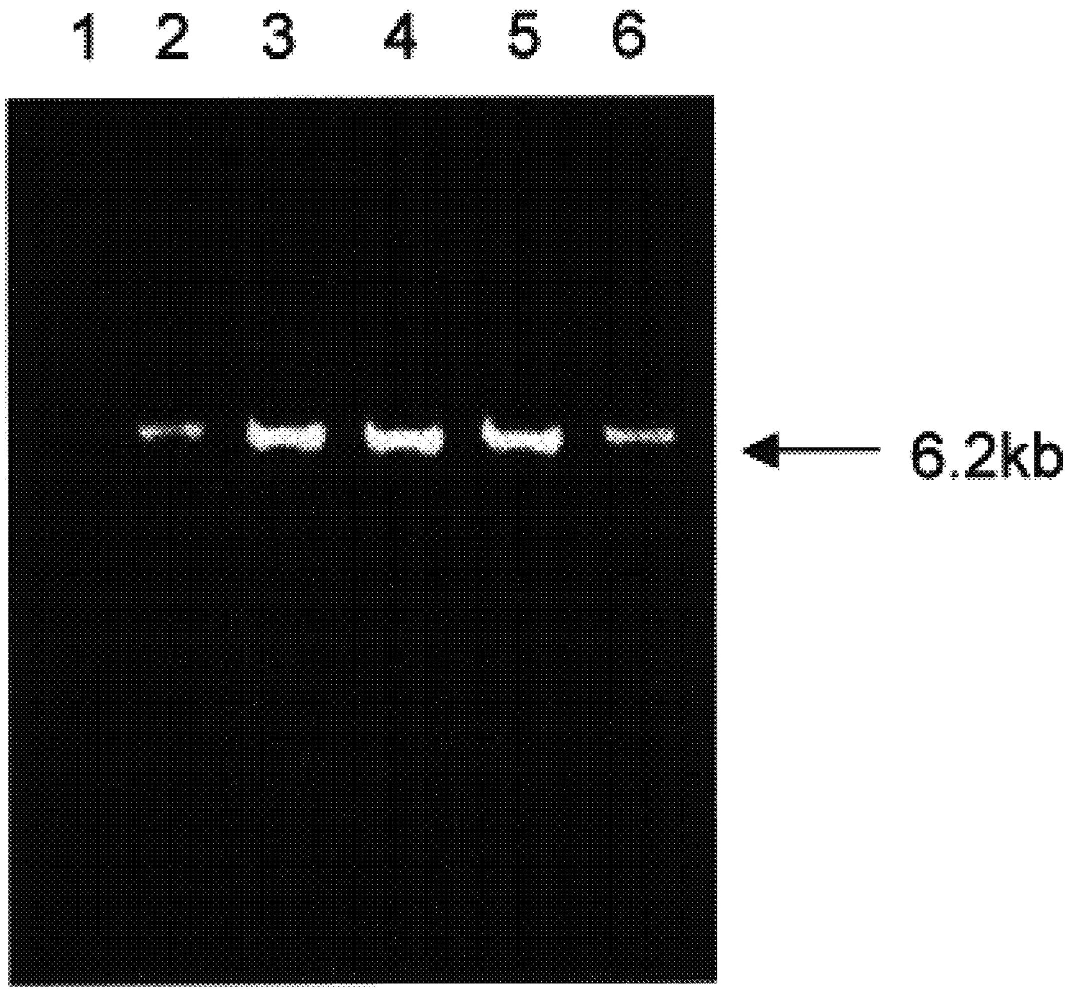
Figure 29:
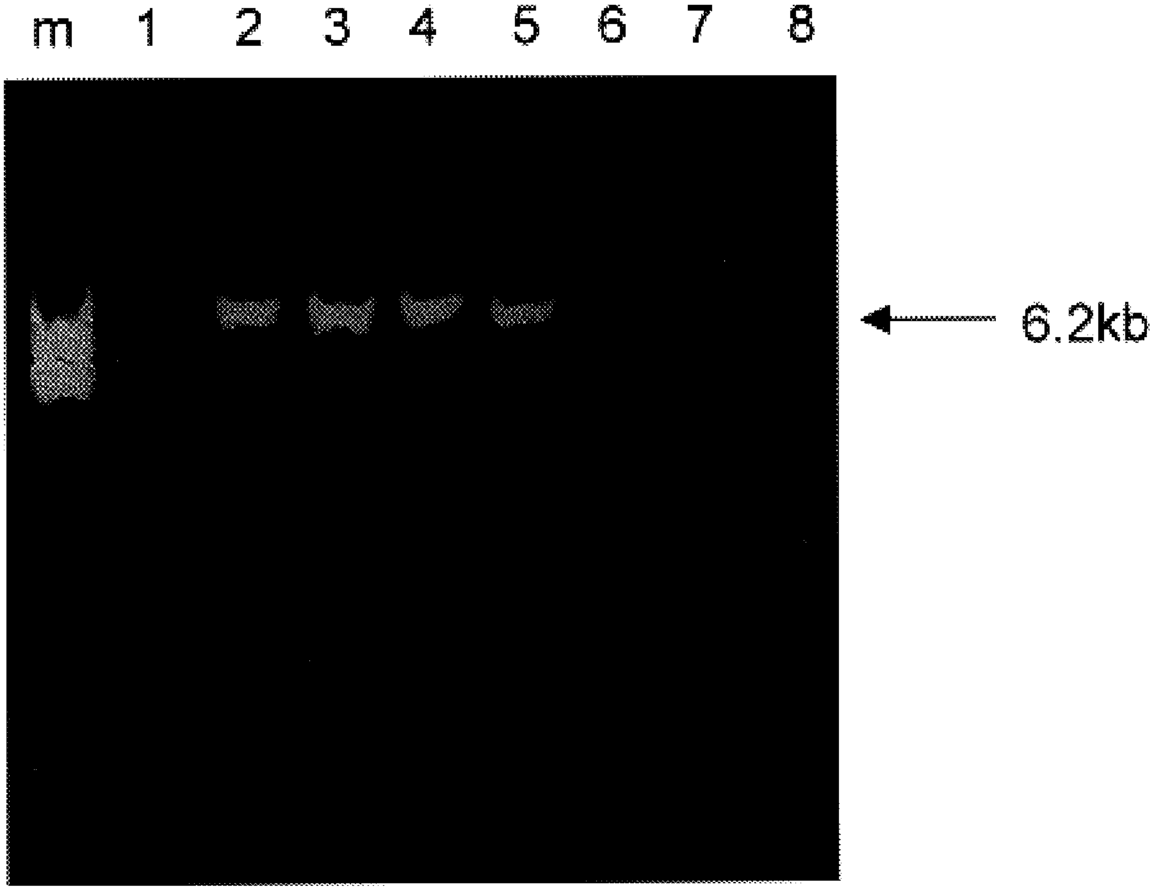

FIGS. 28 and 29. PCR enhancing activity of S200-purified *P. furiosus* PEF. PCR enhancing activity was measured in duplicate assays using the 6.2 kb test system described in Example 1. In FIG. 28, purified PEF (225 ng/μl; prep. 1) was diluted in 1×cloned *Pfu* PCR buffer and 1 μl aliquots of the following were added to 24 μl PCRs—lane 1, buffer; lane 2, PEF undiluted; lanes 3–6, PEF diluted 1:10, 1:100, 1:1000, 1: 10,000, respectively. In FIG. 29, the following amounts of purified PEF were added: lane 1—1 μl of buffer, lane 2—1 μl PEF neat, lanes 3–8, 1 μl PEF diluted 1:10, 1:100, 1:1000, 1:10,000, 1:100,000, and 1:1,000,000.

Figure 30:
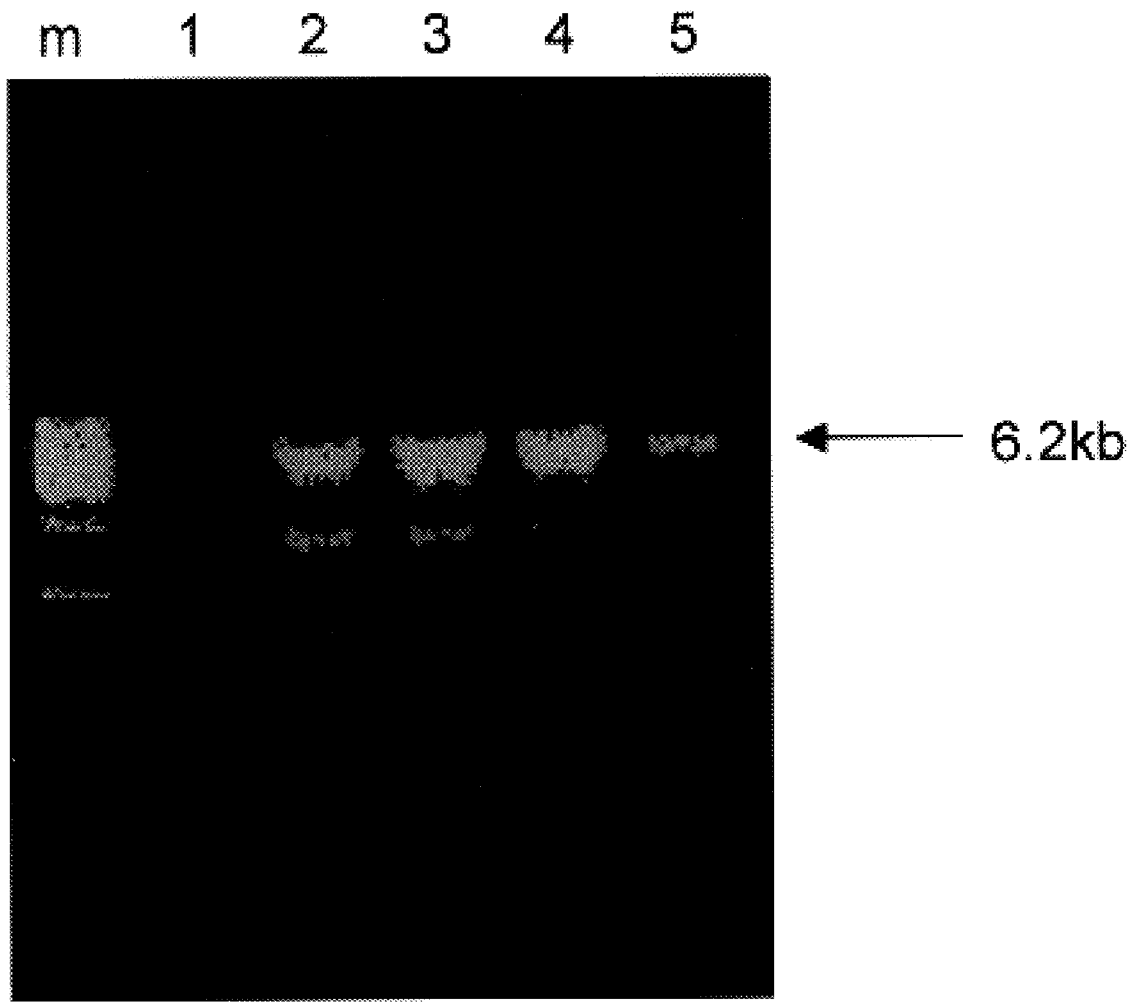
Figure 31:
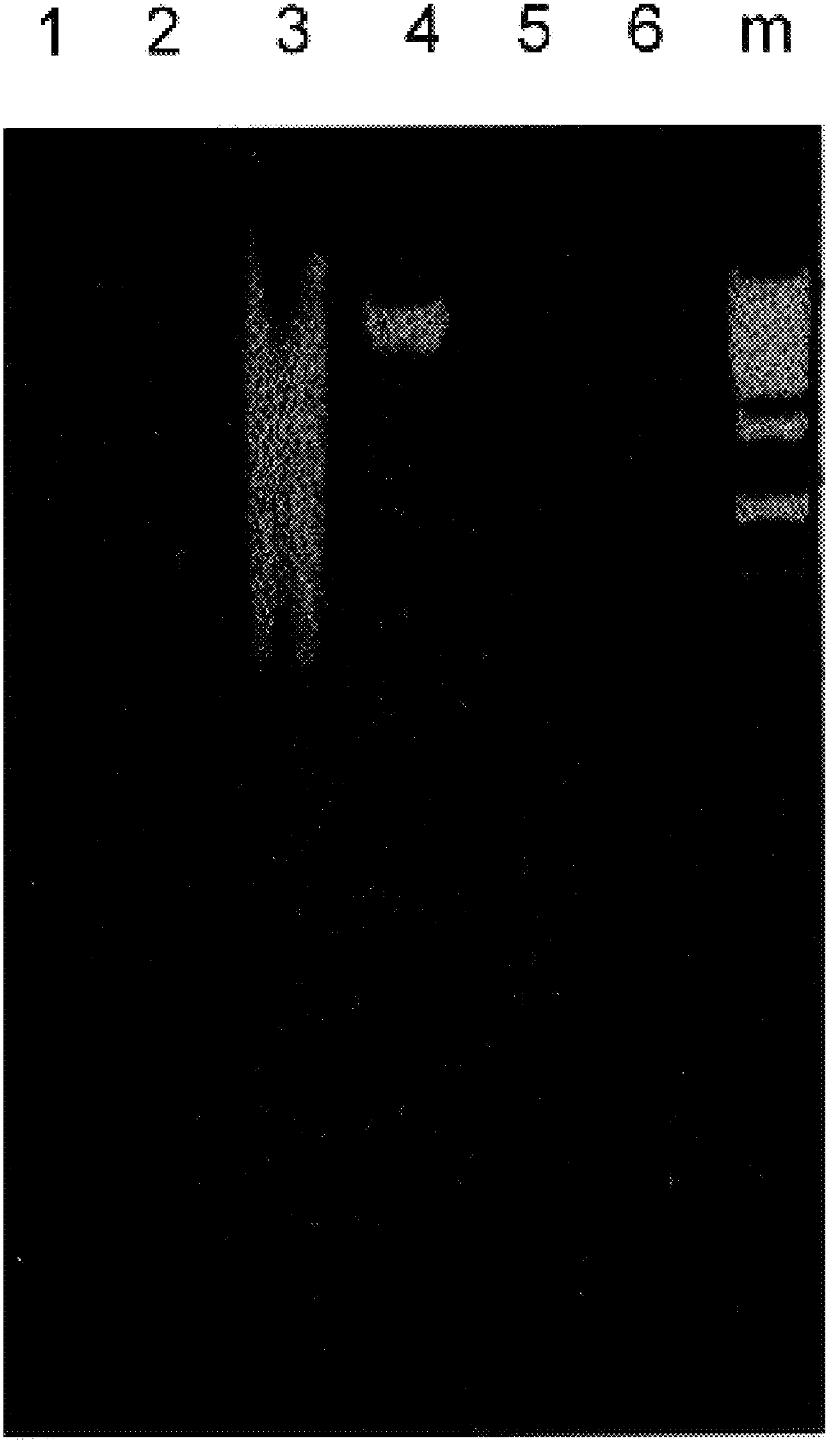

FIGS. 30 and 31. PCR enhancing activity of heparin sepharose-purified *P. furiosus* PEF. PCR enhancing activity was measured using the 6.2 kb test system described. The PEF fraction (≈40 ng/μl; prep. 2 in text) was diluted in 1×cloned *Pfu* PCR buffer. In FIG. 30, 1 μl aliquots of the following were added to 50 μl PCRs—lane 1, buffer; lanes 2–5, PEF diluted 1:10, 1:100, 1:1000, 1:10,000, respectively. In FIG. 31, 1 μl aliquots of the following were added to 24 μl PCRs—lane 1, buffer; lane 2, PEF undiluted; lanes 3–6, PEF diluted 1:10, 1:100, 1:1000, 1:10,000, respectively. DNA markers were electrophoresed in lane "m".

Figure 32:
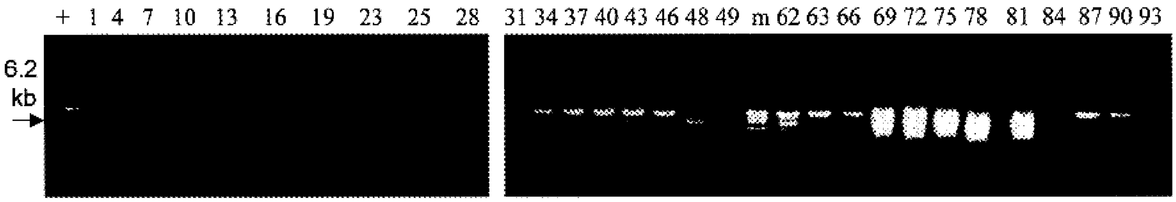

FIG. 32. PCR enhancing activity of heparin sepharose column fractions. The PCR enhancing activity contained in 1 μl of each column fraction (fractions 1–93; numbered at top) was measured using the assay described in Example 1. Fractions 50–61 contained the peak of *Pfu* DNA polymerase activity and were excluded from analysis.

DETAILED DESCRIPTION OF SPECIFIC EMBODIMENTS OF THE INVENTION

The following description should not be construed to limit the scope of this invention to any specifically described embodiment. Various aspects and embodiments of this invention will be apparent from the disclosure as a whole in context with the knowledge of one skilled in the art. In addition, the description herein, in combination with information known or available to persons of ordinary skill the art, enables the practice of the subject matter encompassed by the following claims.

For purposes of this invention, a nucleic acid replication reaction can mean any of the numerous nucleic acid amplification, primer extension, reverse transcription, or other nucleic acid polymerization reactions known in the art. Additionally, a replication reaction of this invention includes any reaction in which the ability of an enzyme to interact with a first nucleic acid and generate a second, substantially complementary nucleic acid sequence, is involved. The amplification reactions of this invention are not limited to PCR processes or any particular PCR-based assay, although they are particularly useful herein, and specifically include RT-PCR processes. The proteins, preparations, compositions, mixtures, kits and methods of this invention thus, can be used with any appropriately designed nucleic acid replication reaction.

As used herein, the term "PEF" refers to a naturally occurring protein derived from a bacterial or archeabacterial source (or wholly or partially synthetic copy or analog thereof) having polymerase enhancing activity mixtures of one or more such proteins, protein complexes containing one or more such proteins, or extracts containing one or more of such proteins, mixtures or complexes. The *Pfu* P45 and P50 proteins of this invention are illustrative of PEF proteins P45 and P50, which exhibit an apparent molecular weight of approximately 45 kD and 50 kD are predominant components of a PEF complex derivable from *Pfu*. Data relating to the P45 and P50 proteins is presented herein and details specific structural information on both of these components. The P45 protein appears to be the most active component, although full activity or stability may also require the presence of the P50 component. On SDS-PAGE, the PEF complex containing P45 and P50 as well as minor additional components migrates with an apparent molecular weight >250 kD. One species of the PEF complexes of this invention is the P300 complex from *Pyrococcus furiosus*.

The present invention is intended, however, to encompass other PEF proteins, mixtures, complexes, and extracts derived from organisms other than *Pfu* identified by techniques analogous to those provided by the following examples, or by use of the structural information on the PEF proteins described herein or derivable from the proteins described herein. More specifically, the invention is intended to encompass PEFs identified on the basis of protein sequence homology to all or part of the PEFs described herein, nucleic acid homology to all or part of the DNA sequence encoding the proteins described herein or DNA sequences described herein, or reactivity with antibodies to the proteins, complexes, or extracts disclosed herein.

One skilled in the art is familiar with methods of generating analogs of proteins. Various techniques from publications in the art can be used to mutate, modify, truncate, or otherwise change a protein. Similarly, wholly or partial synthetic or recombinantly expressed proteins can also be generated from the information herein by those skilled in the art. (For example, Ausubel et al. (1989) Current Protocols in Molecular Biology, and supplements through February 1997.)

EXAMPLE 1

Screening for PEF Activity

Protein containing extracts from a number of different sources can be tested for PEF activity. The extracts can be prepared in a number of ways known in the art.

One method was demonstrated with *Pfu* DSM 3638 cells. The cells are grown, a cell paste collected by centrifugation and then frozen at −80° C. The paste was taken up with lysis buffer [50 mM Tris-HCl (pH 8.2), 1 mM EDTA, 10 mM B-mercaptoethanol, 0.5 mM PMSF, and 2 μ/ml aprotinin], and thereafter the cells are lysed in a French press and then sonicated. Following sonication, the lysate is centrifuged and the supernatant, containing potential PEFs, is collected for assays.

1. Screening Assays for PCR-Enhancing Activity

One method of detecting thermostable PEFs is by screening partially-purified fractions from thermophilic archeabacterial or bacterial extracts for PCR enhancing activity. PCR enhancing activity can be detected in samples consisting of column-purified fractions as well as homogeneous protein samples and proteins recovered by elution from SDS-PAGE gel slices (see below). Samples are added to PCR amplification reactions containing DNA polymerase, buffer, dNTPs, primers, and DNA template. PCR enhancing activity is identified by an increase in PCR product yield for amplifications conducted in the presence of a particular sample (DNA polymerase+PEF) as compared to amplifications conducted in the absence of added sample (DNA polymerase only).

When screening samples suspected of containing endogenous DNA polymerase activity, for example protein extracts, negative controls can be performed in which the exogenous DNA polymerase has been omitted from the PCR amplifications. In addition, when screening samples contaminated with DNA, negative controls can be carried out in which exogenous DNA template is omitted from the PCR amplifications.

The sensitivity of the PCR enhancing assay is dependent on the complexity of the DNA targets employed. PCR reaction parameters (target complexity, DNA template concentration, polymerase concentration, PCR cycle number or extension time) can be adjusted so that the yield of PCR product is barely detectable under normal conditions. In addition, samples can be diluted appropriately so that the concentration of PEFs falls within the detectable range of the PCR enhancing activity assay.

2. Screening Assays for PCR-Enhancing Activity Using *Pfu*-derived Samples

For screening PEFs from *Pyrococcus furiosus*, a master PCR cocktail was prepared consisting of: 200 μM each dNTP, 2 μg/ml primer F432-21 (5'-CTA-TTG-AGT-ACG-AAC-GCC-ATC) (SEQ ID NO.: 49); 2 μg/ml primer R6656-20 (GTC-ACG-CTT-GCT-CCA-CTC-CG) (SEQ ID NO.: 50), 2.5 μg/ml λAA742 DNA (transgenic mouse DNA with 40 copies of the lac1 transgene), 1×cloned *Pfu* DNA polymerase PCR buffer (10 mM KCl, 10 mM $(NH_4)_2SO_4$, 20 mM Tris-HCl (pH 8.8), 2 mM $MgCl_2$, 0.1% (v/v) Triton X-100, and 100 μg/ml BSA), and 25 U/ml cloned *Pfu* DNA polymerase. Samples were diluted in 1×cloned *Pfu* DNA polymerase PCR buffer, and 1 μl of each diluted sample was added to 24 μl of the PCR cocktail. PCR amplifications were conducted on the RoboCycler 96 Temperature Cycler (Stratagene), using the following conditions: 96° C. for 45 s (1 cycle)/96° C. for 45 s; 60° C. for 45 s; 72° C. for 14 min. (35 cycles)/72° C. for 10 min. (1 cycle).

PCR products (10 μl/lane) are run out on 1% agarose gels and PCR product bands visualized by ethidium bromide staining. Samples with PCR enhancing activity exhibit higher yields of the expected 6.2 kb PCR product than can be obtained in the presence of DNA polymerase alone. When PCR enhancement is due to the presence of PEFs, rather than contaminating endogenous DNA polymerase activity, amplifications performed in the absence of exogenous DNA polymerase (e.g. *Pfu* DNA polymerase) yield no PCR product. Moreover, PCR amplifications performed in the absence of exogenous DNA template should yield no PCR product when the PEF sample lacks contaminating target DNA.

3. Screening Assays for Nucleic Acid Replication Enhancing Activity

Extracts can also be added to any nucleic acid replication reaction to determine PEF activity. Many of these reactions are known in the art, including primer extension reactions, DNA sequencing reactions, site-directed mutagenesis reactions, and a number of PCR-based reactions. (Ausubel, F. M., et al. (1989) Current Protocols in Molecular Biology, Greene Publishing Associates and Wiley-lnterscience, New York, N.Y.; Sambrook, J., et al. (1989) Molecular Cloning: A Laboratory Manual, 2nd Ed., Cold Spring Harbor Laboratory Press, Cold Spring Harbor, N.Y.) By comparing the results produced in a nucleic acid replication reaction with and without the added extract, one can identify the presence of PEF.

EXAMPLE 2

Purification of PEF from *P. furiosus*

Once PCR enhancing activity has been detected from, for example, archeabacterial or bacterial sources, large amounts of purified PEF can be obtained by column chromatography. The following protocol was developed for purifying PEF from *P. furiosus* (*Pfu*). However, one skilled in the art will appreciate that other cells or species could be used as well.

1. Cell Growth and Lysis

*P. furiosus* DSM 3638 cells were grown in a 400 liter fermentor according to established protocol. (U.S. Pat. No. 5,545,552, specifically incorporated herein by reference.) The cell paste was collected using a Sharples in-line centrifuge after approximately 20 hours (A600≈0.5), and then immediately frozen in liquid $N_2$ and stored at −80° C. until use. Then, 500 grams of frozen cell paste was transferred to a 4 liter stainless steel beaker on ice. The cells were resuspended with 2 liters of lysis buffer, consisting of 50 mM Tris-HCl (pH 8.2), 1 mM EDTA, 10 mM B-mercaptoethanol, 0.5 mM PMSF, and 2 μg/ml aprotinin. The cells were lysed in the French press using 2 passes at 8K PSI and the lysate was then sonicated for 10 minutes. Following sonication, the lysate was transferred to 400 ml bottles, spun for 1 hour at 9K rpm in a Sorvall RC-2B centrifuge using a Sorvall GS3 rotor, and the supernatant collected.

2. Purification by Column Chromatography

The supernatant was loaded at a flow rate of 5 ml/min. onto a 10×5 cm Q-Sepharose Fast Flow column (≈392 mls), pre-equilibrated in buffer consisting of 50 mM Tris-HCl (pH 8.2), 1 mM EDTA, and 10 mM B-mercaptoethanol. The column was washed with 2 column volumes of buffer, and the pass-through and column washes were collected and pooled. The pooled fractions were adjusted to pH 7.5 using 1 N HCl.

The Q-Sepharose pass-through was then loaded at a flow rate of 5 ml/min. onto a 5×11.5 cm (≈225 mls) SP Sepharose Big Bead column, equilibrated in buffer containing 50 mM Tris-HCl (pH 7.5), 1 mM EDTA, 1 mM DTT, 10% (v/v) glycerol, 0.1% (v/v) Igepal CA-630, and 0.1% (v/v) Tween 20. The column was washed with equilibration buffer until the absorbance ($OD_{280}$) approaches baseline. The column was eluted with a 2 liter gradient from 0 to 250 mM KCl (in equilibration buffer). Fractions of 20 ml were collected, and aliquots removed from every third tube for SDS-PAGE analysis.

The fractions analyzed by SDS-PAGE showed a band >250 when a sample was not heated prior to electrophoresis (≈300 kD). The fractions containing the 300 kD band were pooled and dialyzed overnight against 2×4 liters of Buffer A [50 mM Tris-HCl (pH 8.2), 1 mM EDTA, 1 mM DTT, 10% (v/v) glycerol, 0.1% (v/v) Igepal CA-630, and 0.1% (v/v) Tween 20]. The dialyzed pool was loaded at a flow rate of 2 ml/min. onto a 2.6×29 cm (≈154 mls) Heparin Sepharose CL-6B column, equilibrated in Buffer A. The column was washed with 1 liter of Buffer A, and then eluted with a 1.5 liter gradient from 0 to 300 mM KCl/Buffer A. Fractions of 10 ml were collected, and aliquots removed from every third tube for SDS-PAGE analysis. Fractions containing the 300 kD band were pooled and dialyzed overnight against 2×4 liters of Buffer A.

The heparin sepharose-purified pool was loaded at a flow rate of 0.5 ml/min. onto a 1.6×95 cm (≈191 mls) Sephacryl S-200 High Resolution column equilibrated in Buffer A containing 100 mM KCl. Then, 2 ml fractions were collected and aliquots removed from every third tube for SDS-PAGE analysis. Fractions containing the 300 kD band were pooled and dialyzed overnight against 1 liter of buffer containing 50 mM Tris-HCl (pH 8.2), 0.1 mM EDTA, 1 mM DTT, 50% (v/v) glycerol, 0.1% (v/v) Igepal CA-630, and 0.1% (v/v) Tween 20. The purified protein was stored at −20° C. The purification protocol described above yielded ≈1 mg. of relatively homogeneous P300 band from 500 g. of cell paste.

3. Purification of PEF from SDS-PAGE Gels

PEF in a heterogeneous sample can be identified by eluting purified protein from SDS-PAGE gel slices and rescreening for PCR enhancing activity. This method allows rapid assessment of the number of PEF proteins in a particular sample and identification of their apparent molecular weight.

*Pfu* protein samples with PCR enhancing activity were electrophoresed on 4–20% acrylamide/2.6% bis-acrylamide Tris-Glycine gels (Novex), along-side pre-stained molecular weight markers. Samples were loaded in the presence of 2% SDS, but were not boiled in order to prevent dissociation of PEF complexes. The gels were run in Tris-Glycine buffer containing 1% SDS, and after electrophoresis, were washed briefly in 20 mM Tris-HCl (pH 8.0)/1 mM EDTA. Then, 2–3 mm gel slices were excised from the lanes of interest using the pre-stained molecular weight markers as a guide. Each gel slice was cut-up with a razor blade and the pieces transferred to 50 μl of elution buffer (20 mM Tris-HCl (pH 8.0)/1 mM EDTA/0.1% Tween-20). The slurry was incubated at 72° C. for 30 minutes.

Gel slices containing PEFs are identified by testing the eluates for PCR enhancing activity. Eluates containing >0.1 ng/μl PEF are then re-analyzed on silver-stained SDS-PAGE gels to verify the apparent molecular weight of the predominant protein component. The gel slice eluates are boiled in the presence of 2% SDS before loading and the apparent molecular weights of PEF proteins determined relative to protein standards. The gel slice elution procedure described here allows recovery of 1–10% of the protein of interest.

EXAMPLE 3

Figure 1:
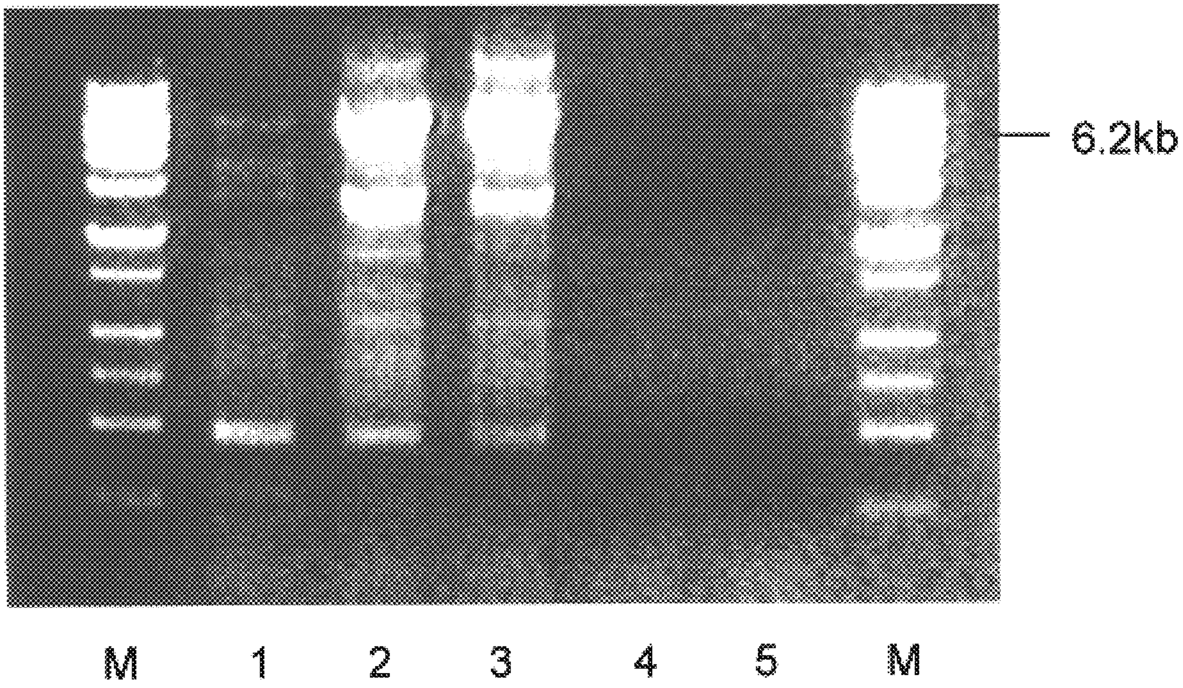
FIGS. 1 and 2. PCR enhancing activity in a heparin sepharose column fraction. PCR enhancing activity was measured using the 6.2 kb system described in example 1. Column fraction SCS #36 H.S. #78 (prep. 2 in text) was diluted in 1×cloned *Pfu* PCR buffer and 1 $\mu$l aliquots of the following were added to 100 $\mu$l PCRs.
Figure 2:

Identification of the PCR Enhancing Activity in *P. furiosus* Partially-Purified Column Fractions The fractions collected after the heparin sepharose chromatography were analyzed for PEF activity using the PCR screening assay. The addition of diluted heparin sepharose fraction dramatically increased yields of PCR products generated with cloned *Pfu* DNA polymerase. The PCR enhancing activity of the fractions was shown to be dependent upon the presence of exogenous DNA template (FIG. 1) and *Pfu* DNA polymerase (FIG. 2). Increased PCR product yield was, therefore, not due to the presence of contaminating DNA template or native *Pfu* DNA polymerase, but rather to the presence of PEFs.

Figure 3:
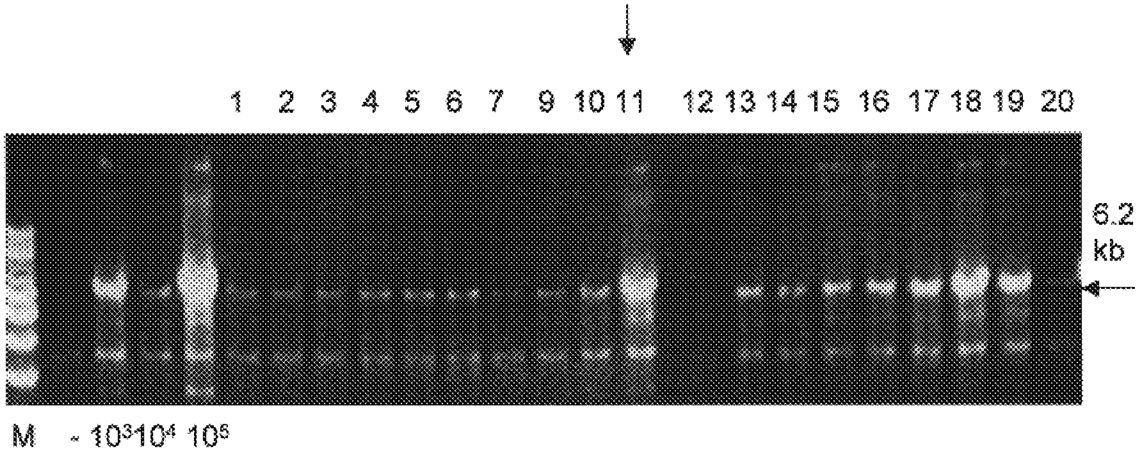
FIGS. 3 and 4. PCR enhancing activity of SDS-PAGE gel-purified samples from heparin sepharose fraction SCS #36 H.S. #78 (prep. 2 in text).
Figure 4:
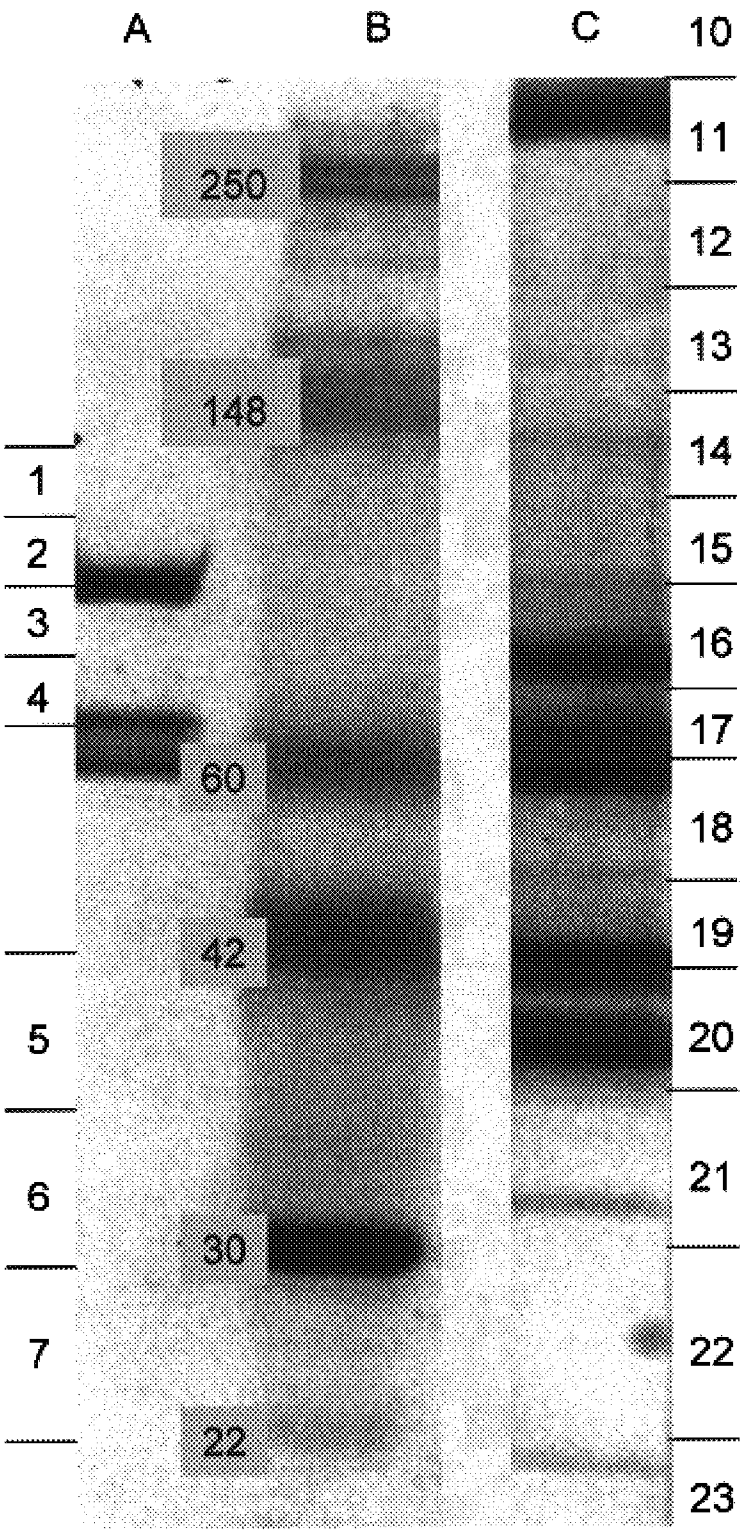

In order to further characterize the factor or factors responsible, the following was performed. PEFs after heparin sepharose chromatography were identified by screening SDS-PAGE gel-purified samples for PCR enhancing activity, as discussed above. When the protein samples were loaded onto SDS-PAGE gels without pre-boiling, PCR enhancing activity was recovered in 2 gel slices (FIG. 3). One gel slice (gel slice #1) was excised from a position between the 42 and 60 kD markers, while the second gel slice (slice #2) was recovered from a site just above the 250 kD marker (FIG. 4).

Figure 5:
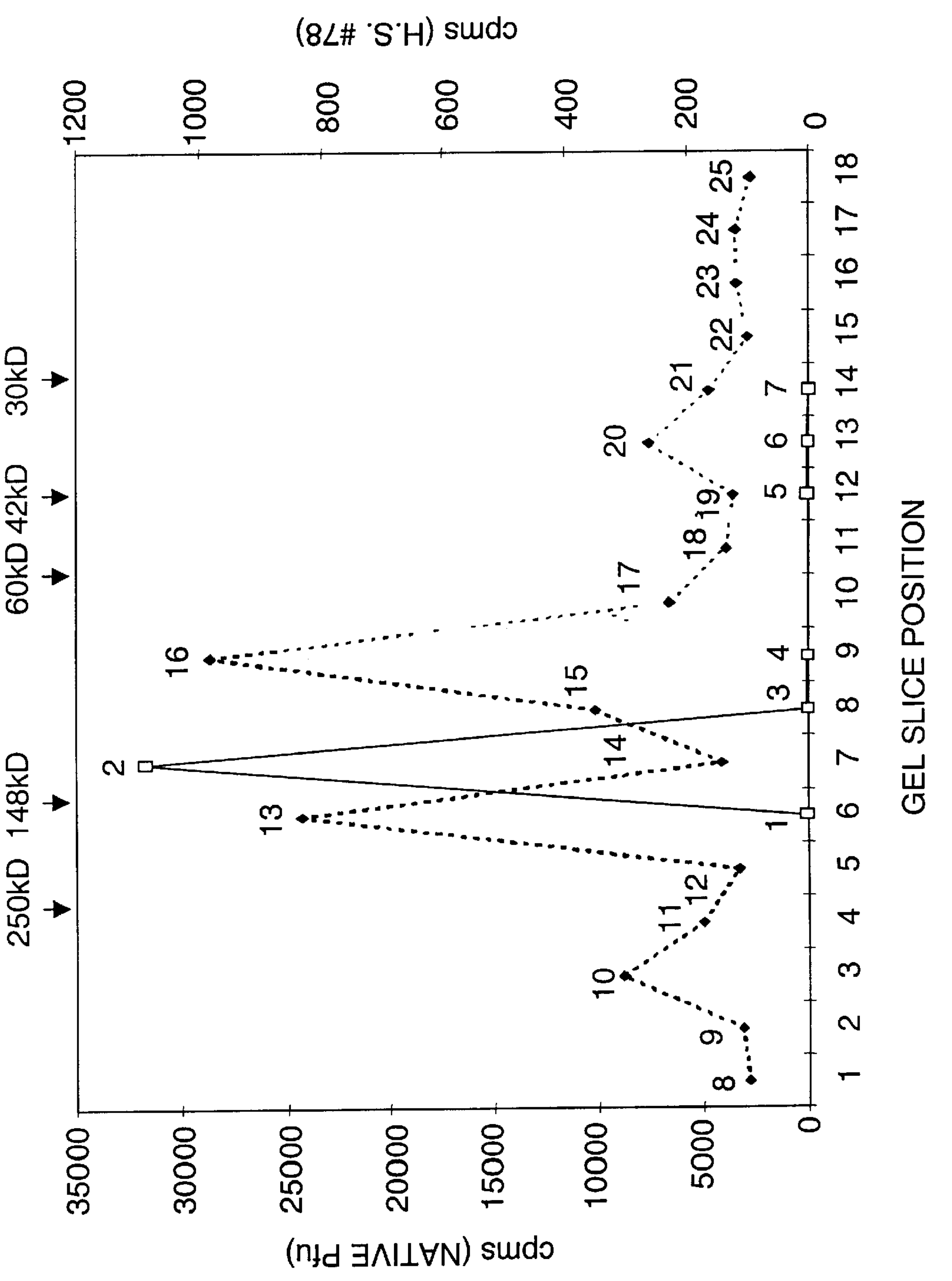
FIG. 5. DNA polymerase activity in SDS-PAGE gel purified samples. The level of DNA polymerase activity (cpms incorporated) in gel slice eluates (1 μl) was measured as described in Example 11. The polymerase activity exhibited by gel-purified proteins in the native *Pfu* DNA polymerase preparation (FIG. 4; lane A) is shown by the solid line (left handed Y axis). The polymerase activity of gel-purified proteins in fraction H.S. #78 (FIG. 4, lane C) is shown with the broken line (right-handed Y axis). The apparent molecular weights of the proteins tested are shown on the x axis (at the top) and are inferred from the position the gel slices were recovered, relative to pre-stained molecular weight markers. Gel slices #11 and 18 exhibited the highest PCR enhancing activity.

The proteins eluted from the gel slices were also screened for DNA polymerase activity to demonstrate that PCR enhancing activity was not related to contaminating DNA polymerase activity (FIG. 5). The results indicated that SDS-PAGE purified proteins with PCR enhancing activity lack significant DNA polymerase activity. Moreover, SDS-PAGE purified *Pfu* DNA polymerase lacks PCR enhancing activity when tested at protein concentrations comparable or greater than those of gel-purified PEFs.

Figure 6:
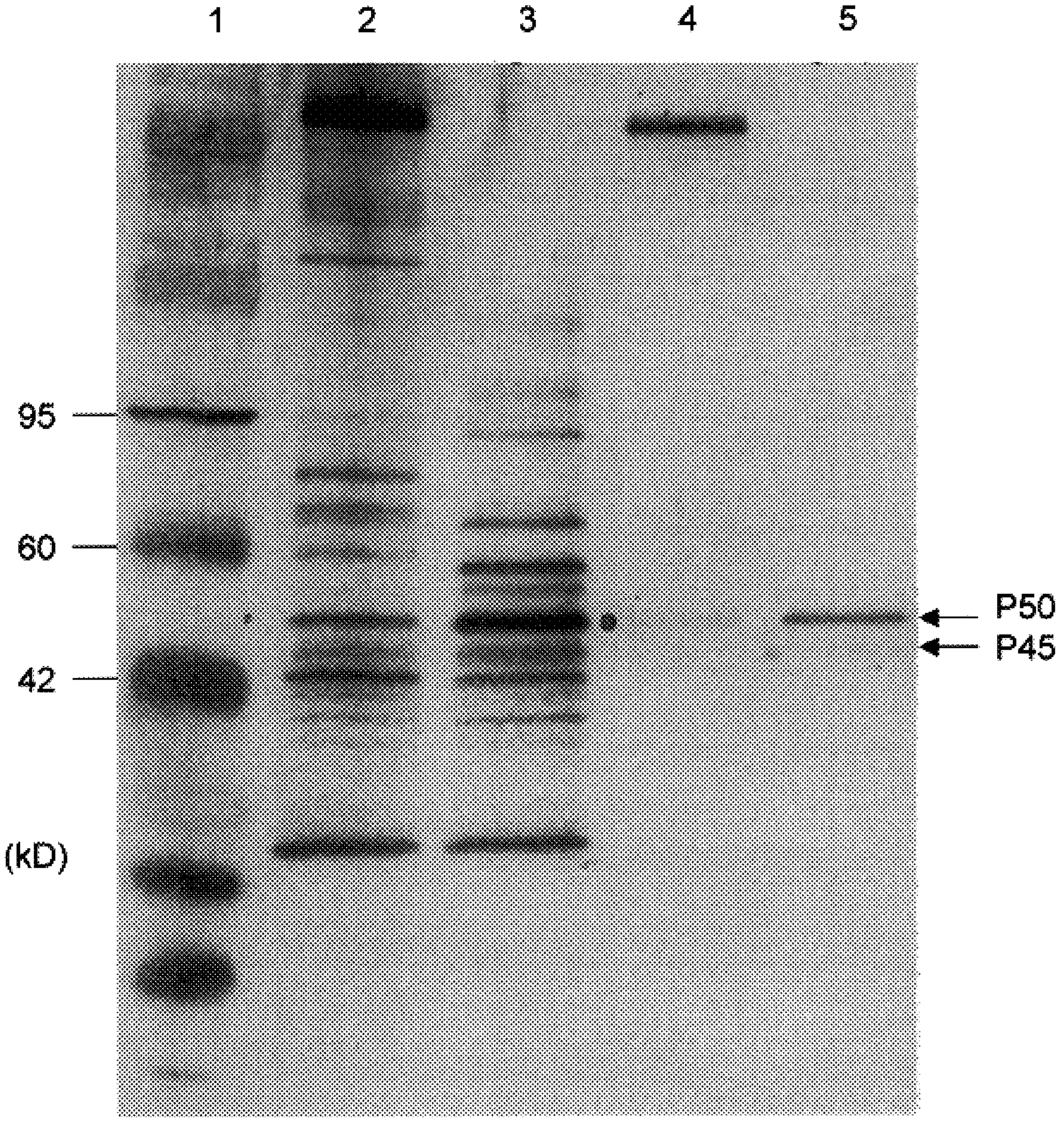
FIG. 6. SDS-PAGE analysis of gel-purified *P. furiosus* PEF. The following samples were electrophoresed on 4–20% acrylamide gels in the presence of 1% SDS: lanes 2,3-SCS #37 H.S. fraction #75 (prep. 4 in text; 10 μl of a Microcon 30 concentrated fraction; ≈100 ng PEF) lanes 4,5 10 μl of SDS-PAGE gel slice eluate recovered from SCS #37 H.S. fraction #75 (migrated 0–4 mm above 250 kD protein marker). The samples in lanes 2 and 4 were boiled for 3 minutes before loading onto the SDS-PAGE gel. The migration of pre-stained molecular weight markers is shown in lane 1.

The *P. furiosus* PEF proteins were conclusively identified by re-analyzing gel purified samples with PCR enhancing activity on silver stained SDS-PAGE gels. In the absence of pre-boiling, the predominant band in gel slice #2 migrates somewhat slower than the 250 kD molecular weight marker, consistent with the site where the gel slice was recovered (FIG. 6). This band is called P300 or PEF complex. In addition, a minor band is evident at 50 kD, called P50. Gel slice #1 contained a major band at 50 kD and a minor band at 45 kD.

However, when the proteins eluted from gel slice #2 are boiled in SDS prior to loading, the predominant component migrates with an apparent molecular weight of 50 kD (FIG. 6). A minor or poorly staining component of ≈45 kD is also visible. These results are consistent with *P. furiosus* PEF consisting of two distinct proteins, with apparent molecular weights of 50 kD and 45 kD, and which aggregate at low temperatures in presence of SDS to produce a complex which migrates as a discrete band at 300 kD.

EXAMPLE 4

Characterization of PEF Complex and Protein Components of the Complex

*Pfu* PEF fractions following S200 chromatography comprises a mixture of proteins. A discrete band in SDS-PAGE migrates above the 250 kD marker when the sample is not heated prior to electrophoresis. This protein is called P300 or PEF complex. When the conditions are changed to substantially dissociate the PEF complex, the subunit protein components of the PEF complex are visualized in SDS-PAGE.

1. Temperature-dependent Dissociation of PEF Complex

Figure 7:
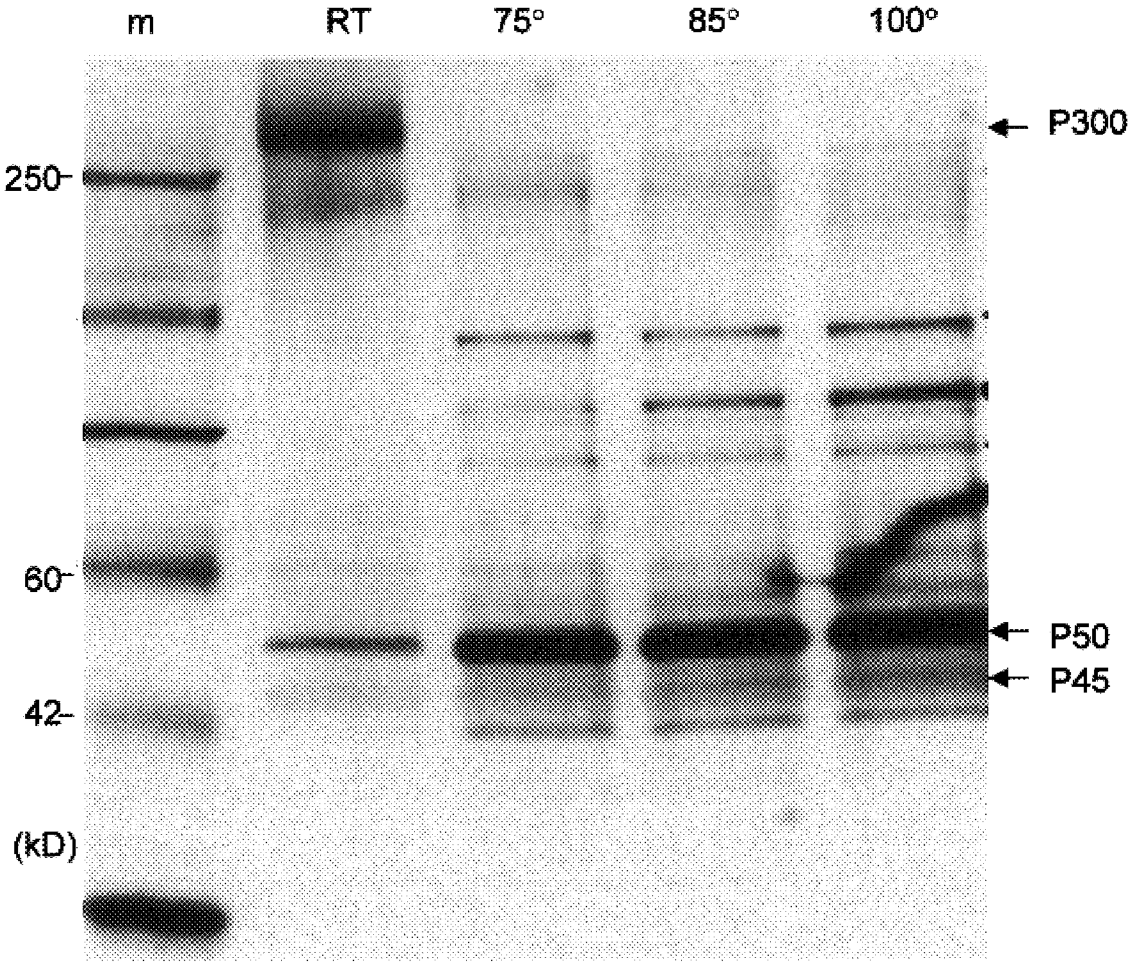
FIG. 7. SDS-PAGE analysis of S200-purified *P. fudiosus* PEF. 10 μl (2.25 μl) of S200-purified PEF (prep. 1) was incubated in the presence of 2% SDS for 3 minutes at room temperature, 75° C., 85° C., or 100° C. (as indicated on lanes) and then subject to electrophoresis as described in example 2. Proteins were detected by silver-staining. Protein molecular weight markers were run in lane "m".

One method of dissociating PEF complex into its component proteins is heat treatment. In the absence of heating, the majority of PEF migrates as a complex, running slightly slower than the 250 kD molecular weight marker. Minor amounts of dissociated P50 and P45 are visible in the unheated sample. However, after heat treatment at temperatures of about 85° C. or higher, the PEF complex is completely dissociated as indicated by the absence of the 300 kD band by SDS-PAGE. The predominant protein component of PEF complex exhibits an apparent molecular weight of approximately 50 kD in SDS-PAGE. The P50 band is shown in the gel of FIG. 7, where the protein was heated to ≧85° C. in the presence of 2% SDS and BME prior to loading. In addition, the P45 protein shown to be present in the gel-purified PEF complex (FIG. 6) is also evident in the heat-treated, S200-purified PEF sample (FIG. 7). Furthermore, minor components with apparent molecular weights of approximately 37, 42, 55, 60, 85, 100, and 150 kD were also detected in SDS-PAGE analyses of PEF complex treated at temperatures of 85–100° C. These minor components may represent additional forms of P50 and P45 generated by heat treatment (e.g. dimers, trimers, fragments) or minor unrelated species.

Figure 8:
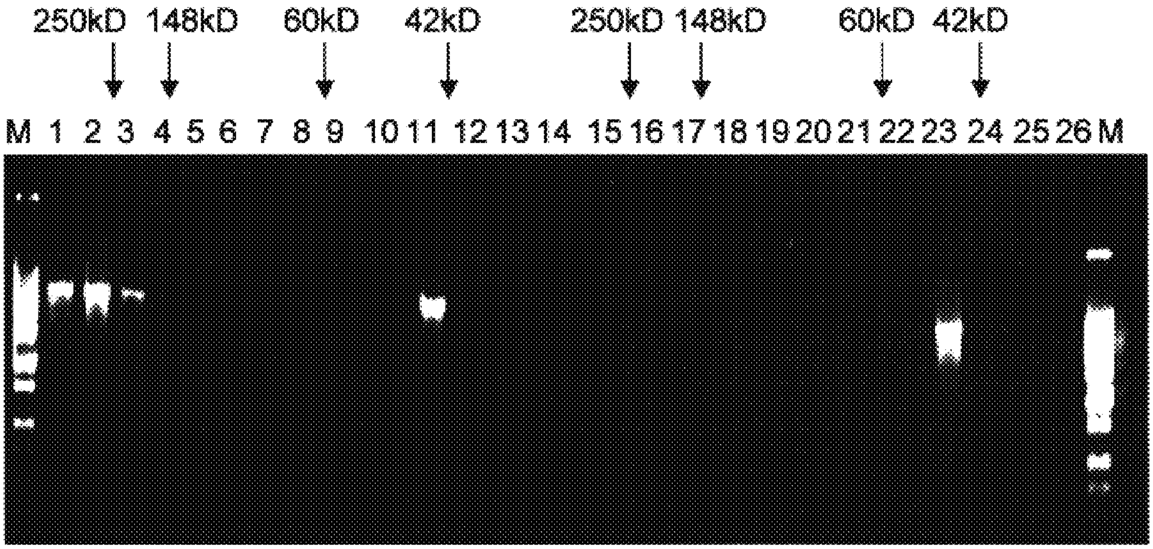
FIG. 8. PCR enhancing activity of SDS-PAGE gel-purified samples from an S200-purified *P. furiosus* PEF preparation (prep 1). Purified PEF (≈4.5 μg) was pre-incubated in 2% SDS for 3 minutes at room temperature (RT) or at 85° C. (85° C.) before electrophoresis. Proteins were eluted from SDS-PAGE gel slices 1–13 (gel RT) and 14–26 (gel 85° C.) as described in Example 2. One (1)μl of each gel slice, diluted 1:100 in cloned *Pfu* PCR buffer, was added to cloned *Pfu* PCRs as described in example 1. The approximate molecular weights of the SDS-PAGE gel-purified proteins is indicated at the top of the gel.

2. Polymerase Enhancing Activity of PEF Complex and Component Proteins and Mixtures Analysis of SDS-PAGE gel slice eluates indicates that PCR enhancing activity of S200-purified *P. furiosus* PEF can be attributed solely to the 45 kD species plus the 50 kD species. When an S200-purified preparation was loaded in the absence of heating (FIG. 7, prep. 1), PCR enhancing activity was present in gel slices recovered just above the 250 kD marker and between the 42 and 60 kD markers. When heated to 85° C. before loading, PCR enhancing activity migrated between the 42 and 60 kD markers (FIG. 8).

Titration experiments showed that the PCR enhancing titer of gel purified proteins migrating with apparent mass between 42 kD and 60 kD was not significantly different from that of the gel-purified PEF complex (300 kD band). The levels of PCR enhancing activity migrating between the 148 and 60 kD markers were insignificant, thereby indicating that the 85 kD, 100 kD, and 150 kD bands do not contribute substantially to full PCR enhancing activity of the PEF complex (P300). Moreover, these components do not appear to further enhance the activity of PEF.

Figure 9:
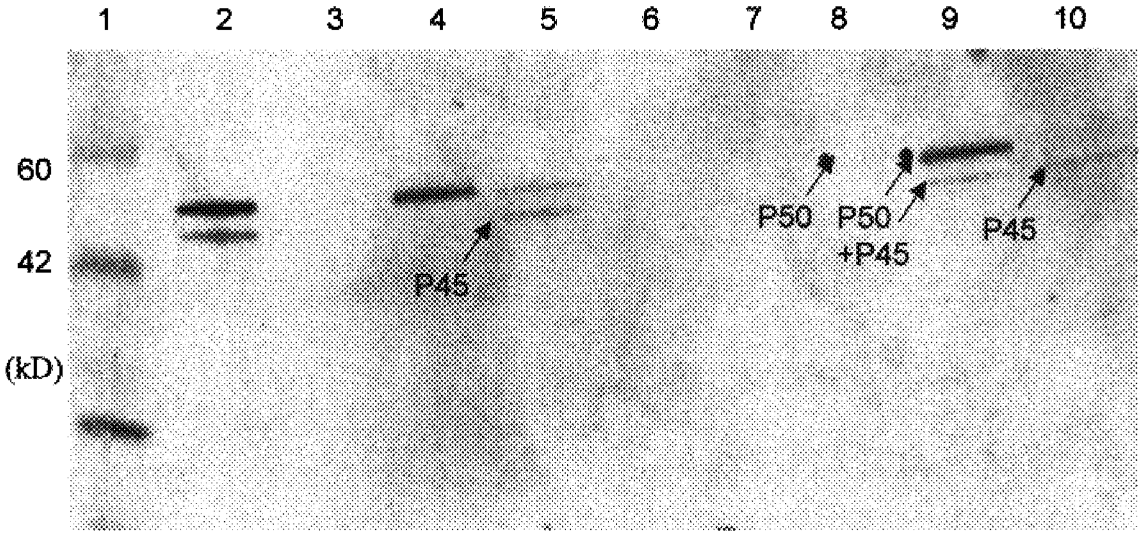
FIG. 9. S200-purified PEF (1.4 μg total protein) was heated at 85 or 100° C. prior to electrophoresis. Four slices were excised from the gel between the 60 kD (slice 1) and 42 kD (slice 4) markers. The proteins were eluted in 50 μl of buffer and 10 μl aliquots were boiled in the presence of SDS-BME loading dye and run out on 4–20% PAGE gels. Lane 1: Novex pre-stained markers; lane 2: 0.28 ng PEF; lanes 3–6: gel purified proteins isolated from S200-purified PEF heated at 85° C.-slice 1 (lane 3), slice 2 (lane 4), slice 3 (lane 5), and slice 4 (lane 6); lanes 7–10; gel purified proteins isolated from S200-purified PEF heated at 100° C.: slice 1 (lane 7), slice 2 (lane 8), slice 3 (lane 9), and slice 4 (lane 10).

Protein components of S200-purified PEF were purified by SDS-PAGE and the PCR enhancing titer was determined by adding serial dilutions of each gel slice eluate to PCR reactions with cloned *Pfu* DNA polymerase PCR reactions. The protein or protein mixtures which exhibited the highest levels of polymerase enhancing activity were identified by running the eluates on silver stained SDS-PAGE gels. FIG. 9 shows the proteins recovered from 4 gel slices between the 42 and 60 kD markers from 2 heated treated PEF samples. The greatest PCR enhancements were observed for protein samples run in lanes 5, 9, and 10. These lanes contained the highest amounts of P45, in addition to low but detectable amounts of P50. Relative P50 concentration did not necessarily correlate with highest PCR enhancing titer, as the proteins run in lane 4 (where only P50 is visible) exhibited a lower titer than the protein mixture in lane 5 (same amount of P50, plus P45). Moreover, samples in lanes 9 and 10 exhibited similarly high PCR enhancing titers and levels of P45, but the sample in lane 9 contained 10 to 1000-fold more P50 than the sample in lane 10. These results are consistent with P45 being the most active component of the PEF complex. Since all samples of P45 isolated to date contain varying concentrations of P50, the exact biochemical role a low concentration of P50 has on attaining full PEF activity or stability has not been determined.

EXAMPLE 5

Amino Acid Analysis of PEF Complex and P50 and P45 Components

Figure 10:
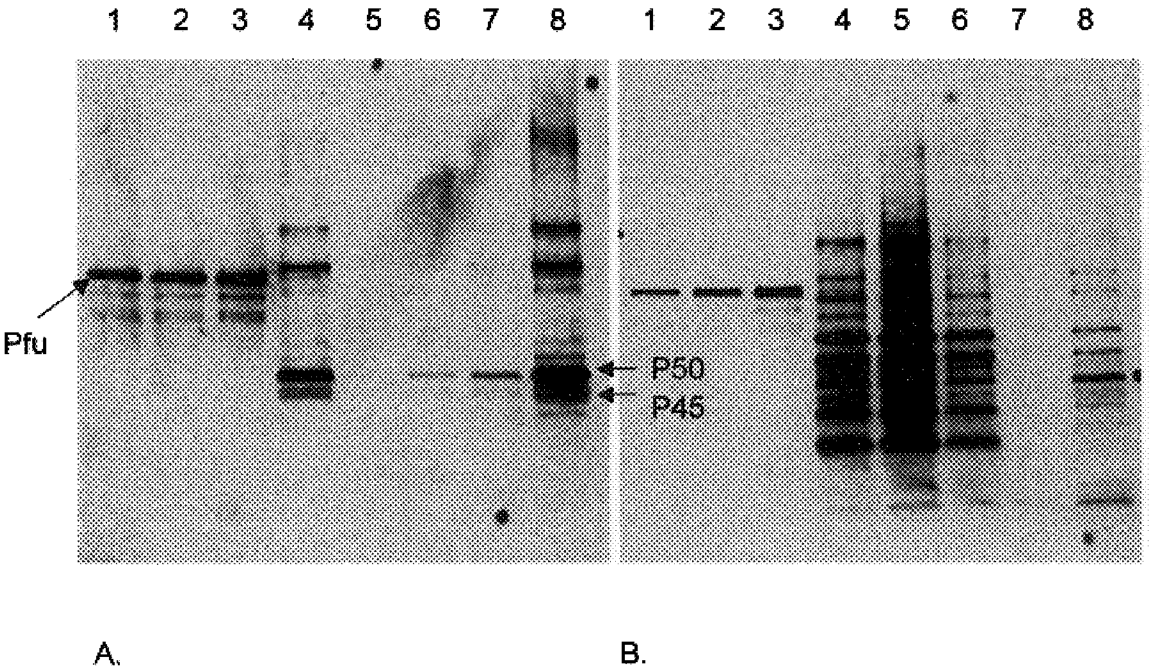
FIG. 10. SDS-PAGE analysis of *P. furiosus* PEF preparations. In left-handed panel, the following samples were subject to SDS-PAGE analysis, conducted as described cloned *Pfu* DNA polymerase lot#24A (56 ng/μl) [lanes 1–3, 1 μl, 2 μl, 4 μl]; S200 purified *P. furiosus* PEF fraction #46 (prep. 1 from SCS #38) [lane 4—2 μl]; S200 purified *P. furiosus* PEF pool fractions #47–48 (550 ng/μl; prep. 3 from SCS #38)[lanes 5–8, 0.1 μl, 0.2 μl, 0.4 μl, 1 μl]. In right-handed panel, the following samples were run: cloned *Pfu* DNA polymerase lot#24A (56 ng/μl) [lanes 1–3, 1 μl, 2 μl, 4 μl]; microcon 30-concentrated SCS #36 heparin sepharose fraction #78 (prep. 2) [lanes 4–6, 1 μl, 2 μl, 0.4 μl]; SCS #37 heparin sepharose fraction #75 (prep. 4) [lanes 7–8, 1 μl, 5 μl].
Figure 11:
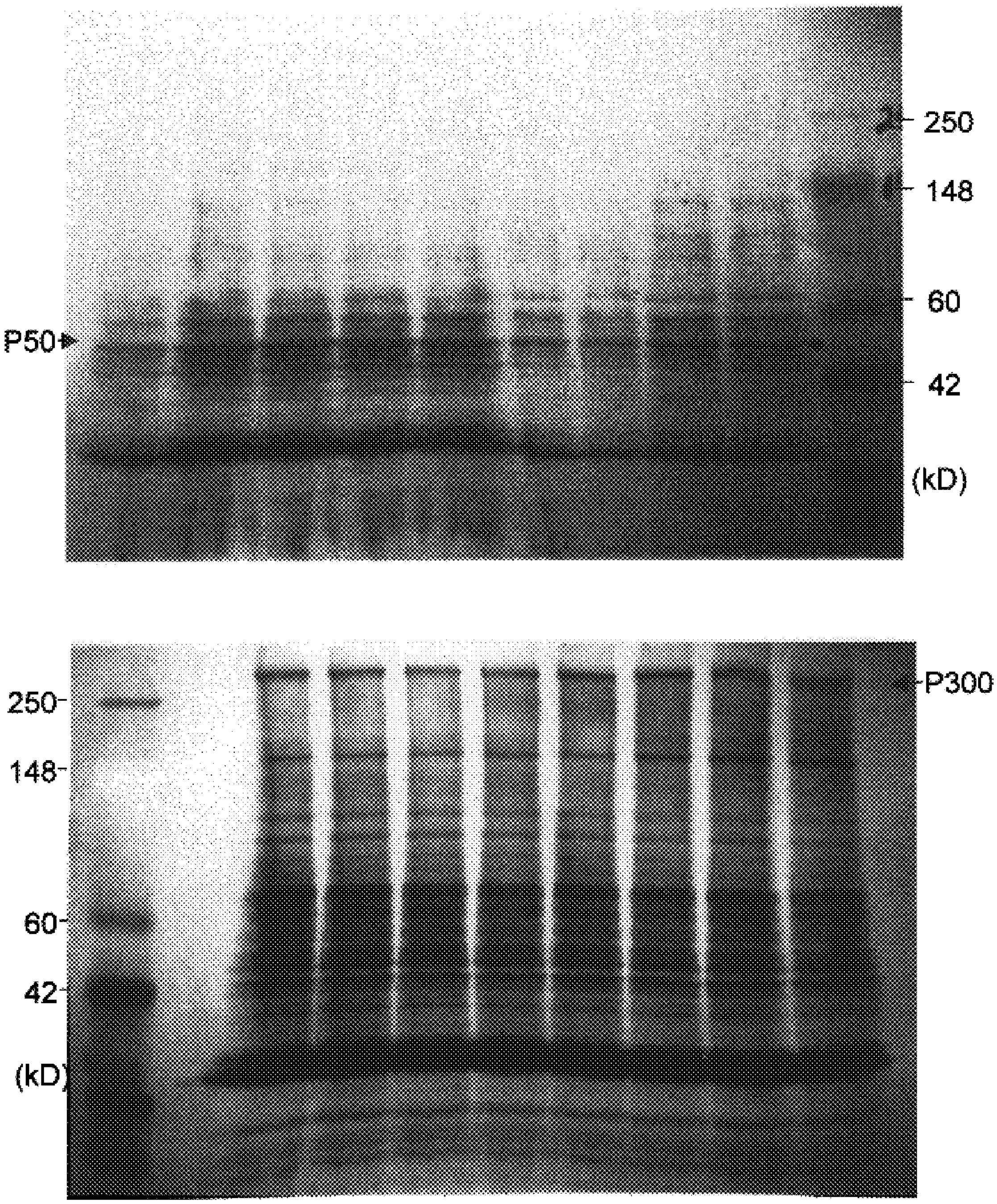
FIG. 11. PDVF blots of *P. furiosus* PEF. PEF-containing heparin sepharose fractions (from SCS #37 *Pfu* purification) were concentrated and aliquots electrophoresed in 8 or 9 lanes on 4–20% SDS-PAGE gels as described. The samples were boiled for 3 min. prior to loading to recover the 50 kD monomeric PEF (top) or were loaded in the absence of heat treatment to recover the >250 kD aggregate (bottom). The proteins were transferred to PDVF filters (BioRad) and stained with Amido black.

The complex and the predominate 50 kD component (P50) and 45 kD (P45) component from *Pfu* were sequenced at the N-terminus. In addition, N-terminal sequence analysis was performed on the minor 100 and 150 kD components generated upon heat dissociation. Two analyses were performed. In the first study, heparin sepharose-purified PEF samples (≈20% homogeneous; prep. 4 in FIG. 10) were electrophoresed and electroblotted onto PDVF filters. Samples were loaded onto 4–20% SDS-PAGE gels at room temperature or after heat treatment, to allow recovery of both the 50 kD protein and the >250 kD complex (FIG. 11). Blots were sent to Wistar Sequencing Facility (Philadelphia, Pa.) for analysis. N-terminal sequence analysis was performed on both the 50 kD (P50) protein (heated SDS-PAGE sample) and the >250 kD PEF complex (unheated SDS-PAGE sample).

The N-terminal amino acid sequences of the PEF complex (P300) and the 50 kD component (*Pfu* P50) were found to be substantially identical (Table 1). This data confirmed that *Pfu* P50 is the predominant component of the PEF complex. Two distinct sequences were found for both P300 and P50 (1° and 2°), suggesting that *Pfu* PEF may contain 2 different 50 kD species which co-migrate, or that the PVDF strip containing the 50 kD species was contaminated with the 45 kD species or other species visible by SDS-PAGE.

In addition to the N-terminal sequencing, the 50 kD protein was also subject to in situ trypsin digestion and microbore reverse HPLC. A subset of tryptic peptides was analyzed by mass spec. Two peptides with single masses (#107, #112) and one peptide with two masses (#108) were chosen for sequence analysis. Two internal peptide sequences from *Pfu* P50 were recovered (Table A; Tryptic Peptides). Peptide #112 was 24 amino acids in length and the calculated mass of the Edman sequence (2530.8) was in very good agreement with the observed peptide mass (2531.7). Peptides #107 and #108 contained multiple sequences which could not be sorted by Edman sequencing alone. However these peptide fractions eluted very close together on microbore HPLC and contained several residues in common. Based upon shared sequence and mass analysis, a tentative sequence was assigned (107/108; Table A).

TABLE A

Analysis 1.

N-terminal Sequencing

| Protein Sample | Mass (Da) Obs. | | Sequence/(SEQ ID NO: 1) | Comments |
|---|---|---|---|---|
| PEF complex | ≈50,000 | 1° | XLLHH VKLIY ATXXR | (1) |
| | | 2° | XXXPD WXXRX EXLXX | (2) |

TABLE A-continued

| Analysis 1. | | | | |
|---|---|---|---|---|
| P50 | ≈50,000 | 1° | MLLHH VKLIY ATKSR RLVGK KIVLA IPGXI AAVEP | (3) |
| | | 2° | XXXPD WSXRX EXLGE KFY | (4) |

Tryptic Peptides

| Peptide | Mass (Da) Obs. | Calc. | Sequence/(SEQ ID NO:) | | Comments |
|---|---|---|---|---|---|
| 107 | 1389.59 | N/A | | | multiple sequence |
| 108 | 1659.1, 1910.63 | N/A | | | multiple sequence |
| 107/108 | — | 1910.3 | KYDAV IMAAA VVDFR PK | (5) | AAs common to 107/108 |
| 112 | 2531.73 | 2530.8 | ADLVV GNTLE AFGSE ENQVV LIGR | (6) | |

"X" represents any amino acid underlined residues represent amino acids that may be substituted with any amino acid but are tentatively assigned as indicated The 35 amino acid sequence recovered from the N-terminus of *Pfu* P50 (SEQ ID NO: 3), and the two internal peptides of 17 and 24 amino acids (SEQ ID NO:s 5 and 6), represent approximately 16% of the total amino acid sequence of *Pfu* P50, assuming an apparent molecular weight of 50 kD and a length of approximately 454 amino acids.

Figure 12:
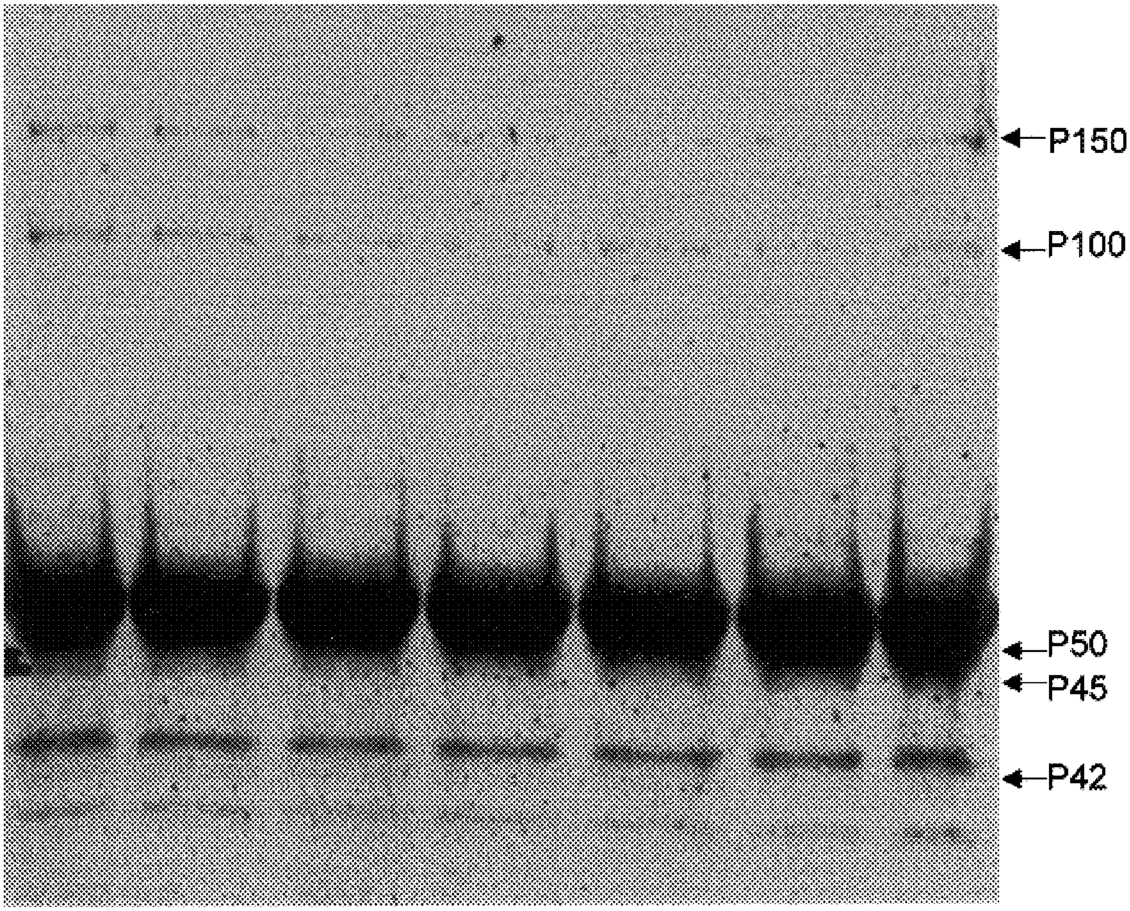
FIG. 12. PVDF blot of S200-purified *P. furiosus* PEF. Approximately 20 μg of total protein was electrophoresed in each of 7 lanes on a 12% PAGE gel. The samples were heated at 85° C. for 5 minutes prior to loading. The proteins were transferred to PVDF filters and stained as in the FIG. 11 legend.

In the second round of analyses, the N-terminal sequences of the 150, 100, 50, 45, and 42 kD species were determined from a PVDF blot of heated S200-purified PEF (FIG. 12, Table B). This analysis was performed by the Beckman Research Institute of the City of Hope (Duarte, Calif.). The N-terminal sequences of the 150 and 100 kD species were the same and identical to the major sequence in the 50 kD band (except for ambiguity at the N-terminus) and similar to the minor sequence in the 45 kD band. In addition, the sequence was very similar to the major sequence in the PEF complex and the 50 kD band determined in the Wistar sequence analysis. The data are consistent with the 150 and 100 kD species being alternative forms of the 50 kD species (e.g., dimers, trimers, or aggregates). The major N-terminal sequence of the 45 kD band (2 blot sections analyzed; "upper" and "lower") was distinct from the P50 sequence and very similar to the minor sequence found in the 50 kD bands analyzed by both Wistar and Beckman and in the PEF complex analyzed by Wistar. No N-terminal sequence was recovered for the 42 kD species. In total, these data are consistent with the PEF complex consisting of 2 distinct protein components, P50 and P45.

TABLE B

Analysis 2.

| Protein sample (MW) | | Sequence | (SEQ ID NO) |
|---|---|---|---|
| 150 kD | | (GAM)LHHV KLIYA TKLRK | (7) |
| 100 kD | | (GAM) LHHV KLIYA TK(KL)RK | (8) |
| 50 | 1° | M LHHV KLIYA TKL | (9) |
| | 2° | GL(KL)PD W(WK) (KF)RK EES | (10) |
| 45 (upper) | 1° | (GAI)LLPD WKIRK EILIE | (11) |
| | 2° | XMHH(VI) KLXYA TXSRK | (12) |

TABLE B-continued

Analysis 2.

| Protein sample (MW) | | Sequence | (SEQ ID NO) |
|---|---|---|---|
| 45 (lower) | 1° | M(LY) (LV) (RP)D WKRRK EILIE | (13) |
| 42 | no sequence | | |

X represents any amino acid;

underlined residues represent amino acids that may be substituted with any amino acid but are tentatively assigned as indicated.

Homology searches of the nonredundant GenBankCDS translations+PDB+SwissProt+SPupdate+PIR protein databases using BLASTp indicated that the partial amino acid sequence of *Pfu* P50 and P45 do not exhibit identity to any protein in those databases.

EXAMPLE 6

Nucleotide and Predicted Amino Acid Sequence of P50: Homology to *E. coli* DFP Flavoprotein The nucleotide sequence of the P50 protein component was obtained by cloning the *Pfu* P50 using standard techniques.

1. Library Screening

A *Pyrococcus furiosus* genomic library was plated on XL1-Blue MRF' *E. coli* at a density of approximately 2000 plaques per plate. Duralose filters (nitrocellulose on a nylon backing) were used to take replicate lifts from each plate. While the first filter was on the plate, orientation marks were made by stabbing a needle through the filter and into the plate. The orientation marks were marked in pen on the back of the plate before the filter was removed. The filter lifts were treated as follows:

| | |
|---|---|
| 1.5–2.0 minutes | 1.5 M NaCl, 0.5 M NaOH |
| 2 minutes | 0.5 M Tris (pH 8.0), 1.5 M NaCl |
| 30 seconds | 2xSSC, 0.2 M Tris (pH 7.5) |

After treatment, the filters were partially dried until they were still damp, but no standing water was visible. The DNA on the filters was fixed by UV crosslinking with the Stratalinker set to the "Autolink" format.

The filters were prehybridized in 15 ml of:

5×SSC 40 mM $NaPO_4$ pH (6.5)

5×Denhardt's

5% Dextran Sulfate

50% Formamide 0.1 mg/ml Salmon sperm DNA (Boiled separately and added immediately prior to use)

Prehybridization was carried out at 42° C. for approximately 2 hours.

Probe was generated from the 900 bp PCR product made from *Pfu* genomic DNA and the following primers:

```
Oligo #50:  CAT CAT GAA AAA CTA ATT TAC GC  (SEQ ID
               C   C   C   G T C            NO: 14)
                       T       T

Oligo #61:  GC CAT AAT TAC TGC ATC GTA TTT  (SEQ ID
                   G   C   G   G            NO: 15)
                   T   G   A
                       A
```

The PCR product was purified from free primers, buffer and nucleotides and 50 ng was labeled with $^{32}P$-αdATP using the Stratagene Prime-It II Random Primer Labelling kit. The probe was purified from free nucleotides before being boiled for five minutes and added to the prehybridization reaction. The total probe was roughly calculated to be 80 million cpm.

Hybridization was allowed to continue overnight at 42° C. before the hybridization solution was removed and the filters were washed four times with 0.1×SSC, 0.1% SDS at 60° C. (very stringent conditions).

The filters were exposed to X-ray film overnight and 20 primary isolates, with strong signals on both replicate filters were picked.

Six primary isolates were diluted, plated and screened again using the same method described above. Of the six, three filters produced isolated lambda clones. The clones were confirmed by PCR amplification using the degenerate primers. All clones were able to produce the 900 bp product with oligos #50 and #61 which had been used as probe. Clones of the 6A, and 3B screens were able to produce a 1200 bp fragment with oligos #54 and #58. Clones of the 6D screens were only able to produce the 900 bp product.

```
Oligo #54:  CAT CAT GAA AAA CTA ATA TAC GC  (SEQ ID
               C   C   C   G T C            NO: 16)
                       T       T

Oligo #58:  AG TAC TAC TTG ATT TTC TTC      (SEQ ID
             A G   G   C   G                NO: 17)
               A   A
```

Bluescript plasmid was excised from the lambda clones in SOLR cells and the presence of inserts confirmed again by PCR amplification of the 1200 or 900 bp product.

2. DNA Sequencing

Sequencing was carried out on purified PCR products, and plasmid mini-preps made from the excised cells. The nucleotide sequence is listed below with the predicted protein translation. The peptide sequence used to generate the probes are indicated by underlining. Protein sequence comparisons to the *Methanococcus jannaschii* pantothenate metabolism flavoprotein (dfp) and *E. coli* dfp indicates that the majority of the sequence is correct.

```
(SEQ ID NO: 18)
ATGCTTCACCACGTCAAGCTAATCTACGCCACAAAAAGTCGAAAGCTAGT

TGGAAAAAAGATAGTCNNNNNNNNNCCAGGGAGTATTGCGGCTTTGGATG

TGAAAGCTTGTGAGGGACTAATTAGGCATGGGGCCGAAGTTCATGCAGTG

ATGAGTGAGGCAGCCACCAAGATAATTCATCCTTATGCATGGAATTTGCC

CACGGGAAATCCAGTCATAACTGAGATCACTGGATTTATCGAGCATGTTG

AGTTAGCAGGGGAACATGAGAATAAAGCAGATTTAATTTTGGTTTGTCCT

GCCACTGCCAACACAATTAGTAAGATTGCATGTGGAATAGATGATACTCC

AGTAACTACAGTCGTGACCACAGCATTTCCCCACATTCCAATTATGATAG

CCCCAGCAATGCATGAGACAATGTACAGGCATCCCATAGTAAGGGAGAAC

ATTGAAAGGTTAAAGAAGCTTGGCGTTGAGTTTATAGGACCAAGAATTGA

GGAGGGAAAGGCAAAAGTTGCAAGCATTGATGAAATAGTTTACAGAGTTA

TTAAAAAGCTCCACAAAAAAACATTGGAAGGGAAGAGAGTCCTAGTAACG

GCGGGAGCAACAAGAGAGTACATAGATCCAATAAGATTCATAACAAATGC

CAGCAGTGGAAAAATGGGAGTAGCGTTGGCTGAAGAAGCAGATTTTAGAG

GAGCTGTTACCCTCATAAGAACAAAGGGAAGTGTAAAGGCTTTTAGAATC

AGAAAAATCAAATTGAAGGTTGAGACAGTGGAAGAAATGCTTTCAGCGAT

TGAAAATGAGTTGAGGAGTAAAAAGTATGACGTAGTTATTATGGCAGCTG

CTGTAAGCGATTTTAGGCCAAAAATTAAAGCAGAGGGAAAAATTAAAAGC

GGAAGATCAATAACGATAGAGCTCGTTCCNNNNAATCCCAAAATCATTGA
```

-continued

```
TAGAATAAAGGAAATTCAACCAAATGTCTTTCTTGTTGGATTTAAAGCAG

AAACTTCAAAAGAAAAGCTTATAGAAGAAGGTAAAAGGCAGATTGAGAGG

GCCAAGGCTGACTTAGTCGTTGGTAACACATTGGAAGCCTTTGGAAGCGA

GGAAAACCAAGTAGTATTAATTGGCAGAGATTTCACAAAAGAACTTCCAA

AAATGAAAAAGAGAGAGTTAGCAGAGAGAATTTGGGATGAGATAGAGAAA

TTNCTGTCC
```

*Pyrococcus furiousa* dfp predicted amino acid sequence:
(SEQ ID NO: 19)

```
MLHHVKLIYATKSRKLVGKKIVXXXPGSIAALDVKACEGLIRHGAEVHAV

MSEAATKIIHPYAWNLPTGNPVITEITGFIEHVELAGEHENKADLILVCP

ATANTISKIACGIDDTPVTTVVTTAFPHIPIMIAPAMHETMYRHPIVREN

IERLKKLGVEFIGPRIEEGKAKVASIDEIVYRVIKKLHKKTLEGKRVLVT

AGATREYIDPIRFITNASSGKMGVALAEEADFRGAVTLIRTKGSVKAFRI

RKIKLKVETVEEMLSAIENELRSKKYDVVIMAAAVSDFRPKIKAEGKIKS

GRSITIELVPXNPKIIDRIKEIQPNVFLVGFKAETSKEKLIEEGKRQIER

AKADLVVGNTLEAFGSEENQVVLIGRDFTKELPKMKKRELAERIWDEIEK

XLS
```

N-term Sequence correspondinq to probe:

```
      MLHHVKLIYATKSRKLVGKKIVXXXPGSIAA            (SEQ ID NO: 46)
```

Internal sequences corresppnding to probes:

```
      KYDVVIMAAAVSDFRPK                          (SEQ ID NO: 47)

      ADLVVGNTLEAFGSEENQVVLIGR                   (SEQ ID NO: 48)
```

The protein has a theoretical pl of 9.36 and a theoretical MW of 44801.29.

There are inconsistencies between the chemically-determined AA sequence of P50 and the AA sequence derived from the *P. furiosus* DFP genomic clone. One skilled in the art is familiar with many reasons for this type of inconsistency. For example, the inconsistencies below can, largely, be explained by known limitations common to the procedures used. These limitations do not operate to limit the structural knowledge of proteins or nucleic acids. Instead, they merely indicate possible variations in the sequences of amino acids or nucleic acids by a finite number. Some of the inconsistencies and explanations are:

```
MLLHHVKLIYA TKSRR LVGKK IVLAI PGXIA AVEP  (Table A; SEQ ID NO:s 1 and 3)

MLHHV KLIYA TKL                           (Table B; SEQ ID NO: 9)

MLHHV KLIYA TKSRK LVGKK IVLAI PGSIA ALDV  (predicted sequence)
```

The inconsistency in Table A sequence at cycle 2 (extra AA between AA1 and 2) may be due to contamination with P45, which appears to have L's at positions 2 and 3. Moreover, L at cycle 2 in SEQ ID NO: 1 was assigned tentatively. Other inconsistencies between the Table A sequence and the predicted sequence occur at AA 15 (R vs. K) and AA 32–34 (VEP vs. LDV).

An inconsistency between the Table B sequence and the predicted sequence was found at AA13. The identification of AA13 as L instead of S is explained by the poor recovery of S in chemical sequencing and the contamination of P50 with low amounts of P45, which has a L at that position.

| | |
|---|---|
| ADLVV GNTLE AFGSE ENQVV LIGR | (Table A; SEQ ID NO: 6) |
| ADLVV GNTLE AFGSE ENQVV LIGR | (predicted sequence) |
| KYDAV IMAAA VVDFR PK | (Table A; SEQ ID NO: 5) |
| KYDVV IMAAA VSDFR PK | (predicted sequence) |

SEQ ID NO: 6, determined chemically from a P50 tryptic peptide, was identical to a 24 AA sequence translated from the DFP DNA sequence. For SEQ ID NO: 5, there were 2 inconsistencies found between the chemical and DNA sequences. An A was recovered at cycle 4 instead of a V, and a V was recovered at cycle 12 instead of a S. The inconsistencies may be due to the difficulties associated with interpreting sequences from a sample that is not absolutely pure.

EXAMPLE 7

Identification of Related Proteins

1. DNA Sequence Homology of *Pfu* P50 Protein to Bacterial Proteins

The DNA sequence of a P50 clone exhibits very strong homology to the flavoprotein DFP, a protein identified in *E.*

*coli* as playing a role in DNA synthesis and pantothenate metabolism (Spitzer and Weiss, J. Bacteriol. 164:994–1003 (1985) and Spitzer, Jimenez-Billini, and Weiss, J. Bacteriol. 170:872–876 (1988)). Although DFP was found to be an essential gene for DNA replication, these authors were not able to elucidate its role in DNA replication. The sequences in Table 1 (N-terminal 1° sequence, tryptic peptides 107/108 and 112) are all found in the translated P50 clone, which exhibits very high homology to DFP. Accordingly, the P50 amino acid and DNA sequence information can be used to identify related proteins associated with PEF complexes from other sources such as bacteria.

The amino acid sequences of *Methanococcus jannaschii* (Mja) (SEQ ID NO.: 51) and *E. coli* (SEQ ID NO.: 52) dfp proteins support the identification of the protein designated P50 (*Pfu*) (SEQ ID NO.: 19) as a member of the dfp family of proteins. The three protein sequences were compared using ClustalW 1.6 with the comparison data represented below.

```
        1             15 16             30 31             45 46             60 61             75 76             90

1       -----------MLHH VKLIYATKSRKLVGK KIVXXXPGSIAALDV -KACEGLIRHGAEVH AVMSEAATKIIHPYA WNLPTGNPVITEITG   78
Pfu

2       -------MISEIMHP TKLLKGTKSKLLENK KILVAVTSSIAAIET PKLMRELIRHGAEVY CIITEETKKIIGKEA LKFGCGNEVYEEITG   83
Mja

3 E.    MKARQQKYCDKIANF WCHPTGKIIMSLAGK KIVLGVSGGIAAYKT PELVRRLRDRGADVR VAMTEAAKAFITPLS LQAVSGYPVSDSLLD   90
coli

Page
2.1
        91            105 106           120 121           135 136           150 151           165 166           180

1       -----FIEHVELAGE HENKADLILVCPATA NTISKIACGIDDTPV TTVVTTAFPHIPIMI APAMHETMYRHPIVR ENIERLK-KLGVEFI  162
Pfu

2       -----DIEHILLY-- --NECDCLLIYPATA NIISKINLGIADNIV NTTALMFFGNKPIFI VPAMHENMFN--AIK RHIDKLKEKDKIYII  162
Mja

3 E.    PAAEAAMGHIELG-- --KWADLVILAPATA DLIARVAAGMANDLV STICLATP--APVAV LPAMNQQMYRAAATQ HNLEVLA-SRGLLIW  173
coli

Page
3.1
        181           195 196           210 211           225 226           240 241           255 256           270

1       GPRIEE------GKA KVASIDEIVYRVIKK LHKKTLE-GKRVLVT AGATREYIDPIRFIT NASSGKMGVALAEEA DFRGAVTLIRTKGSV  245
Pfu

2       SPKFEE------GKA KVANIEDVVKAVIEK IGNNLKKEGNRVLIL NGGTVEFIDKVRVIS NLSSGKMGVALAEAF CKEGFYVEVITAMGL  246
Mja

3 E.    GPDSGSQACGDIGPG RXXDPLTIVDMAVAH PSPVNDLKHLNIMIT AGPTREPLDPVRYIS NHSSGKMGFAIAAAA ARRGANVTLVSGPVS  263
coli

Page
4.1
        271           285 286           300 301           315 316           330 331           345 346           360

1       KAFRIRKIKLKVETV EEMLSAIENELRSKK YDVVIMAAAVSDFRP KIKAEGKIKSGRS-- --ITIELVPXNPKII DRIKEIQPN-VFLVG  330
Pfu

2       EPPYYIKNHKVLTAK EMLNKAIE--L-AKD FDIIISSAAISDFTV ES-FEGKLSSEEE-- --LILKLKR-NPKVL EELRRIYKD-KVIIG  326
Mja

3 E.    LPTPPFVKRVDVMTA LEMEAAVN--ASVQQ QNIFIGCAAVADYRA ATVAPEKIKKQATQG DELTIKMVK-NPDIV AGVAALKDHRPYVVG  350
coli

Page
5.1
        361           375 376           390 391           405 406           420 421           435 436           450

1       FKAETSK-EK-LIEE GKRQIERAKADLVVG NTL----EAFGSEEN QVVLIGRDFTKELPK MKKRELAERIWDEIE KXLS-------      403
Pfu

2       FKAEYNLDEKELINR AKERLNKYNLNMIIA NDLSK--HYPGDDYI EVYIITKYEVEKISG SKK-EISERIVEKVK KLVKS----        403
Mja

3 E.    FAARTNN----VEEY ARQKRIRKNLDLICA NDVSQPTQGFNSDNN ALHLFWQDGDKVLPL ERKELLGQLLLDEIV TRYDEKNRR        430
coli
```

From the above comparison, it would be apparent to one of skill in the art that related proteins from other species can be identified and isolated by methods known in the art. For example, the example above employed very stringent screening conditions. A less stringent condition, varying the concentration of salts, detergent, or the temperature during hybridization or washing, as known in the art, would lead to related clones from libraries containing sequences of any of a number of species. For example, in addition to the conditions described above, any of the following hybridization conditions can be used, in any combination, in methods to isolate DNA sequences related to the P50 or P45 sequences herein:

- low stringency wash in a solution comprising approx. 0.45 M NaCl, approx. 0.045 M trisodium citrate, and approx. 0.1% SDS, at approx. 37° to approx. 42° C.;
- hybridization buffer comprising approx. 0.75M NaCl, approx. 0.15 M Tris, approx. 10 mM sodium pyrophosphate, approx. 0.075 M trisodium citrate, and approx. 50% formamide;
- hybridization buffer comprising approx. 5×SSC, approx. 5×Denhardt's, approx. 5% Dextran Sulfate, approx. 50% formamide, and approx. 0.1 mg/ml ssDNA;
- hybridization wash comprising approx. 0.1 M phosphate, approx. 0.1×SET, approx. 0.1% sodium pyrophosphate, and approx. 0.1% SDS at approx. 45° C.

2. Absorbance Spectrum of Purified *Pfu* PEF Complex

Figure 13:
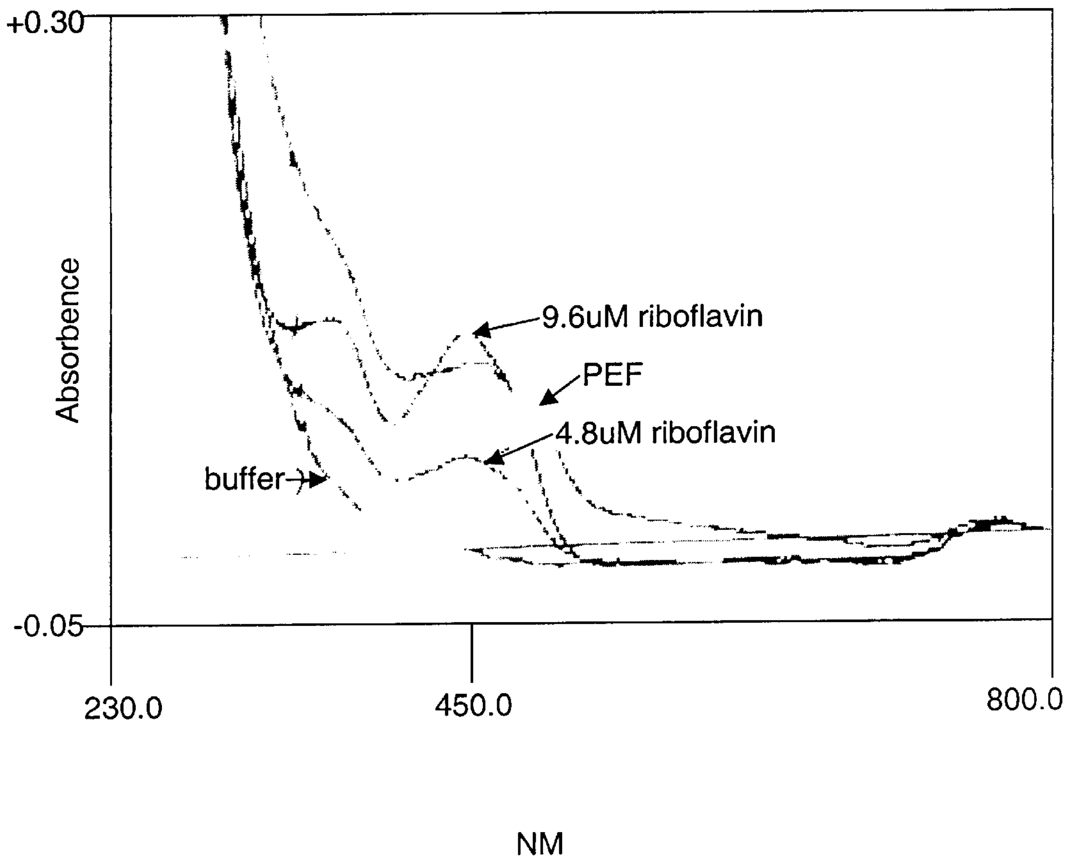
FIG. 13. Absorbance spectrum of S-200 purified *P. furiosus* PEF. The spectra of the following were obtained on a Shimadzu UV160 U spectrophotometer: 0.7 mg/ml *P. furiosus* PEF, 9.6 μM and 4.8 μM riboflavin, and PEF final storage buffer (blank).

The absorbance spectrum of purified *P. furiosus* PEF complex reveals two peaks of absorbance at 370 and 450 nm. FIG. 13 depicts the absorbance spectrum of S-200 purified *P. furiosus* PEF. These data indicate and are consistent with PEF complex comprising at least one flavoprotein. Sequencing data also verify the identification of *Pfu* P50 as a homolog of the *E. coli* DFP protein. *E. coli* DFP is a flavoprotein containing a non-covalently associated FMN moiety.

Up to this point, flavoproteins have not been directly implicated as part of the replication machinery. The involvement of a flavoprotein in PCR enhancement suggests a role for redox reactions. The only redox reaction involved in DNA synthesis is the formation of deoxyribonucleotides from ribonucleotides, which is catalyzed by ribonucleoside diphosphate reductase. In vitro, the ribonucleoside diphosphate reductase enzyme can be coupled to NADPH via two known pathways involving FAD-containing oxidoreductases (Pigiet and Conley, J. Biol. Chem. 252:6367–72 (1977); Thelander and Reichard, Ann. Rev. Biochem. 48:133–158 (1979)). One pathway involves thioredoxin and thioredoxin reductase. Interestingly, *E. coli* thioredoxin has been shown to act as an accessory protein and confer processivity on T7 DNA polymerase. An alternate hypothesis for the role of a flavoprotein in PCR enhancement is that a flavoprotein may be required for the continuous processing or activation of other proteins or cofactors needed for nucleic acid replication.

EXAMPLE 8

Nucleotide and Amino Acid Sequence of P45

The nucleotide sequence of the *Pfu* P45 protein component was obtained as described below.

1. Synthesis of P45 Sequences

Amino terminal peptide sequencing of purified P45 protein allowed the generation of four degenerate oligonucleotides:

```
#743:   CCA GAC TGG AAA ATA AGG AAA GA    (SEQ ID
             T         G TGG              NO: 32)
                         C
                         T

#744:   CCA GAC TGG AAA ATA AGA AAA GA    (SEQ ID
             T         G TGG              NO: 33)
                         C
                         T

#745:   CCA GAC TGG AAA ATA AGG AAG GA    (SEQ ID
             T         G TGG              NO: 34)
                         C
                         T

#746:   CCA GAC TGG AAA ATA AGA AAG GA    (SEQ ID
             T         G TGG              NO: 35)
                         C
                         T
```

A Lambda phage *Pfu* genomic library was used as template for PCR amplification of the P45 sequence. The four degenerate oligonucleotides were used in separate reactions to prime template in one direction, in combination with one of the primers that border the genomic insertion of the Lambda vector (−20 primer, and reverse primer). The PCR reaction was carried out as specified below:

10 μl 10×Stratagene cloned *Pfu* buffer
5 μl degenerate p45 primer (either 743, 744, 745 or 746) at 100 ng/μl
2.0 μl either reverse or −20 primer (100 ng/μl)
0.8 μl 100 mM dNTP
0.5 μl Taq DNA polymerase (Stratagene, 5 u/μl)
0.5 μl Taq Extender (Stratagene, 5 u/μl)
3.0 μl *Pfu* genomic library (~$1.2 \times 10^{10}$ plaque forming units/ml)
78.2 μl $H_2O$ One cycle at 95° C. for 3 minutes, followed by 30 cycles of: 95° C. for 1 minute; 51° C. to 65° C. gradient for 2 minutes; 72° C. for 6 minutes.

The PCR products were separated on a 1% agarose, 1×TBE, gel. All primer combinations produced multiple bands. A pattern of four bands was consistently seen with primers 743, 744, and 746 in conjunction with the −20 primer. The three degenerate primers that formed consistent four band patterns with the −20 primer were able to generate the pattern at 56° C. Only primer 743 could generate the pattern at 58° C. The band pattern produced with the degenerate primers in combination with the reverse primers was less distinct and formed only at lower annealing temperatures than the products generated with the −20 primer.

2. Cloning Strategies

Two strategies were used to isolate the P45 clone. One procedure was to make simplified sub-libraries of the original highly complex library and screen for an insert with the −20 and 743 primers. Positive sub-libraries could be diluted and rescreened until individual plaques containing the appropriate insert were identified. The other technique was to make use of Vectorette™ technology (Genosys Biotechnologies), which allows PCR amplification when the sequence of only one end of a DNA fragment is known. In the vectorette system, genomic DNA is digested with a selection of specific restriction endonucleases. After digestion, the ends of the genomic DNA are ligated to specific vectorette units, which have the same cohesive termini as the genomic DNA digestion. The ligated vectorette unit contains a sequence complimentary to a provided vectorette PCR primer. (Amold and Hodgson, PCR Methods and Applications 1: 39–42 (1991).)

3. The Vectorette Reaction

Fifty μl reactions containing 100 ng of *Pfu* genomic DNA were digested with Eco RI, Hind III and Bsp 1061 (an isoschizomer for Cla I) in their recommended buffers for one hour at 37° C. Without any post-reaction treatment, 1 µl of the appropriate vectorette unit (Hind III, Cla I or Eco RI at 3 pmole/µl) was added with 6 µl of 10 mM ATP, 1 µl of 100 mM DTT and 1 unit of T4 DNA ligase (Stratagene 4 u/µl). The reaction was cycled at the following temperatures: 20° C. for 60 minute followed by 37° C. for 30 minutes for 3 cycles.

The ligated DNA was amplified according to the following:

10 µl cloned 10×Stratagene *Pfu* buffer
8.3 µl degenerate p45 primer at 100 ng/µl
2.0 µl 50 pmol/µl vectorette primer
0.8 µl 100 mM dNTP
0.5 µl Taq DNA polymerase (Stratagene, 5 u/lµl)
0.5 µl Taq Extender (Stratagene, 5 u/µl)
1.0 µl vectorette library
76.9 µl H$_2$O One cycle at 95° C. for 1 minute followed by 30 cycles of: 95° C. for 1 minute; 56° C. for 2 minutes; and 72° C. for 3 minutes.

Ten µl were loaded on an 1% agarose, 1×TBE, gel. Multiple bands were produced by all primers except 745. To determine if all three vectorette library products had been correctly primed off the same target DNA (P45 sequence) rather than having been produced by a non-specific PCR reaction, the products were digested with Mnl I. Mnl I cleaves at a frequent four base pair recognition sequence and produces a useful pattern of bands specific to the template digested. The pattern generated by electrophoresis of the Mnl I digestion fragments of the Cla I/743, Hind III/744 and Eco RI/744 PCR products on a 6% acrylamide gel showed some variation, but the majority of bands could be identified in all three samples, indicating that they share large segments of identical sequence.

Screening

The PCR products from the Cla I/743 and Hind III/744 combinations were mixed and purified from free nucleotides and unused primers before being used as template for the generation of a 52 million cpm $^{32}$P labeled probe. Details on probe synthesis and library screening are cited in Example 6.

More than 60 positive clones resulted from screening with the mixed vectorette probe. Several positive were well situated for collection without significant contamination from adjoining plaques. Twelve of these plaques were subjected to PCR amplification with the 743 and −20 primer as described previously except that an annealing temperature of 56° C. was used instead of a temperature gradient. In the same amplification assay, 11 sub-libraries were assayed in the same manner.

Three of the twelve clones recovered from the primary radioactive label screen produced strong, single bands. Clone 1 produced a band of approximately 5 kb, clone 3 produced a band of approximately 3.5 kb, and clone 9 generated a band of approximately 2.7 kb. One of the sub-libraries also produced a clone of approximately 6.5 kb.

4. Sequencing

The positive PCR products were purified and sequenced with the Stratagene Exo⁻*Pfu* Cycle Sequencing kit. The degenerate primer 743 was used as a sequencing primer. All four PCR products produced identical sequencing ladders. The sequence from clone 9 is listed below.

```
  1 cagagtgggc agagaggctn ttgttaaggg gaaattaatc gacgtggaaa  (SEQ ID NO: 36)
 51 aggaaggaaa agtcgntatt cctccaaggg aata
```

Possible translations for this sequence including:

```
>clone9, frame+3
EWAERLLLRGN*SKWKRKEKSXFLQGN          (SEQ ID NO: 37)

>clone9, frame+2
RVGREAXVKGKLIEVEKEGKVXIPPRE          (SEQ ID NO: 38)

>clone9, frame+1
QSGQRGXC*GEINRSGKGRKSRYSSKGI         (SEQ ID NO: 39)
```

From this sequence, two forward primers and their complements were synthesized and used to sequence both purified PCR products and plasmid excised from the positive lambda clones with both Exo⁻*Pfu* cycle sequencing and ABI dye termination sequencing. The sequence generated from a primer 904, which went back towards the beginning of the gene, produced the following sequence:

```
  1 ctgcccactc tgaggtcata acctgctggt tggagccatt cttcagaaaa  (SEQ ID NO: 40)
 51 tggctctata agtatttctt ttctgatttt ccagtctgga agtagcattt
101 taccaccgaa acctttattt ttaatttaa
```

Since this sequence was generated from a plasmid template, the sequence will be unaffected by alterations which may occur in a PCR generated template. When the inverse compliment of this sequence is translated in the third frame the following protein sequence is generated (SEQ ID NO: 41):

```
                * IKNKGFGGKMLLPDWKIRKEILIEPFSEEWLQPAGYDLRVG
                                  ^
                               P45 Start
```

This sequence matches the amino acid sequence used to formulate the degenerate primers.

Sequence produced by the forward primers are represented here by the sequence from clone 3 with primer 903, as follows (SEQ ID NO: 42):

```
  1 TCCTCCAAGG GAATACGCCT TAATCCTAAC CCTCGAGAGG ATAAAGTTGC
 51 CCGACGATGT TATGGGGGAT ATGAAGATAA GGAGCAGTTT AGCAAGAGAA
101 GGGGTTATTG GTTCTTTTGC TTGGGTTGAC CCAGGATGGG ATGGAAACTT
151 AACACTAATG CTCTACAATG CCTCAAATGA ACCTGTCGAA TTAAGATATG
201 GAGAGAGATT TGTGCAGATC GCATTTATAA GGCTAGAGGG TCCGGCAAGA
251 AACCCTTACA GAGGAAACTA TCAGGGGAGC ACAAGGTTAG CGTTTTCAAA
301 GAGAAAGAAA CTCTAGCGTC TTTTCAATAG CATCCTCAAT ATCTCGTGTG
351 AAGTAATCAA TGTAAATACT TGCTGGGTGG GTTTTTAGGG ATTCAAACTC
401 GTAAGATGGG CCTGTATAGC AGAAAACTAT TTTTGCCTCT TCTTCATTTA
451 TCTTTCTGTG AATAAAAAAT CCAACATCCA CACTAGTTCC AAAAGATATT
501 GTTTGCGTGA TTACCAACAA GATCTTGGCA TTATTTTTGA TCTTATACTC
551 TATTCTCCTT TCTCCCTCCA ATTTGCCCAA AATAAACCTG GGTAGTATAC
601 ATTCACTCCT CTCTTTTAAA TTCCTATAAA TTCGTACATA GTTTAGAAAA
651 ATGTCAAATT CTTTNTTCCC TGTTAAATTA ACCNCNAAAT CTTTATNANN
701 AANCTTTTTA TAATTCCCAA AACCCCTAAT TTTCCCCTTN
```

Possible translations for this sequence include:

>frame+3 (SEQ ID NO: 43)

LQGNTP*S*PSRG*SCPTMLWGI*R*GAV*QEKG LLV-LLLGLTQDGMET* H*CSTMPQMNLSN*DMERDLCRSHL*G*RVRQE TLTEETIRGAQG*RFQR ERNSSVFSIASSISRVK*SM*ILAGWVFRDSNS*D GPV*QKTIFASSSFI FL*IKNPTSTLVPKDIVCVITNKILALFLILYSILLS PSN-LPKINLGSIH SLLSFKFL*IRT*FRKMSNSXFPVKLTXKSLXXXF L*FPKPLIFPX

>frame+2 (SEQ ID NO: 44)

PPREYALILTLERIKLPDDVMGD-MKIRSSLAREGVIGSFAWVDPGWDGNL TLMLYNAS-NEPVELRYGERFVQIAFIRLEGPARN-PYRGNYQGSTRLAFSK RKKL*RLFNSILNISCEVINVNTCWVGF*GFKLVR WACIAENYFCLFFIY LSVNKKSNIHTSSKRYCL-RDYQQDLGIIFDLILYS PFSLQFAQNKPG*YT FTPLF*IPINSYIV*KNVKFFXPC*INXXIFXXXLFI IPK-TPNFPL

>frame+1 (SEQ ID NO: 45)

SSKGIRLNPNPREDKVARRCYGGYEDKEQFSKRRG YWFFCLG*PRMGWKL NTNALQCLK*TCRIKIWREICADRIYKARGSGKKP LQRKLSGEHKVSVFK EKETLASFQ*HPQYLV*SNQCKYLLGGFLGIQTRK MGLYSRKLFLPLLHL SFCE*KIQHPH*FQKILFA*LPTRSWHYF*SYTLFS FLPPICPK*TWVVY IHSSLLNSYKFVHSLEKCQILXSLLN*PXNLYXXX FYNSQNP*FSP

When the P45 DNA sequence is translated in all six frames and compared to multiple sequence databases using the program Blastx, the dCTP deaminase gene of *Desulfurolobus ambivalens* was found to have similarities. Another entirely different gene was also identified, Visna virus and Maeda/Visna virus pol polyprotein, but at a less significant level of sequence similarity. Each of these similar genes, as well as those discussed below, may represent sequences related to P45 and, thus, may be used to develop further P45 DNA sequences in accordance with this invention as discussed in Example 9.

EXAMPLE 9

Identification of Related Proteins

1. DNA Sequence Homology of *Pfu* P45 Protein to dCTP Deaminase

The partial DNA sequence of the P45 clones exhibited very strong homology to deoxycytidine triphosphate deaminase (DCD or dCTP deaminase). dCTP deaminase is a homotetramer, which catalyzes the formation of dUTP and $NH_3$ from dCTP. dCTP deaminase has been discovered in two bacterial (*E. coli, Salmonella typhimurium*) and two archeal (*Desulfurolobus ambivalens, Methanococcus jannaschii*) species (Ouzounis, C., Kyrpides, N., and Sander, C. Nucl. Acids Res. 23:565–570 (1995); Bult, C. J. et al. Science 273:1058–1073 (1996); Beck, C. J., Eisenhardt, A. R. and Neuhard, J., J. Biol. Chem. 250:609–616 (1975)). *E. coli* DCD exhibits an apparent molecular weight of 21.2 kD (Wang, L. and Weiss, B. J. Bacteriol. 174:5647–5653 (1992)), while the predicted molecular weight of *M. jannaschii* DCD is approximately 22 kD (204 amino acids). These molecular weights are approximately half the apparent molecular weight of *P. furiosus* P45 and suggest that the heat-dissociated form of P45 (apparent mol. weight of 45 kD) may actually be a dimer.

The translated amino acid sequence of *P. furiosus* P45 reveals the presence of a putative uridine-binding motif conserved in ψ synthetases, dCTP deaminases, and dUTPases (Koonin, E. V. Nucl. Acids Res. 24:2411–2415 (1996)). In the following comparisons, U represents a bulky hydrophobic residue such as I, L, V, M, F, Y, or W, and the bolded residues match the G or U residues of the consensus sequence.

Consensus uridine-binding motif: .GUUD..U.G.U.U (SEQ ID NO: 53)

*P. fur.* P45: FAWVDPGWDGNTLM (SEQ ID NO.: 54)

*M. jann.* DCD: AGWIDAGFKGKITL (SEQ ID NO.: 55)

*M. jann put.* DCD: SAVHDPGYEGRPEY (SEQ ID NO.: 56)

*D. sulf.* DCD: PTIVDAGFEGQLTI (SEQ ID NO.: 57)

*E. coli* DCD: AHRIDPGWSGCIVL (SEQ ID NO.: 58)

The physiological function of dCTP deaminase has only been studied in *E. coli*, where it plays an essential role in deoxyribonucleotide metabolism. dCTP deaminase converts dCTP to dUTP, which is an obligatory step in the de novo synthesis of thymidylate in bacteria (Taylor, A. F., and Weiss, B. J. Bacteriol. 151:351–357 (1982)). In turn, uridine triphosphatase (dUTPase), a ubiquitous enzyme found in bacteria, eukaryotes, and eukaryotic viruses, degrades dUTP to pyrophosphate and dUMP, the thymidylate synthetase substrate. Thus, dCTP deaminase and dUTPase are functionally linked, with mutations in the dcd gene suppressing dut mutations (Wang, L. and Weiss, B. J. Bacteriol. 174: 5647–5653 (1992)).

dUTPase has shown to be an essential gene in *E. coli* and in yeast (El-Hajj, H. H., Zhang, H., and Weiss, B. J.

Bacteriol. 170: 1069–1075 (1988); Gadsden, M. H., et al. EMBO J. 12:4425–4431 (1993)) because it functions in vivo to prevent dUTP incorporation into DNA. In *E. coli* dut mutants, the dUTP pool is greatly enhanced, resulting in an increased substitution of uracil for thymine in DNA during replication. Uracil-DNA glycosylase and exonuclease III play an essential role in repairing uracil-containing DNA in *E. coli* dut mutants (Taylor, A. F. and Weiss, B. J. Bacteriol. 151:351–357 (1982)).

The physiological role of dCTP deaminase has not been characterized in archea. The exact role of dCTP deaminase in enhancing the performance of *Pfu* DNA polymerase in PCR is not clear from the metabolic studies on *E. coli* DCD. *P. furiosus* DCD may be playing a role in maintaining dNTP pools during PCR. For example, DCD may convert dUTP, generated during PCR by spontaneous deamination of dCTP (Lindahl, T. and Nyberg, B., Biochem. 13: 3405–3410 (1974)), back to dCTP to maintain balanced levels of each nucleotide. Alternatively, DCD may be playing a role in repairing uracil-containing DNA. To that end, Lasken et al. (J. Biol. Chem. 271:17692–17696 (1996)) reported that archeal DNA polymerases, including *Pfu* DNA polymerase, tightly bind uracil-containing DNA, while pol I (Family A) DNA polymerases do not. These investigators proposed that archeal DNA polymerases may play a role in recognizing and repairing uracils in vivo. DCD may be contributing to this repair process, thereby exhibiting a physiological role unique to archeal dCTP deaminases.

Accordingly, P45 proteins and complexes comprising them may also be used in DNA repair reactions. In addition, P45 proteins and complexes comprising them may be used where a uridine-binding reagent can be employed.

EXAMPLE 10

Production of Antibodies to PEF and Western Blot Analysis

1. Production of anti-PEF IgG.

Figure 14:
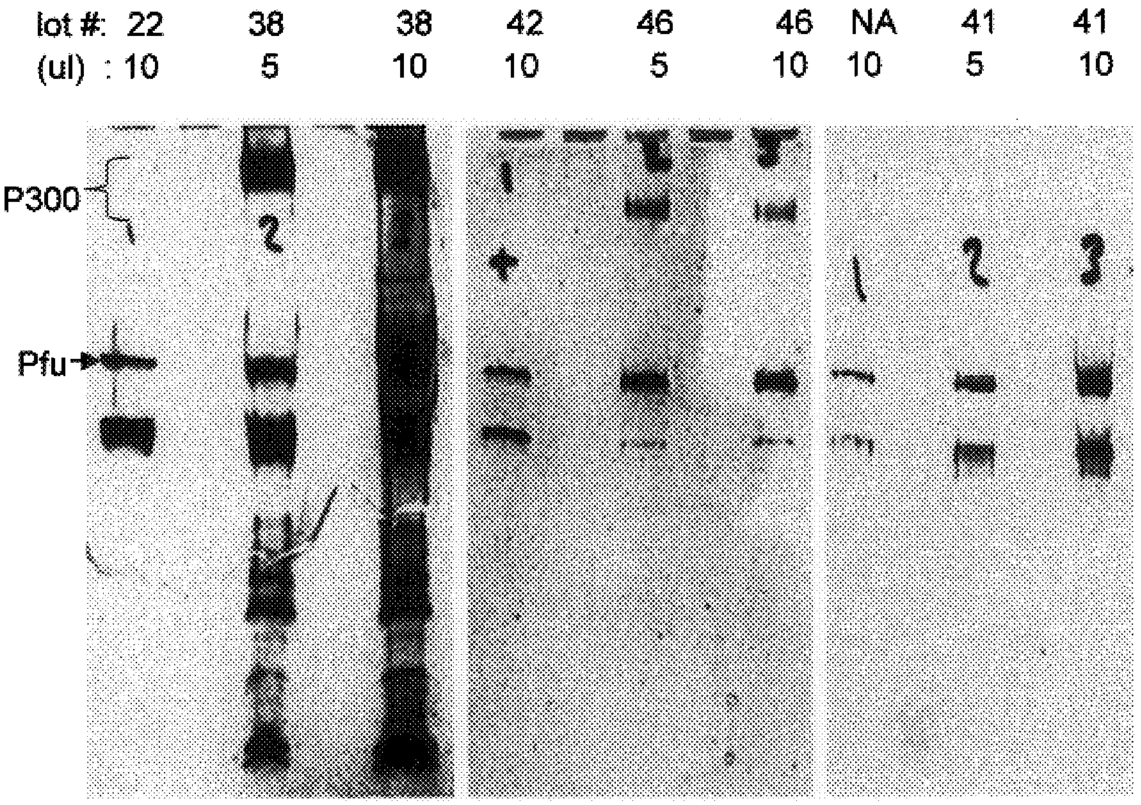
FIG. 14. Presence of PEF in *P. furiosus* DNA polymerase preparations. SDS-PAGE analysis is shown for six preparations of native *Pfu* DNA polymerase with varying levels of PEF present. The volumes of each lot loaded is indicated (μl). The protein samples were not boiled prior to electrophoresis.

PEF-specific IgG was purified by immunoaffinity chromatography from the sera of rabbits previously immunized against a lot of native *Pfu* DNA polymerase containing PEF (see FIG. 14). The S-200-purified *Pfu* PEF was covalently coupled to AffiGel 10 (BioRad: Hercules, Calif.) in the presence of 20 mM HEPES, 1 mM DTT, 50 mM KCl, 0.05% Tween 20, 1 mM EDTA, and 10% glycerol, following the manufacturer's recommended protocol. Rabbit sera (2.4 ml) was loaded onto a 0.2 ml column in the presence of 10 mM Tris (pH 7.5). The column was washed extensively and the specific IgG was eluded with 0.1M glycine-HCl (pH 2.5) followed by 0.1M triethylamine (pH 11.5). Using a Centricon-30, the IgG was concentrated and the elution buffer replaced with PBS.

2. Western Blot Analysis Using anti-PEF Antibodies.

Cell extracts were prepared by suspending cells in 4×50 mM Tris, pH 8.2, 10 mM BME, 1 mM EDTA, and 10% glycerol, followed by sonication. Then, 2.5 mM PMSF was added and the cellular debris removed by centrifugation for 15 minutes at 14,000 rpm. PEI was added to the supernatant to a final concentration of 0.9% and the mixture centrifuged again. The supernatants (10 $\mu$l) were electrophoresed on 4–20% SDS-PAGE gels and the proteins transferred to nitrocellulose by electroblotting. The blots were blocked with 1% Blotto/PBS for 1 hour at room temperature and then incubated with PEF-specific IgG overnight at 4° C. The blots were washed in PBS-0.05% Tween 20 and subsequently developed with alkaline phosphatase conjugated goat anti-rabbit IgG and NBT/BCIP substrates.

Figure 15:
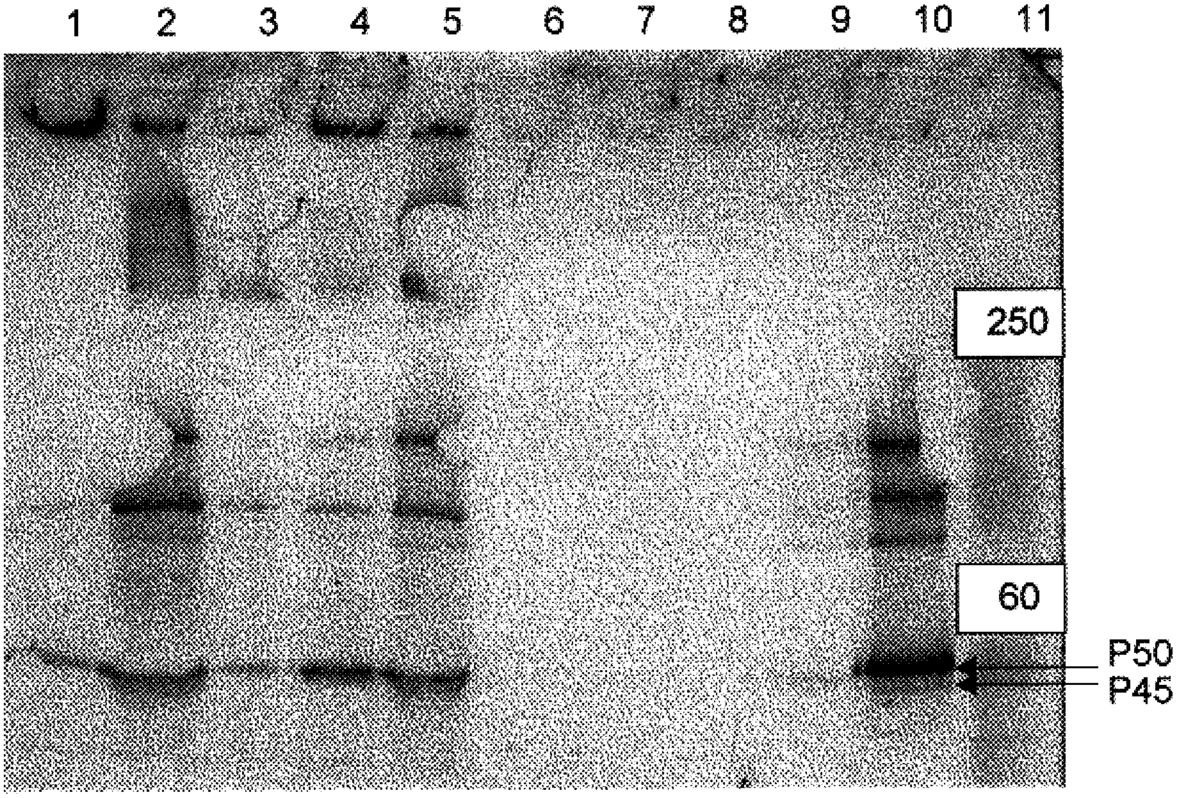
FIG. 15. Western blot analysis of crude extracts using *P. furiosus* PEF-specific IgG. Extracts were prepared from 5 different fermentations of *P. furiosus* (lanes 1–5), 3 partially purified fractions from *T. aquaticus* (lanes 6–8), and 1 extract from *E. coli* (lane 9). Purified PEF (550 ng) and pre-stained molecular weight markers were run in lanes 10 and 11, respectively. With the exception of the markers, all samples were boiled in SDS/BME dye prior to loading.

FIG. 15 depicts the results of the Western Blot. Extracts were prepared from 5 different fermentations of *P. furiosus* (lanes 1–5). In addition, three extracts or partially purified column fractions from *T. aquaticus* (lane 8) and one extract from *E. Coli* (lane 9) were also run. Purified PEF (550 ng) and pre-stained molecular weight markers were run in lanes 10 and 11, respectively. With the exception of the markers, all samples were boiled in SDS/BME dye prior to loading. The results show PEF specific IgG binds to and cross reacts with components of the PEF complex in crude *Pfu* extracts, including the P50 and P45 components. In contrast, no cross reaction was observed with extracts from *T. aquaticus* or *E. coli.*

EXAMPLE 11

Use of PEF Complex in Nucleic Acid Replication Reactions

Initially and as a control to confirm the activity of the DNA polymerase used, gapped-duplex calf thymus DNA (Pharmacia) assays were performed. The polymerase cocktail contained 50 mM Tris-HCl, pH 8.0, 5 mM $MgCl_2$, 1 mM DTT, 50 $\mu$g/ml BSA, 4% glycerol, 200 $\mu$M each dNTP, [$^3$H]TTP (0.5 mCi/$\mu$mole final concentration), and 250 $\mu$g/ml of activated calf thymus DNA (Pharmacia). Samples containing *Pfu* DNA polymerase or *P. furiosus* PEF were serially diluted in *Pfu* DNA polymerase storage buffer (50 mM Tris-HCl, pH 8.2, 0.1% NP40, 0.1% Tween-20, 0.1 mM EDTA, 1 mM DTT, 50% glycerol) and then 1 $\mu$l of each dilution was added to 10 $\mu$l aliquots of polymerase cocktail. Polymerization reactions were conducted in triplicate for 30 minutes at 72° C. The extension reactions were quenched on ice, and then 5$\mu$l aliquots were spotted immediately onto DE81 filters (Whatman). Unincorporated [$^3$H]TTP was removed by 6 washes with 2×SCC (0.3M NaCl, 30 mM sodium citrate, pH 7.0), followed by one wash with 100% ethanol. Incorporated radioactivity was measured by scintillation counting. The assay was calibrated by counting a known amount of [$^3$H]TTP on DE-81 filters, omitting the wash steps. One unit of polymerase activity is defined as the amount of enzyme which catalyzes the incorporation of 10 nmoles of total dNTP into polymeric form (binds to DE-81 paper) in 30 minutes at 72° C. Polymerase concentrations (U/ml) were extrapolated from the slope of the linear portion of units vs. enzyme volume plots.

The PEF samples tested exhibit no significant DNA polymerase activity while the *Pfu* DNA polymerase exhibited a specific activity of $24\times10^4$ u/mg.

1. Enhancement of Cloned *Pfu* DNA Polymerase with *Pfu* PEF

Figure 16:
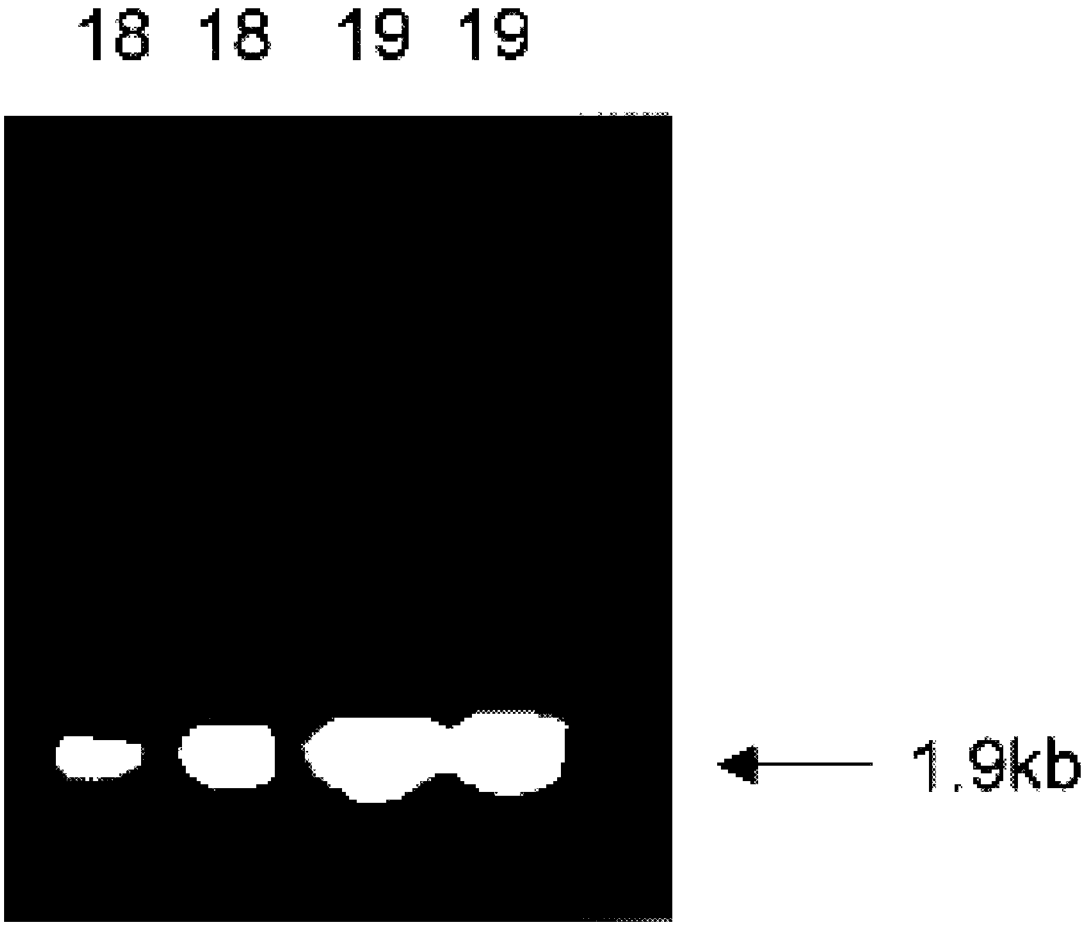
FIGS. 16, 17, and 18. PCR enhancing activity of *P. furiosus* PEF in cloned *Pfu* DNA polymerase PCRs. PCR amplifications were performed as described in example 10 with the following additional notes.
Figure 17:
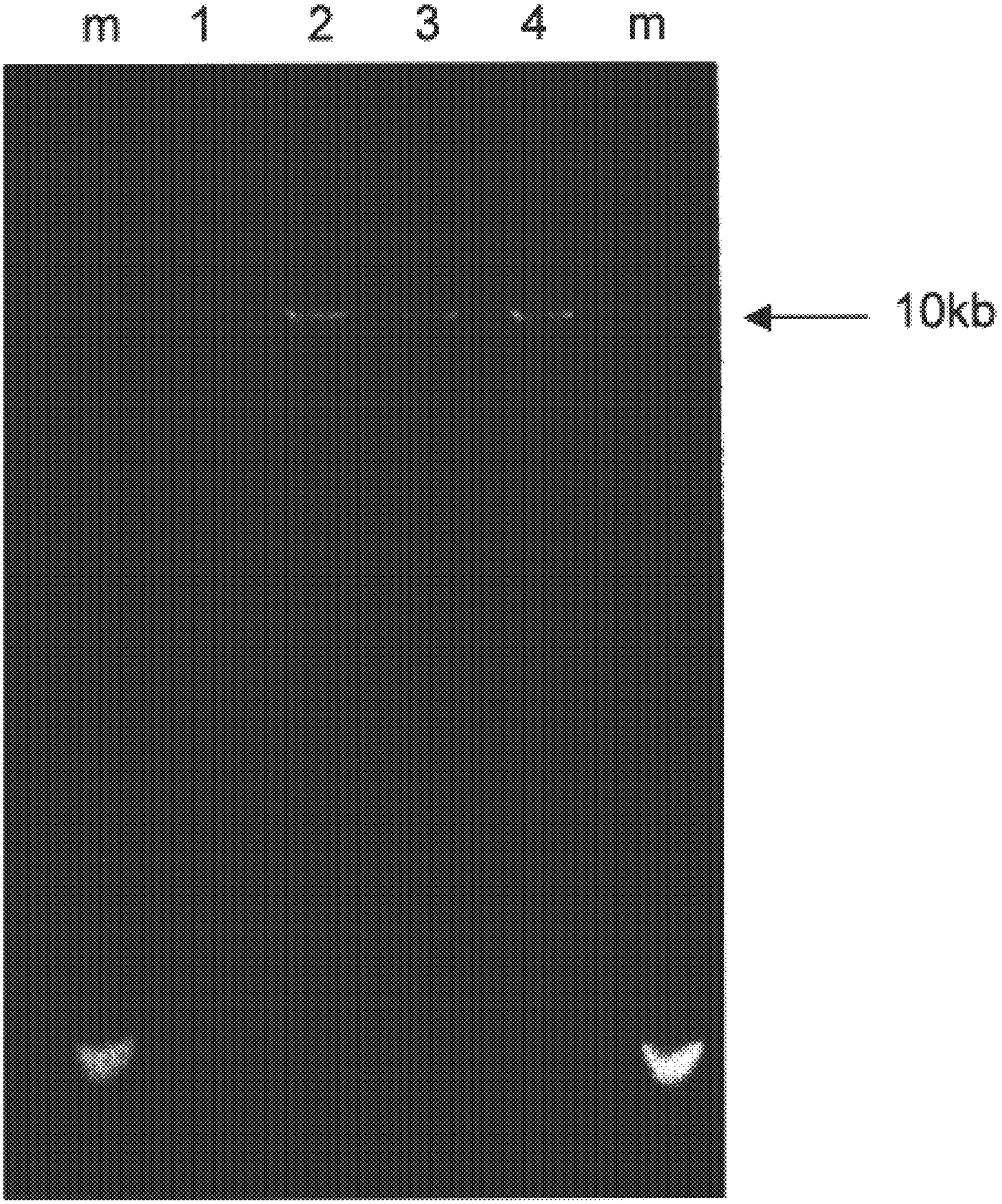
Figure 18:
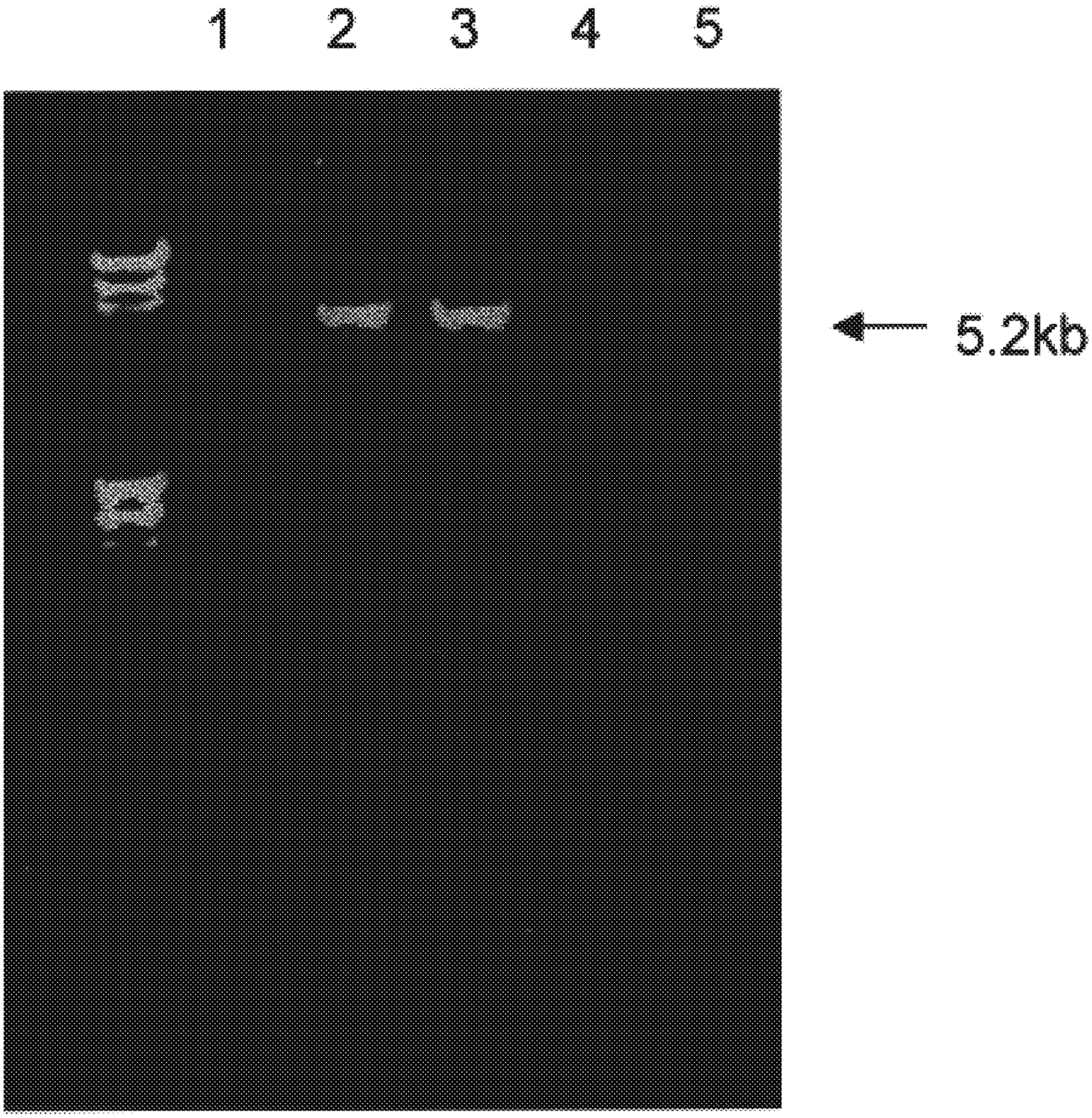

*P. furiosus* PEF has been demonstrated to enhance the yield of PCR products generated with recombinant *Pfu* DNA polymerase using plasmid, lambda, and genomic DNA templates (FIGS. 16–18). The results demonstrate that the addition of *P. furiosus* PEF increases PCR product yield for a variety of PCR systems, ranging in target complexity. Relatively easy targets, e.g. plasmid DNA, can be successfully amplified with *Pfu* DNA polymerase, and the addition of PEF further increases product yield (FIG. 16). Presumably, fewer PCR cycles or lower template concentrations could be used in PEF-containing amplifications.

The most dramatic enhancements are observed when long (FIG. 17) and/or highly complex targets (FIG. 18) are amplified. In the absence of PEF, such targets are poorly amplified by single PCR enzymes, such as *Pfu* DNA polymerase. In FIG. 17, the addition of 1–100 ng of PEF (S200-purified PEF; prep. 3) to 100 $\mu$l PCR reactions containing 5 U of *Pfu* DNA polymerase significantly increased yields of a 10 kb PCR product. In FIG. 18, a 5.2 kb target was successfully amplified from human genomic DNA in the presence of 0.3–280 ng PEF (SCS #52 S200 purified) per 100 μl PCR, but not in the absence of PEF, despite the use of 1.9 min. per kb extension times.

Figure 19:
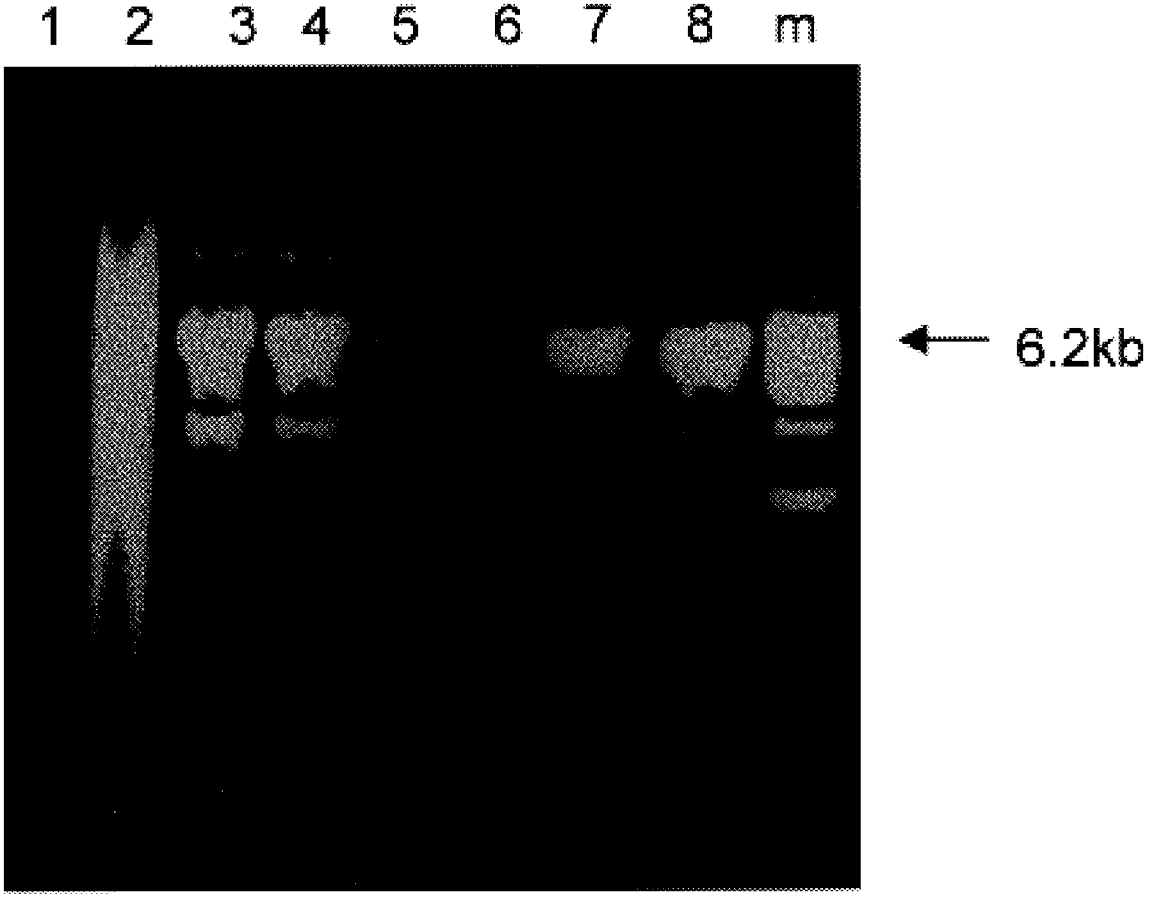
FIG. 19. Effect of Stratagene's Perfect Match (*E. coli* ssb) on the specificity of PCRs conducted with cloned *Pfu* DNA polymerase and *P. furiosus* PEF. PCRs were conducted using the 6.2 kb test system in 100 μl reaction volumes. 1 μl of the following were added to PCRs: lanes 1,5-dilution buffer; lanes 2,6-undiluted PEF-containing heparin sepharose fraction (microcon 30-concentrated SCS #36 H.S. #78, prep. 2; ≈40 ng/μl PEF); lanes 3,7-PEF fraction diluted 1:10; lanes 4,8-PEF fraction diluted 1:100. 1 μl of Perfect Match was added to PCRs run in lanes 5–8.

*P. furiosus* PEF has been found to enhance the yields of both specific and non-specific PCR products, when amplifications are conducted under less stringent PCR conditions with PCR primers that hybridize to more than one target. *E. coli* ssb (single-stranded binding protein; Stratagene's PerfectMatch) has been shown previously to increase the specificity of primer extension reactions, presumably by minimizing the formation of poorly matched primer-template complexes. When used in conjunction with *E. coli* ssb, *P. furiosus* PEF has been found to enhance the yield of specific PCR products (FIG. 19). *Pfu* PEF also enhances yields of PCR products obtained with exo-*Pfu* and a mixtures of Taq and *Pfu* polymerase (for example, TaqPlus Long™, Stratagene; La Jolla, Calif.). Therefore, *Pfu* PEF is useful with polymerase mutants, truncated version of polymerases, mixtures of polymerase, and polymerase-additive combinations (for example, Perfect Match®, Stratagene).

2. Enhancement of Native *Pfu* DNA Polymerase with *Pfu* PEF

Subsequent to identifying PEF from *P. furiosus*, we recognized that certain lots of native *Pfu* DNA polymerase preparations contained PEF. Varying amounts of the >250 kD aggregate could be detected on silver-stained SDS-PAGE gels (FIG. 14). Eleven of the 23 preparations examined were found to visibly contain low levels (8/11 lots; 0.1–1% total protein) to high levels (3/11 lots; 10–30% total protein) of PEF. PEF co-migrates with *Pfu* DNA polymerase during the initial Q- and SP-Sepharose columns in *Pfu* DNA polymerase purification, and elutes just after the major peak of *Pfu* DNA polymerase activity on the Heparin Sepharose column (FIG. 20). *Pfu* DNA polymerase fractions pooled after the Heparin Sepharose step are typically contaminated with varying amounts of PEF, depending upon the column efficiency and pooling strategy employed.

Contamination of native *Pfu* DNA polymerase with varying amounts of PEF could potentially contribute to lot-to-lot variation in the performance of native *Pfu* DNA polymerase in PCR. It is expected that lots containing approximately 1–100 ng of PEF per 2.5 U of *Pfu* DNA polymerase will give rise to higher PCR product yields than amplifications conducted with cloned *Pfu* DNA polymerase or native *Pfu* DNA polymerase lots contaminated with ≦10 pg per 2.5 U *Pfu* DNA polymerase (<0.02% total protein). In theory, a lot containing certain PEF concentrations would exhibit reduced *Pfu* DNA polymerase performance, based upon the apparent inhibition of PEF at high concentrations discussed below (>900 ng per 2.5 U *Pfu* DNA polymerase in 100 μl PCRs).

When adding PEF to native *Pfu* DNA polymerase PCR amplifications, it is anticipated that the level of PEF contained in a particular lot of native *Pfu* must be taken into account to avoid smearing, inhibition of synthesis, or sub-optimal enhancement.

EXAMPLE 12

Use of PEFs in Amplification Reactions

1. Activity of *Pfu* PEF in a Standard PCR Protocol

To enhance PCR product yield, *P. furiosus* PEF is added, separately or pre-mixed with the DNA polymerase, to standard PCR amplifications. PCR amplification reactions generally consist of the following: 0.01–0.05 U/μl DNA polymerase, 0.01 to 1 ng/μl *P. furiosus* PEF, 1–5 ng/μl of each primer, 0.5–10 ng/μl of genomic DNA template, and 0.2 mM each dNTP in a suitable buffer (e.g., cloned *Pfu* DNA polymerase buffer consists of 10 mM KCl, 10 mM $(NH_4)_2SO_4$, 20 mM Tris-HCl (pH 8.8), 2 mM $MgCl_2$, 0.1%(v/v) Triton X-100, and 100 ng/μl BSA). Amplifications from less-complex templates (e.g., lambda or plasmid DNA) are typically successful with 1–100 pg/μl DNA. PCR amplifications are conducted under standard conditions; e.g., 94–96° C. for 0.5–2 min. (1 cycle)/94–96° C. for 0.5–2 min.; 50–65° C. for 0.5–2 min.; 68–72° C. for 0.5–3 min. per kb of target amplified (30–40 cycles)/72° C. for 0–10 min. (1 cycle).

2. Enhancement of PCR Amplification Reactions Employing DNA Polymerases Other than *Pfu* DNA Polymerase

*P. furiosus* PEF has been found to enhance the performance of other α-type (Family B-related) DNA polymerases from thermophilic archeabacteria. Enhanced PCR product yields were observed when *P. furiosus* PEF was added to amplifications conducted with DNA polymerases from both Pyrococcus and Thermococcus species. DNA polymerases demonstrated to function with *P. furiosus* PEF include: Pwo DNA polymerase (Boehringer Mannheim; cloned from *P. woesel*), Deep Vent DNA polymerase (New England Biolabs; cloned from P. sp. GBD), JDF3 DNA polymerase (Stratagene; cloned from P. sp. JDF3), ES4 DNA polymerase (Stratagene; purified from P. sp. ES4) and Vent DNA polymerase (New England Biolabs; cloned from *T. litoralis*).

Figure 21:
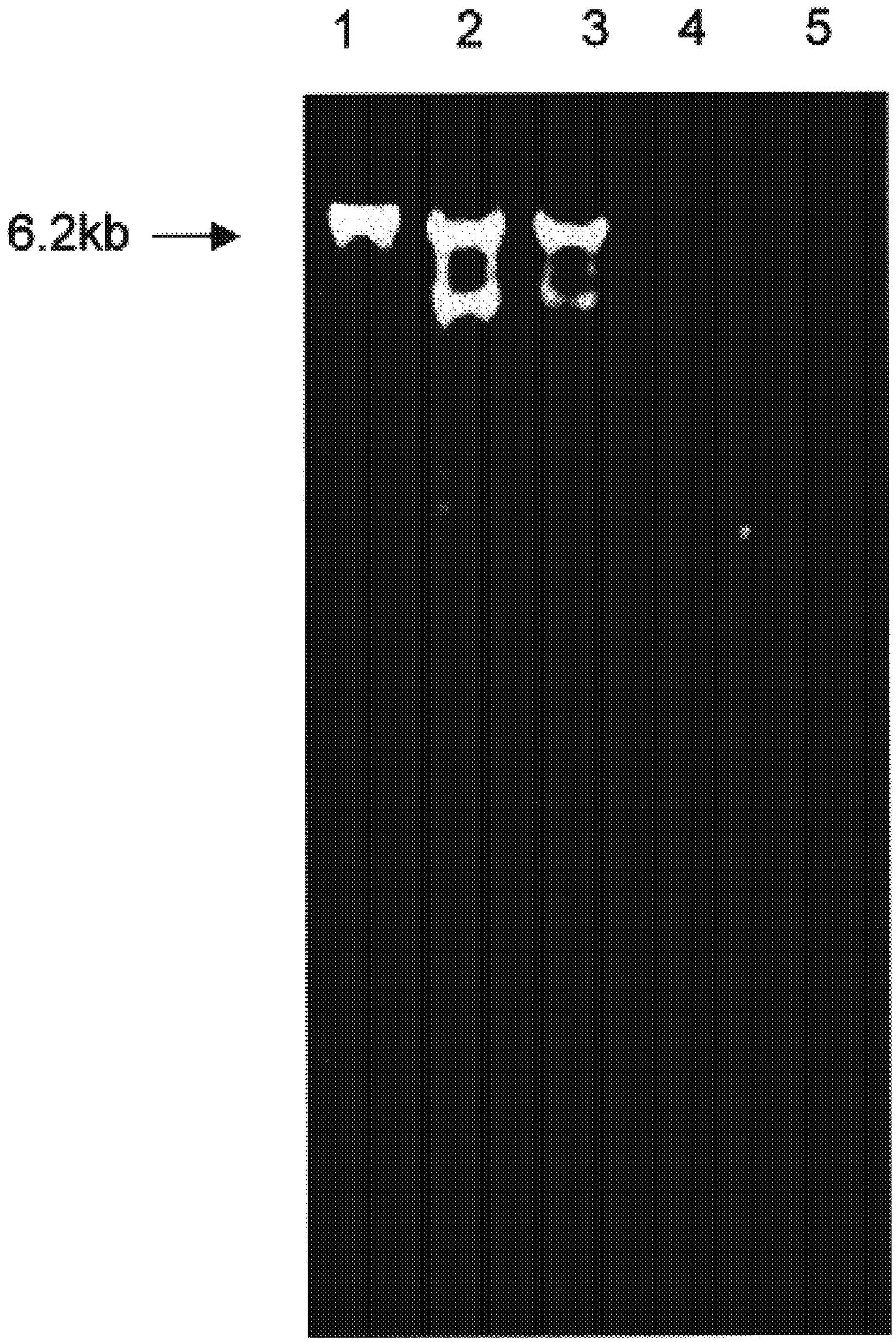
FIGS. 21–24. Enhancing activity of *P. furiosus* PEF in PCRs conducted with Pwo (FIG. 21), JDF-3 (FIG. 22), Vent (FIG. 23), and Deep Vent (FIG. 24) DNA polymerases.
Figure 22:
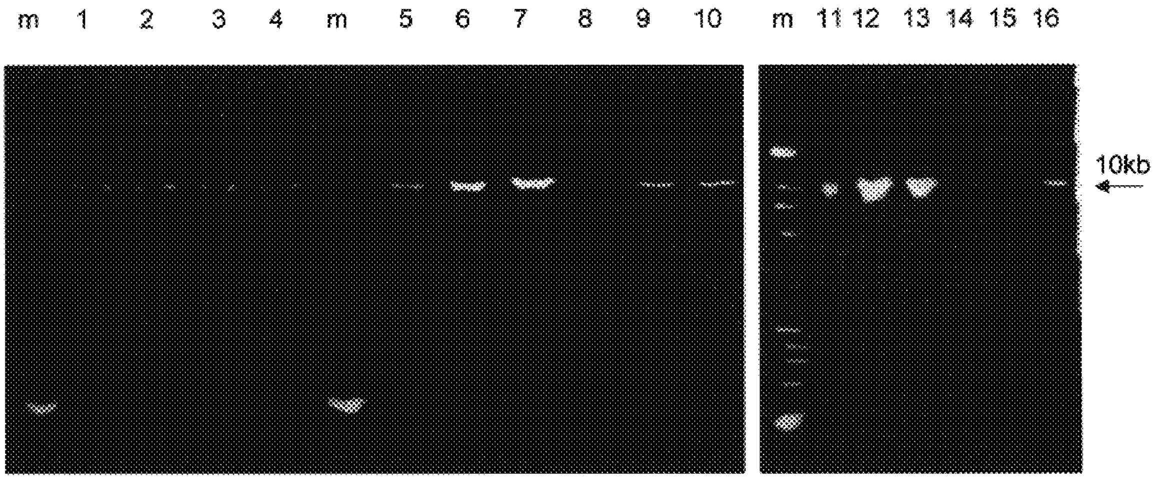
Figure 23:
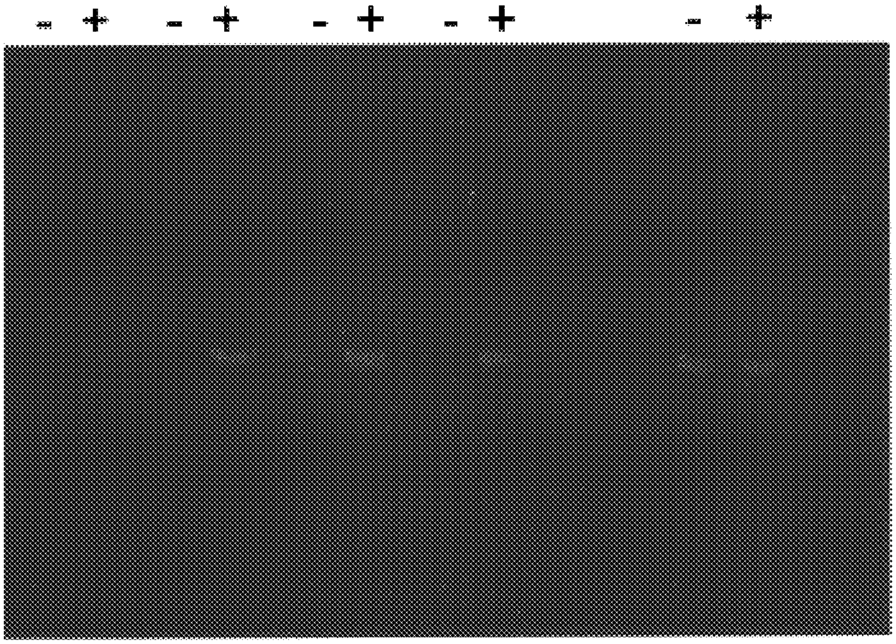
Figure 24:
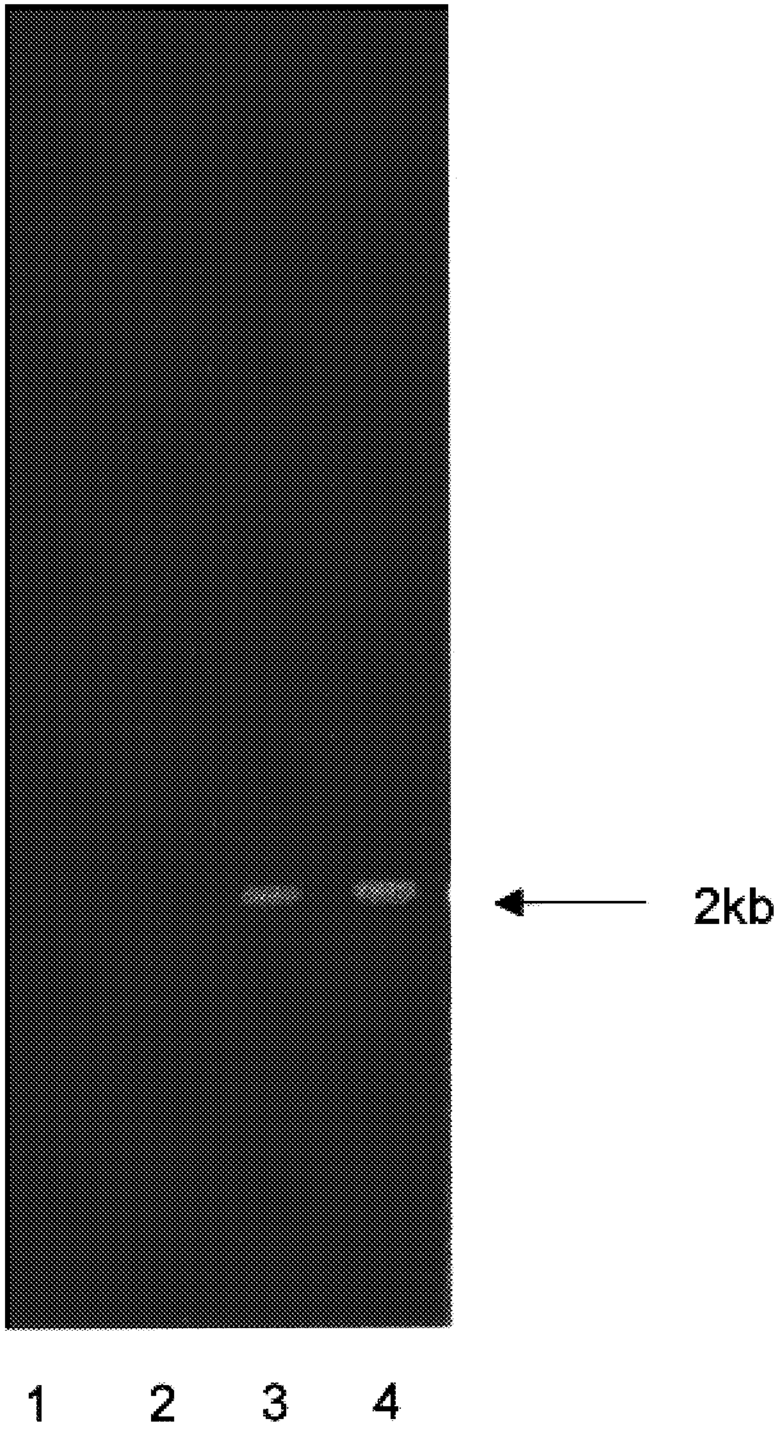

In FIG. 21, S200-purified *Pfu* PEF (prep. 1) increased yields of a 6.2 kb PCR product obtained with 2.5 U of Pwo DNA polymerase. In FIG. 22, the addition of S200-purified PEF (prep. 3) to JDF3 DNA polymerase PCRs increased the yield of a 10 kb product amplified from lambda DNA (lanes 5–7; 11–13) and mouse genomic DNA containing 40 copies (lanes 8–10) or 1 copy (lanes 14–16) of a lambda DNA transgene. In JDF3 DNA polymerase-based PCRs, amplifications are typically conducted with 1 U of enzyme and extension times of 0.5 min./kb target. In FIG. 23, the addition of 5 ng of S200-purified PEF (prep. 3) to ES4, JDF3, *Pfu*, and Vent DNA polymerase PCRs increased the yield of a 1.9 kb product amplified from *P. furiosus* genomic DNA. In FIG. 24, the addition of *P. furiosus* PEF was also shown to increase yields of a 2 kb PCR product amplified with Deep Vent DNA polymerase from mouse genomic DNA.

The addition of *P. furiosus* PEF may not enhance the yield of PCR products generated with Taq DNA polymerase (FIGS. 22 lanes 14 and 23 lanes 9–10). Taq DNA polymerase is a Pol I-like (Family A-related) DNA polymerase isolated originally from the thermophilic eubacteria *Thermus aquaticus.*

3. Enhancement of RT-PCR Reactions

*P. furiosus* PEF has also been shown to enhance the yield of PCR products amplified from reverse transcribed RNA (cDNA) in a process known as RT-PCR, known in the art. Enhancement has been observed in both 2-step (FIG. 25) and 1-tube RT-PCR protocols (data not shown). In the former procedure, aliquots of cDNA synthesis reactions are added to PCR reactions containing a thermostable DNA polymerase (e.g., *Pfu* DNA polymerase) and *P. furiosus* PEF. In the latter approach, RNA is added to reaction mixtures containing a thermolabile RT, dNTPs, primers, a thermostable DNA polymerase (*Pfu* DNA polymerase), and *P. furiosus* PEF. cDNA synthesis and PCR amplification take place sequentially, in the same tube, by conducting cDNA synthesis at 37–42° C., followed by PCR amplification at elevated temperatures.

In the 2-step RT-PCR procedure, cDNA synthesis is first performed by combining the following reagents (50 μl final volume): 5 μg total RNA pre-annealed to 300 ng of primer (oligo dT, random hexamers, or a gene-specific primer), 4 mM each dNTP, 20 U RNase block (optional), and 50 U MMLV RT (or other RT) in buffer containing 50 mM Tris-HCl (pH 8.3), 75 mM KCl, 3 mM $MgCl_2$, and DEPC-treated water. cDNA synthesis is allowed to proceed for 1 hour at 37–42° C. After heat inactivation of the RT, 1 μl of cDNA is added to a 50 μl PCR reaction containing 5 U *Pfu* DNA polymerase, 0.01–50 ng *P. furiosus* PEF, 1 μM of each primer, and 0.2 mM each dNTP in buffer consisting of 10 mM KCl, 10 mM $(NH_4)_2SO_4$, 20 mM Tris-HCl (pH 8.8), 3 mM $MgSO_4$, 0.1%(v/v) Triton X-100, and 100 μg/ml BSA. PCR can be conducted using the following cycle conditions: 94° C. 2 min.; 60° C. 2 min.; 68° C. 1 min. per kb (1 cycle) and then 94° C. 1 min.; 60° C. 1 min.; 68° C. 1 min. per kb (40 cycles).

The enhancement of RT-PCR with *P. furiosus* PEF was evaluated using PCR primers designed to span at least one intron-exon junction in the EGF receptor gene. Two primer sets were used(antisense:5'GAG-TTA-AAT-GCC-TAC-ACT-GTA-TCT (SEQ ID NO.: 59); sense:5'CAG-GAC-TCA-GAA-GCT-GCT-ATC-GAA (1 kb) (SEQ ID NO.: 60) or 5'CTG-CAC-GTG-CCC-TGT-AGG-ATT-TGT (3 kb) (SEQ ID NO.: 61)), which generate PCR products of 1 kb or 3 kb, as indicated, when amplification occurs from spliced RNA rather than contaminating DNA.

Figure 25:
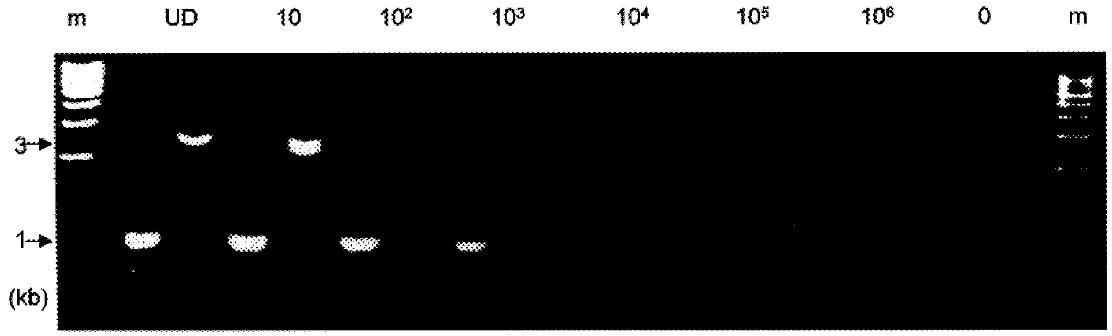
FIG. 25. Enhancement of RT-PCR with *P. furiosus* PEF. A portion of the EGF receptor sequence was amplified from $HepG_2$ total RNA using the 2-step RT-PCR protocol described with the following additions. 1 μl of a cDNA synthesis reaction was added to 50 μl PCR reactions containing 5 U *Pfu* DNA polymerase, 1 μM antisense primer (5' GAG-TTA-AAT-GCC-TAC-ACT-GTA-TCT) (SEQ ID NO: 29), 1 μM sense primer [5' CAG-GAC-TCA-GAA-GCT-GCT-ATC-GAA (SEQ ID NO: 30) (1 kb product) or5'CTG-CAC-GTG-CCC-TGT-AGG-ATT-TGT (SEQ ID NO: 31) (3 kb product)]. 1 μl of buffer (0) or 1 μl of a PEF-containing heparin sepharose fraction (SCS #37 H.S. #75; prep. 4; ≈10 ng/μl PEF) was added undiluted (UD) or diluted 1:10 to $1:10^6$ (as indicated). PCRs were conducted in cloned *Pfu* PCR buffer, containing 3 mM $MgSO_4$.

The PEF concentration which gives optimal performance was determined by titrating PEF preparation 3 (S-200 purified) and preparation 4 (heparin sepharose fraction) in the 2-step RT-PCR procedure described here. With PEF preparation 4, significant increase in the yield of the 1 kb product was observed when 0.001–1 μl was added (10 pg–10 ng PEF) (FIG. 25). Synthesis of the 3 kb product was significantly enhanced when 0.1–1 μl (1–10 ng PEF) of preparation 4 was added. With PEF preparation 3, significant increases in the yields of both the 0.6 kb and the 3 kb products were observed for all amounts tested in the range of 0.002–0.1 μl (1–50 ng).

4. Enhancement of Seamlessυ Cloning Protocol

Figure 26:
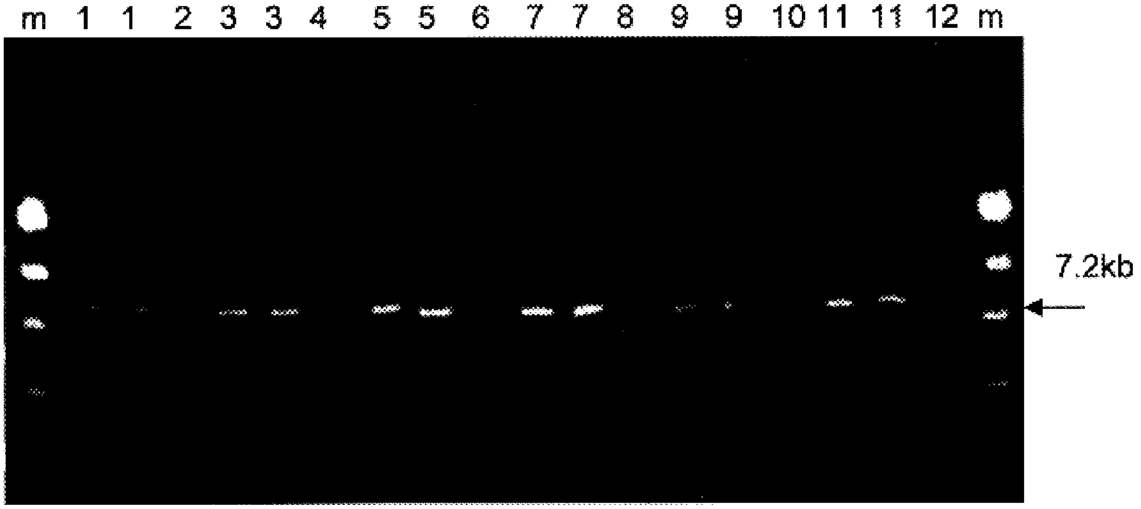
FIG. 26. Enhancement of *Pfu* DNA polymerase-based Seamless Cloning with *P. furiosus* PEF. 20 ng of plasmid was amplified as described in the Seamless Cloning kit protocol in the absence (lanes 2,4,6,8,10,12) or presence (duplicate lanes 1,3,5,7,9,11) of S200-purified *P. furiosus* PEF (prep. 3; 550 ng/μl), diluted 1:100. A 7.2 kb target was amplified with 6 different primer pairs (each set of 3 lanes).

Seamless Cloning was performed using Stratagene's Seamless™ Cloning kit, following the recommended protocol. The effect of *P. furiosus* PEF on the efficiency of Seamless Cloning is shown in FIG. 26. Increased yield of a 7.2 kb PCR product was observed when 5 ng of S-200 purified PEF (prep. 1) was added to 50 μl PCR reactions containing 2.5 U *Pfu* DNA polymerase and methyl dCTP. Amplifications conducted in the presence of PEF utilized 1 min. per kb extension times. In the absence of PEF, very little PCR product was generated despite the use of longer 2 min./kb extension times.

5. Enhancement of Linear Amplification Reactions: QuikChange™ Mutagenesis Protocol Site-specific mutagenesis can be accomplished efficiently with double-stranded DNA templates using a linear amplification-based strategy employing *Pfu* DNA polymerase (QuikChange™ Site-Directed Mutagenesis Kit; Stratagene; La Jolla, Calif.). PCR primers containing the desired mutation(s) are designed to anneal to the same site on opposite strands. Primer extension reactions are conducted with a thermostable DNA polymerase (e.g. *Pfu* DNA polymerase) at temperatures which allow efficient synthesis in the absence of strand displacement activity (68° C.). The amplification product is treated with Dpnl to digest the parental methylated plasmid DNA and the resulting gapped, double-stranded DNA is then transformed into competent *E. coli* cells. Mutant clones are identified by DNA sequencing.

In evaluating *P. furiosus* PEF, mutagenesis was conducted using Stratagene's Quik Change mutagenesis kit, except that both recombinant and native *Pfu* DNA polymerase were used in the kit-supplied reaction buffer. The effect of *P. furiosus* PEF on the efficiency of QuikChange mutagenesis is shown in FIG. 27. The addition of 0.04 to 4 ng of PEF of PEF prep. 2 (heparin sepharose fraction SCS # 36 H.S. #78) to 50 μl reactions increased the number of transformants generated by native and cloned *Pfu* DNA polymerases, while retaining mutation frequencies of 90–97%. Optimal results were obtained with 0.4 ng of PEF, which gave 7.5-fold and 5.3-fold increases in the number of mutant colonies generated with native and cloned *Pfu* DNA polymerase, respectively.

As the use of PEFs in linear amplification methods such as the QuikChange™ mutagenesis protocol corresponds to the use of PEFs in other linear amplification reactions known in the art, such as cycle sequencing reactions, primer extension reactions, and the like. PEFs can be employed in any linear amplification method to enhance the activity of the polymerase used. For example, the effect of *Pfu* PEF on cycle sequencing can be evaluated by comparing the quality and length of sequencing ladders generated with a polymerase, for example $exo^-$*Pfu* DNA polymerase, in the absence and in the presence of PEF. A number of different cycle sequencing reactions, known to one skilled in the art, can be used in combination with the PEF complexes and proteins of this invention to enhance polymerase activity. In addition, primer extension reactions can also be enhanced with the use of PEFs. Numerous primer extension reactions are known in the art.

EXAMPLE 13

Enhancing Titer of PEF

The nucleic acid replication enhancing activity of several different preparations of *Pfu* PEF have been evaluated in PCR, PCR-related applications, linear amplification-based applications, mutagenesis applications, cycle sequencing applications, and primer extension applications. One skilled in the art will appreciate that similar methods to optimize the use of any PEF, such as those specifically discussed herein, are apparent from the disclosure herein.

A sample of substantially homogeneous PEF enhances the performance of *Pfu* DNA polymerase in PCR amplification reactions when added at concentrations spanning a 10,000-fold range (0.09–900 ng/100 μl). The highest yields of amplified product are observed in the presence of ≈1 to 100 ng of P50. The addition of excess P50 (≧900 ng/100 μl) or very low P50 concentrations (<9 pg/100 μl) in a PCR reaction resulted in lower PCR product yield. The relative purity and PEF content of 4 preparations was examined by SDS-PAGE analysis (FIG. 10). Preparations 1 and 3 consist of S200-purified PEF of >95% homogeneity, while preparations 2 and 4 consist of concentrated heparin sepharose fractions of 10–20% homogeneity (SCS #36 H.S. 78, SCS #37 H.S. #75).

The PCR enhancing titer of S200-purified *P. furiosus* PEF (prep. 1; FIGS. 7 and 10) was determined using the F432-21/R6656-20/λAA742 primer-template system described above. This preparation is approximately 95% pure, contains <0.001 U/μl DNA polymerase activity, and ≈225 ng/μl PEF. PCR enhancing activity was found to be optimal when 0.004–0.4 μl (0.9–90 ng) of homogeneous *P. furiosus* PEF was added to 100 μl PCR reactions containing 2.5 U of *Pfu* DNA polymerase. Reduced, but significant, PCR product yield was observed when 4 μl (900 ng) or 0.0004 μl (0.09 ng) of the S200-purified protein was added (FIG. 28). In a second identical experiment, significant enhancement was noted when 0.004–4 μl was added, and very little improvement was noted with 0.0004 μl (FIG. 29).

The PCR enhancing titer of PEF preparation 2 was also determined (FIGS. 30–31). Preparation 2 consisted of a concentrated (Microcon-30) heparin sepharose fraction, in which *P. furiosus* PEF made up approximately 10% of the total protein and was present at approximately 40 ng/μl. Enhanced PCR product yield was observed when 0.0002–0.2 μl (0.008–8 ng) of the column fraction was added to 100 μl PCR reactions containing 2.5 U of *Pfu* DNA polymerase, with greatest enhancements observed in the range of 0.002–0.2 ∞l (0.08–8 ng) (FIG. 30). In a second identical experiment, enhanced PCR product yield was observed when 0.004–0.04 μl (0.16–1.6 ng) of PEF preparation 2 was added to 2.5 U of DNA polymerase per 100 μl PCR reaction (FIG. 31). No PCR product was observed in the presence of 4 μl (160 ng) or 0.0004 μl (0.016 ng) of the column fraction, while a smear was generated when 0.4 μl (16 ng) of the column fraction was added to PCR. Smeary PCR products were also noted previously when 1 μl of heparin sepharose fractions containing the highest concentrations of PEF are added to PCRs (e.g., SCS #37 H.S. fractions 69–81 in FIG. 20; PEF prep. 2 in FIG. 1).

In summary, homogeneous *P. furiosus* PEF enhances the performance of *Pfu* DNA polymerase in test PCR amplifications when added at concentrations spanning a 10,000-fold range (0.09–900 ng/100 μl). The highest yields are observed in the presence of ≈1 to 100 ng of PEF. The addition of excess PEF (≧900 ng/100 μl) or PEF <9 pg/100 μl PCR reaction, was found to give reduced performance (lower PCR product yield). Partially-purified PEF samples (heparin sepharose column fractions) also appear to enhance PCR product yield over a fairly broad range of PEF concentrations. With the column fraction analyzed here, highest yields of PCR were obtained in the range of 0.08 ng to 8 ng. The addition of higher amounts of the column fraction (0.4–4 μl) resulted in smearing (16–40 ng) or lack of enhancement (160 ng).

Figure 20:
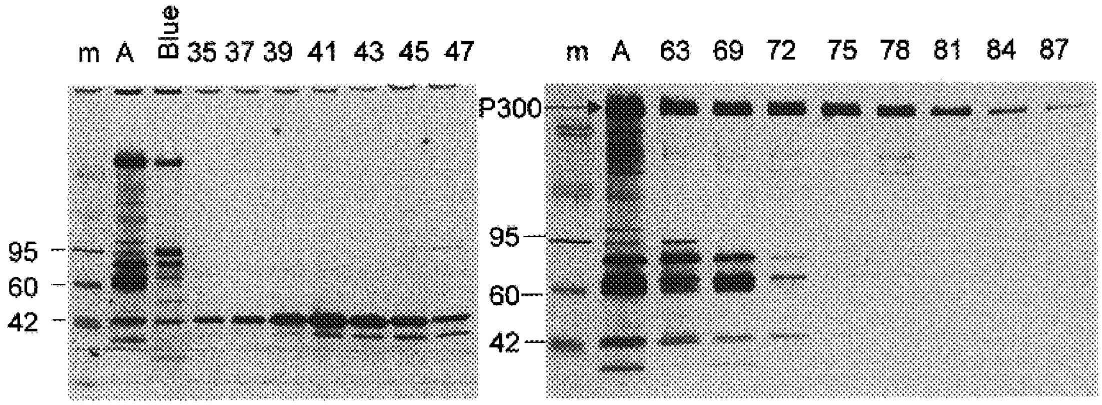
FIG. 20. SDS-PAGE analysis of heparin sepharose (H.S.) column fractions. The heparin sepharose fractions indicated (# at top) from SCS native *Pfu* DNA polymerase prep. #37 (SCS #37) were analyzed on 4–20% SDS-PAGE gels (4 μl/lane). Prestained molecular weight markers were run in lanes denoted "m" and 4 μl of SCS #36 H.S. #78 (PEF prep. 2) was run in lanes marked "A".

Inhibition of PCR enhancement at high concentrations of PEF appears to occur irrespective of the purity of the PEF sample. The addition of higher concentrations of homogeneous PEF (≧900 ng) resulted in lower yields of PCR product than could be obtained with <900 ng PEF. Heparin sepharose fractions of 10–20% purity also gave reduced PCR product yields when high amounts of PEF were added. Up to 8 ng of PEF in prep. 2 (H.S. #78 fraction) could be added before smearing or inhibition occurred. The discrepancy between the amount of PEF which is inhibitory in homogeneous preparations (≧900 ng), as compared to partially-purified column fractions (>16 ng), suggests that additional protein or DNA contaminants may be present in the heparin sepharose fractions. Examination of heparin sepharose fractions revealed that *P. furiosus* PEF elutes just after the major peak of *Pfu* DNA polymerase activity (e.g., fractions 50–61 in FIG. 20). SDS-PAGE analysis showed that the highest levels of the >250 kD PEF appeared in fractions 63–78 from the SCS #36 native *Pfu* DNA polymerase purification (FIG. 20). PCR enhancing activity was observed in fractions 37–90 (FIG. 32). Discrete PCR product bands were generated with fractions 37–48 and 87–90, which contain very low levels of PEF. Interestingly, DNA smears were generated with fractions 69–81 (FIG. 32), which contain the highest levels of PEF and no detectable *Pfu* DNA polymerase. These results suggest that *P. furiosus* PEF may be inhibitory when present at high concentrations or, alternatively, that a contaminant co-purifies with PEF.

As observed with PCR, inhibition during linear amplification protocols was noted with high concentrations of PEF-containing heparin sepharose fractions. The addition of 40 ng (1 μl prep. #2) of PEF to QuickChange™ reactions resulted in reduced yield of amplification product, as visualized by a reduction in the ethidium bromide-staining intensity of DNA bands on agarose gels. Reduced yield accompanied a 1.8 to 2.8-fold reduction in the number of transformants and a slight, but reproducible, decrease in mutation frequency.

Each of the references referred to herein can be relied on by one skilled in the art in making and using embodiments of the invention. In addition, each reference is specifically incorporated, in its entirety, into this disclosure.

What is claimed is:

1. A non-naturally occurring composition of matter comprising at least one component possessing nucleic acid polymerase enhancing activity selected from the group consisting of: an isolated or purified naturally occurring polymerase enhancing protein obtained from an archeabacteria source; a wholly or partially synthetic protein having the same amino acid sequence as said naturally-occurring protein or analogs thereof possessing polymerase enhancing activity; polymerase-enhancing mixtures of one or more of said naturally occurring or wholly or partially synthetic proteins; polymerase-enhancing protein complexes of one or more of said naturally occurring or wholly or partially synthetic proteins; or polymerase-enhancing partially purified cell extracts containing one or more of said naturally occurring proteins.

2. A composition of matter according to claim 1 wherein said component possessing polymerase enhancing activity is a cell extract.

3. A composition of matter according to claim 2 wherein said cell extract is from an archeabacteria source.

4. A composition of matter according to claim 3 wherein said cell extract is from *Pyrococcus furiosus*.

5. A composition of matter according to claim 1 wherein said component possessing polymerase enhancing activity is a protein complex.

6. A composition of matter according to claim 5 wherein said protein complex is from an archeabacteria source.

7. A composition of matter according to claim 6 wherein said protein complex is from *Pyrococcus furiosus*.

8. A composition of matter according to claim 7 wherein said protein complex is P300.

9. A composition of matter according to claim 5 wherein said protein complex comprises a plurality of subunits wherein at least one subunit has a molecular weight of approximately 45 kD.

10. A composition of matter according to claim 9 wherein a subunit has a sequence of amino acids at the amino terminal end comprising SEQ ID NO: 46.

11. A composition of matter according to claim 9 wherein a subunit has a sequence of amino acids comprising one of SEQ ID NO: 47 or 48.

12. A composition of matter according to claim 10 or 11 further comprising a subunit encoded by a DNA having the nucleotide sequence of SEQ ID NO: 18.

13. A composition of matter according to claim 1 wherein said component possessing polymerase enhancing activity is a protein.

14. A composition of matter according to claim 13 wherein said protein is from an archeabacteria source.

15. A composition of matter according to claim 14 wherein said protein is from *Pyrococcus furiosus*.

16. A composition of matter according to claim 15 wherein said protein comprises at least one protein having a molecular weight of approximately 45 kD.

17. A composition of matter according to claim 16 wherein said protein is selected from the group consisting of: a protein having a sequence of amino acids at the amino terminal end comprising one of SEQ ID NO: 11; a protein encoded by a nucleic acid having the sequence of SEQ ID NO: 42 or degenerate variants thereof; or a protein having a sequence of amino acids comprising one of SEQ ID NO: 37–39, 41, or 43–48.

18. A composition of matter according to claim 1 wherein said component possessing polymerase enhancing activity is a wholly or partially synthetic protein having the same amino acid sequence as said naturally-occurring protein or analogs thereof.

19. A composition of matter according to claim 18 wherein said protein has a molecular weight of approximately 45 kD.

20. A composition of matter according to claim 19 wherein said protein has a sequence of amino acids at the amino terminal end comprising SEQ ID NO: 3, 11 or 46.

21. A composition of matter according to claim 19 wherein said protein has a sequence of amino acids comprising one of SEQ ID NO: 5, 6, 47 or 48.

22. A composition of matter according to claim 20 or 21 further comprising a subunit encoded by a DNA having the nucleotide sequence of SEQ ID NO: 18.

23. A composition of matter according to claim 1 wherein said component possessing polymerase enhancing activity is a mixture of proteins.

24. An isolated or purified DNA comprising a sequence encoding a protein according to said protein of one of claims 16–17.

25. An isolated or purified DNA having a sequence selected from the group consisting of: the sequence set forth in SEQ ID NO: 18, degenerate sequences thereof, or DNA sequences hybridizable therewith; the sequence set forth in SEQ ID NO: 42, degenerate sequences thereof, or DNA sequences capable of hybridizing therewith.

26. An isolated or purified DNA sequence capable of hybridizing to DNA sequence according to claim 24.

27. An isolated or purified DNA sequence capable of hybridizing to DNA sequence according to claim 20.

28. A composition of matter comprising a polymerase-enhancing protein encoded by DNA according to claim 26.

29. A composition of matter comprising a polymerase-enhancing protein encoded by DNA according to claim 27.

30. A non-naturally occurring mixture of a polymerase-enhancing composition according to claim 1 with one or more DNA polymerases.

31. A mixture according to claim 30 wherein at least one of said polymerases is a thermostable DNA polymerase.

32. A mixture according to claim 30 wherein at least one of said polymerases is derived from an archeabacteria source.

33. A mixture according to claim 32 wherein at least one of said polymerases is a DNA polymerase derived from the Pyrococcus species or the Thermococcus species.

34. A mixture according to claim 33 wherein at least one of said polymerases is Pyrococcus sp. JDF3, Pyrococcus sp. GBD, Pyrococcus sp. KOD, Thermococcus or *Pyrococcus woesii* DNA polymerase.

35. A kit for replicating nucleic acids comprising a polymerase-enhancing composition of claim 1 and at least one nucleic acid polymerase.

36. A kit according to claim 35 containing at least one recombinant nucleic acid polymerase.

37. A kit according to claim 35 or 36 capable of use in a site-directed mutagenesis method.

38. A kit according to claim 35 or 36 capable of use in a nucleic acid sequencing method.

39. A kit according to claim 35 or 36 capable of use in an amplification reaction.

40. An antibody that binds to a composition of matter of claim 1.

41. An antibody that binds to a protein having an amino acid sequence comprising one of SEQ ID NO: 19, 37–39, 41, 43–48.

* * * * *

```
SEQUENCE LISTING

(1) GENERAL INFORMATION:

   (iii) NUMBER OF SEQUENCES: 61


(2) INFORMATION FOR SEQ ID NO:1:

     (i) SEQUENCE CHARACTERISTICS:
          (A) LENGTH: 15 amino acids
          (B) TYPE: amino acid
          (C) STRANDEDNESS: unknown
          (D) TOPOLOGY: unknown

    (ii) MOLECULE TYPE: peptide

   (iii) HYPOTHETICAL: NO

    (iv) ANTI-SENSE: NO

     (v) FRAGMENT TYPE: N-terminal

    (xi) SEQUENCE DESCRIPTION: SEQ ID NO:1:

Xaa Xaa Leu His His Val Lys Leu Ile Tyr Ala Thr Xaa Xaa Xaa
```

-continued

```
1               5                   10                  15


(2) INFORMATION FOR SEQ ID NO:2:

     (i) SEQUENCE CHARACTERISTICS:
          (A) LENGTH: 15 amino acids
          (B) TYPE: amino acid
          (D) TOPOLOGY: unknown

    (ii) MOLECULE TYPE: peptide

   (iii) HYPOTHETICAL: NO

    (iv) ANTI-SENSE: NO

     (v) FRAGMENT TYPE: N-terminal

    (xi) SEQUENCE DESCRIPTION: SEQ ID NO:2:

Xaa Xaa Xaa Pro Asp Trp Xaa Xaa Arg Xaa Glu Xaa Leu Xaa Xaa
1               5                   10                  15


(2) INFORMATION FOR SEQ ID NO:3:

     (i) SEQUENCE CHARACTERISTICS:
          (A) LENGTH: 35 amino acids
          (B) TYPE: amino acid
          (D) TOPOLOGY: unknown

    (ii) MOLECULE TYPE: peptide

   (iii) HYPOTHETICAL: NO

    (iv) ANTI-SENSE: NO

     (v) FRAGMENT TYPE: N-terminal

    (xi) SEQUENCE DESCRIPTION: SEQ ID NO:3:

Xaa Leu Leu His His Val Lys Leu Ile Tyr Ala Thr Lys Xaa Arg Xaa
1               5                   10                  15

Leu Val Gly Lys Xaa Ile Val Leu Ala Ile Pro Gly Xaa Xaa Ala Xaa
            20                  25                  30

Xaa Xaa Xaa
        35


(2) INFORMATION FOR SEQ ID NO:4:

     (i) SEQUENCE CHARACTERISTICS:
          (A) LENGTH: 18 amino acids
          (B) TYPE: amino acid
          (D) TOPOLOGY: unknown

    (ii) MOLECULE TYPE: peptide

   (iii) HYPOTHETICAL: NO

    (iv) ANTI-SENSE: NO

     (v) FRAGMENT TYPE: N-terminal

    (xi) SEQUENCE DESCRIPTION: SEQ ID NO:4:

Xaa Xaa Xaa Pro Asp Trp Xaa Xaa Arg Xaa Glu Xaa Leu Xaa Glu Xaa
1               5                   10                  15

Xaa Xaa


(2) INFORMATION FOR SEQ ID NO:5:

     (i) SEQUENCE CHARACTERISTICS:
          (A) LENGTH: 17 amino acids
          (B) TYPE: amino acid
```

-continued (D) TOPOLOGY: unknown (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:5:

```
Xaa Tyr Asp Ala Val Ile Met Ala Ala Ala Val Val Asp Phe Arg Pro
1               5                   10                  15

Lys
```

(2) INFORMATION FOR SEQ ID NO:6:

(i) SEQUENCE CHARACTERISTICS:
(A) LENGTH: 24 amino acids
(B) TYPE: amino acid
(D) TOPOLOGY: unknown (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:6:

```
Ala Asp Leu Val Val Gly Asn Thr Leu Glu Ala Phe Gly Ser Glu Glu
1               5                   10                  15

Asn Gln Val Val Leu Ile Gly Arg
            20
```

(2) INFORMATION FOR SEQ ID NO:7:

(i) SEQUENCE CHARACTERISTICS:
(A) LENGTH: 17 amino acids
(B) TYPE: amino acid
(D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:7:

```
Gly Ala Met Leu His His Val Lys Leu Ile Tyr Ala Xaa Lys Leu Arg
1               5                   10                  15

Lys
```

(2) INFORMATION FOR SEQ ID NO:8:

(i) SEQUENCE CHARACTERISTICS:
(A) LENGTH: 18 amino acids
(B) TYPE: amino acid
(D) TOPOLOGY: unknown (ii) MOLECULE TYPE: peptide (iii) HYPOTHETICAL: NO (iv) ANTI-SENSE: NO (v) FRAGMENT TYPE: N-terminal -continued (xi) SEQUENCE DESCRIPTION: SEQ ID NO:8:

Gly Ala Met Leu His His Val Lys Leu Ile Tyr Ala Thr Lys Xaa Xaa
1 5 10 15

Arg Lys (2) INFORMATION FOR SEQ ID NO:9:

(i) SEQUENCE CHARACTERISTICS:
(A) LENGTH: 13 amino acids
(B) TYPE: amino acid
(D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:9:

Met Leu His His Val Lys Leu Ile Tyr Ala Thr Lys Leu
1 5 10

(2) INFORMATION FOR SEQ ID NO:10:

(i) SEQUENCE CHARACTERISTICS:
(A) LENGTH: 16 amino acids
(B) TYPE: amino acid
(D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:10:

Gly Xaa Xaa Xaa Pro Asp Trp Xaa Xaa Lys Phe Arg Lys Glu Glu Ser
1 5 10 15

(2) INFORMATION FOR SEQ ID NO:11:

(i) SEQUENCE CHARACTERISTICS:
(A) LENGTH: 17 amino acids
(B) TYPE: amino acid
(D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:11:

Gly Ala Ile Leu Leu Pro Asp Trp Lys Ile Arg Lys Glu Ile Leu Ile
1 5 10 15

Glu (2) INFORMATION FOR SEQ ID NO:12:

(i) SEQUENCE CHARACTERISTICS:
(A) LENGTH: 16 amino acids
(B) TYPE: amino acid

-continued (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:12:

```
Xaa Met His His Val Ile Lys Leu Xaa Tyr Ala Thr Xaa Ser Arg Lys
1               5                   10                  15
```

(2) INFORMATION FOR SEQ ID NO:13:

(i) SEQUENCE CHARACTERISTICS:
(A) LENGTH: 18 amino acids
(B) TYPE: amino acid
(D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:13:

```
Met Leu Tyr Leu Val Arg Pro Asp Trp Lys Arg Arg Lys Glu Ile Leu
1               5                   10                  15

Ile Glu
```

(2) INFORMATION FOR SEQ ID NO:14:

(i) SEQUENCE CHARACTERISTICS:
(A) LENGTH: 23 base pairs
(B) TYPE: nucleic acid
(C) STRANDEDNESS: single
(D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:14:

```
CAYCAYGAHA ARYTHATTTA CGC                                             23
```

(2) INFORMATION FOR SEQ ID NO:15:

(i) SEQUENCE CHARACTERISTICS:
(A) LENGTH: 23 base pairs
(B) TYPE: nucleic acid
(C) STRANDEDNESS: single
(D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:15:

```
GCCATDATNA CDGCRTCGTA TTT                                             23
```

(2) INFORMATION FOR SEQ ID NO:16:

-continued (i) SEQUENCE CHARACTERISTICS:
(A) LENGTH: 23 base pairs
(B) TYPE: nucleic acid
(C) STRANDEDNESS: single
(D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:16:

CAYCAYGAHA ARYTHATATA CGC 23

(2) INFORMATION FOR SEQ ID NO:17:

(i) SEQUENCE CHARACTERISTICS:
(A) LENGTH: 20 base pairs
(B) TYPE: nucleic acid
(C) STRANDEDNESS: single
(D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:17:

ARDACDACYT GRTTTTCTTC 20

(2) INFORMATION FOR SEQ ID NO:18:

(i) SEQUENCE CHARACTERISTICS:
(A) LENGTH: 1209 base pairs
(B) TYPE: nucleic acid
(C) STRANDEDNESS: single
(D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:18:

ATGCTTCACC ACGTCAAGCT AATCTACGCC ACAAAAAGTC GAAAGCTAGT TGGAAAAAAG 60

ATAGTCNNNN NNNNNCCAGG GAGTATTGCG GCTTTGGATG TGAAAGCTTG TGAGGGACTA 120

ATTAGGCATG GGGCCGAAGT TCATGCAGTG ATGAGTGAGG CAGCCACCAA GATAATTCAT 180

CCTTATGCAT GGAATTTGCC CACGGGAAAT CCAGTCATAA CTGAGATCAC TGGATTTATC 240

GAGCATGTTG AGTTAGCAGG GGAACATGAG AATAAAGCAG ATTTAATTTT GGTTTGTCCT 300

GCCACTGCCA ACACAATTAG TAAGATTGCA TGTGGAATAG ATGATACTCC AGTAACTACA 360

GTCGTGACCA CAGCATTTCC CCACATTCCA ATTATGATAG CCCCAGCAAT GCATGAGACA 420

ATGTACAGGC ATCCCATAGT AAGGGAGAAC ATTGAAAGGT TAAAGAAGCT TGGCGTTGAG 480

TTTATAGGAC CAAGAATTGA GGAGGGAAAG GCAAAAGTTG CAAGCATTGA TGAAATAGTT 540

TACAGAGTTA TTAAAAAGCT CCACAAAAAA ACATTGGAAG GGAAGAGAGT CCTAGTAACG 600

GCGGGAGCAA CAAGAGAGTA CATAGATCCA ATAAGATTCA TAACAAATGC CAGCAGTGGA 660

AAAATGGGAG TAGCGTTGGC TGAAGAAGCA GATTTTAGAG GAGCTGTTAC CCTCATAAGA 720

ACAAAGGGAA GTGTAAAGGC TTTTAGAATC AGAAAAATCA AATTGAAGGT TGAGACAGTG 780

GAAGAAATGC TTTCAGCGAT TGAAAATGAG TTGAGGAGTA AAAAGTATGA CGTAGTTATT 840

-continued

```
ATGGCAGCTG CTGTAAGCGA TTTTAGGCCA AAAATTAAAG CAGAGGGAAA AATTAAAAGC    900

GGAAGATCAA TAACGATAGA GCTCGTTCCN NNNAATCCCA AAATCATTGA TAGAATAAAG    960

GAAATTCAAC CAAATGTCTT TCTTGTTGGA TTTAAAGCAG AAACTTCAAA AGAAAAGCTT   1020

ATAGAAGAAG GTAAAAGGCA GATTGAGAGG GCCAAGGCTG ACTTAGTCGT TGGTAACACA   1080

TTGGAAGCCT TTGGAAGCGA GGAAAACCAA GTAGTATTAA TTGGCAGAGA TTTCACAAAA   1140

GAACTTCCAA AAATGAAAAA GAGAGAGTTA GCAGAGAGAA TTTGGGATGA GATAGAGAAA   1200

TTNCTGTCC                                                          1209
```

(2) INFORMATION FOR SEQ ID NO:19:

(i) SEQUENCE CHARACTERISTICS:
(A) LENGTH: 403 amino acids
(B) TYPE: amino acid
(D) TOPOLOGY: unknown (ii) MOLECULE TYPE: protein (iii) HYPOTHETICAL: NO (xi) SEQUENCE DESCRIPTION: SEQ ID NO:19:

```
Met Leu His His Val Lys Leu Ile Tyr Ala Thr Lys Ser Arg Lys Leu
1               5                   10                  15

Val Gly Lys Lys Ile Val Xaa Xaa Xaa Pro Gly Ser Ile Ala Ala Leu
            20                  25                  30

Asp Val Lys Ala Cys Glu Gly Leu Ile Arg His Gly Ala Glu Val His
        35                  40                  45

Ala Val Met Ser Glu Ala Ala Thr Lys Ile Ile His Pro Tyr Ala Trp
    50                  55                  60

Asn Leu Pro Thr Gly Asn Pro Val Ile Thr Glu Ile Thr Gly Phe Ile
65                  70                  75                  80

Glu His Val Glu Leu Ala Gly Glu His Glu Asn Lys Ala Asp Leu Ile
                85                  90                  95

Leu Val Cys Pro Ala Thr Ala Asn Thr Ile Ser Lys Ile Ala Cys Gly
            100                 105                 110

Ile Asp Asp Thr Pro Val Thr Thr Val Val Thr Thr Ala Phe Pro His
        115                 120                 125

Ile Pro Ile Met Ile Ala Pro Ala Met His Glu Thr Met Tyr Arg His
    130                 135                 140

Pro Ile Val Arg Glu Asn Ile Glu Arg Leu Lys Lys Leu Gly Val Glu
145                 150                 155                 160

Phe Ile Gly Pro Arg Ile Glu Glu Gly Arg Ala Lys Val Ala Ser Ile
                165                 170                 175

Asp Glu Ile Val Tyr Arg Val Ile Lys Lys Leu His Lys Lys Thr Leu
            180                 185                 190

Glu Gly Lys Arg Val Leu Val Thr Ala Gly Ala Thr Arg Glu Tyr Ile
        195                 200                 205

Asp Pro Ile Arg Phe Ile Thr Asn Ala Ser Ser Gly Lys Met Gly Val
    210                 215                 220

Ala Leu Ala Glu Glu Ala Asp Phe Arg Gly Ala Val Thr Leu Ile Arg
225                 230                 235                 240

Thr Lys Gly Ser Val Lys Ala Phe Arg Ile Arg Lys Ile Lys Leu Lys
                245                 250                 255

Val Glu Thr Val Glu Glu Met Leu Ser Ala Ile Glu Asn Glu Leu Arg
            260                 265                 270
```

-continued

```
Ser Lys Lys Tyr Asp Val Val Ile Met Ala Ala Ala Val Ser Asp Phe
        275                 280                 285

Arg Pro Lys Ile Lys Ala Glu Gly Lys Ile Lys Ser Gly Arg Ser Ile
    290                 295                 300

Thr Ile Glu Leu Val Pro Xaa Asn Pro Lys Ile Ile Asp Arg Ile Lys
305                 310                 315                 320

Glu Ile Gln Pro Asn Val Phe Leu Val Gly Phe Lys Ala Glu Thr Ser
                325                 330                 335

Lys Glu Lys Leu Ile Glu Glu Gly Lys Arg Gln Ile Glu Arg Ala Lys
            340                 345                 350

Ala Asp Leu Val Val Gly Asn Thr Leu Glu Ala Phe Gly Ser Glu Glu
        355                 360                 365

Asn Gln Val Val Leu Ile Gly Arg Asp Phe Thr Lys Glu Leu Pro Lys
    370                 375                 380

Met Lys Lys Arg Glu Leu Ala Glu Arg Ile Trp Asp Glu Ile Glu Lys
385                 390                 395                 400

Xaa Leu Ser
```

(2) INFORMATION FOR SEQ ID NO:20:

(i) SEQUENCE CHARACTERISTICS:
(A) LENGTH: 33 base pairs
(B) TYPE: nucleic acid
(C) STRANDEDNESS: single
(D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:20:

CATAGCGAAT TCGCAAAACC TTTCGCGGTA TGG 33

(2) INFORMATION FOR SEQ ID NO:21:

(i) SEQUENCE CHARACTERISTICS:
(A) LENGTH: 33 base pairs
(B) TYPE: nucleic acid
(C) STRANDEDNESS: single
(D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:21:

ACTACGGAAT TCCACGGAAA ATGCCGCTCA TCC 33

(2) INFORMATION FOR SEQ ID NO:22:

(i) SEQUENCE CHARACTERISTICS:
(A) LENGTH: 20 base pairs
(B) TYPE: nucleic acid
(C) STRANDEDNESS: single
(D) TOPOLOGY: unknown (ii) MOLECULE TYPE: DNA (genomic)

(iii) HYPOTHETICAL: NO (iv) ANTI-SENSE: NO

-continued (xi) SEQUENCE DESCRIPTION: SEQ ID NO:22:

GGCGTTTCCG TTCTTCTTCG 20

(2) INFORMATION FOR SEQ ID NO:23:

(i) SEQUENCE CHARACTERISTICS:
(A) LENGTH: 20 base pairs
(B) TYPE: nucleic acid
(C) STRANDEDNESS: single
(D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:23:

CCATCTCACG CGCCAGTTTC 20

(2) INFORMATION FOR SEQ ID NO:24:

(i) SEQUENCE CHARACTERISTICS:
(A) LENGTH: 23 base pairs
(B) TYPE: nucleic acid
(C) STRANDEDNESS: single
(D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:24:

GAGGAGAGCA GGAAAGGTGG AAC 23

(2) INFORMATION FOR SEQ ID NO:25:

(i) SEQUENCE CHARACTERISTICS:
(A) LENGTH: 21 base pairs
(B) TYPE: nucleic acid
(C) STRANDEDNESS: single
(D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:25:

GCTGGGAGAA GACTTCACTG G 21

(2) INFORMATION FOR SEQ ID NO:26:

(i) SEQUENCE CHARACTERISTICS:
(A) LENGTH: 19 base pairs
(B) TYPE: nucleic acid
(C) STRANDEDNESS: single
(D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:26:

-continued

GAGCTTGCTC AACTTTATC 19

(2) INFORMATION FOR SEQ ID NO:27:

(i) SEQUENCE CHARACTERISTICS:
(A) LENGTH: 23 base pairs
(B) TYPE: nucleic acid
(C) STRANDEDNESS: single
(D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:27:

GATAGAGATA GTTTCTGGAG ACG 23

(2) INFORMATION FOR SEQ ID NO:28:

(i) SEQUENCE CHARACTERISTICS:
(A) LENGTH: 23 base pairs
(B) TYPE: nucleic acid
(C) STRANDEDNESS: single
(D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:28:

CGGGATATCG ACATTTCTGC ACC 23

(2) INFORMATION FOR SEQ ID NO:29:

(i) SEQUENCE CHARACTERISTICS:
(A) LENGTH: 24 base pairs
(B) TYPE: nucleic acid
(C) STRANDEDNESS: single
(D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:29:

GAGTTAAATG CCTACACTGT ATCT 24

(2) INFORMATION FOR SEQ ID NO:30:

(i) SEQUENCE CHARACTERISTICS:
(A) LENGTH: 24 base pairs
(B) TYPE: nucleic acid
(C) STRANDEDNESS: single
(D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:30:

CAGGACTCAG AAGCTGCTAT CGAA 24

-continued (2) INFORMATION FOR SEQ ID NO:31:

(i) SEQUENCE CHARACTERISTICS:
(A) LENGTH: 24 base pairs
(B) TYPE: nucleic acid
(C) STRANDEDNESS: single
(D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:31:

CTGCACGTGC CCTGTAGGAT TTGT 24

(2) INFORMATION FOR SEQ ID NO:32:

(i) SEQUENCE CHARACTERISTICS:
(A) LENGTH: 23 base pairs
(B) TYPE: nucleic acid
(C) STRANDEDNESS: single
(D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:32:

CCAGAYTGGA ARWKNAGGAA AGA 23

(2) INFORMATION FOR SEQ ID NO:33:

(i) SEQUENCE CHARACTERISTICS:
(A) LENGTH: 23 base pairs
(B) TYPE: nucleic acid
(C) STRANDEDNESS: single
(D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:33:

CCAGAYTGGA ARWKNAGAAA AGA 23

(2) INFORMATION FOR SEQ ID NO:34:

(i) SEQUENCE CHARACTERISTICS:
(A) LENGTH: 23 base pairs
(B) TYPE: nucleic acid
(C) STRANDEDNESS: single
(D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:34:

CCAGAYTGGA ARWKNAGGAA GGA 23

(2) INFORMATION FOR SEQ ID NO:35:

(i) SEQUENCE CHARACTERISTICS:

-continued (A) LENGTH: 23 base pairs
(B) TYPE: nucleic acid
(C) STRANDEDNESS: single
(D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:35:

CCAGAYTGGA ARWKNAGAAA GGA 23

(2) INFORMATION FOR SEQ ID NO:36:

(i) SEQUENCE CHARACTERISTICS:
(A) LENGTH: 84 base pairs
(B) TYPE: nucleic acid
(C) STRANDEDNESS: single
(D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:36:

CAGAGTGGGC AGAGAGGCTN TTGTTAAGGG GAAATTAATC GACGTGGAAA AGGAAGGAAA 60

AGTCGNTATT CCTCCAAGGG AATA 84

(2) INFORMATION FOR SEQ ID NO:37:

(i) SEQUENCE CHARACTERISTICS:
(A) LENGTH: 27 amino acids
(B) TYPE: amino acid
(D) TOPOLOGY: unknown (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:37:

```
Glu Trp Ala Glu Arg Leu Leu Leu Arg Gly Asn Xaa Ser Lys Trp Lys
1               5                   10                  15

Arg Lys Glu Lys Ser Xaa Phe Leu Gln Gly Asn
            20                  25
```

(2) INFORMATION FOR SEQ ID NO:38:

(i) SEQUENCE CHARACTERISTICS:
(A) LENGTH: 27 amino acids
(B) TYPE: amino acid
(D) TOPOLOGY: unknown (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:38:

Arg Val Gly Arg Glu Ala Xaa Val Lys Gly Lys Leu Ile Glu Val Glu

-continued

```
1               5                   10                  15

Lys Glu Gly Lys Val Xaa Ile Pro Pro Arg Glu
            20                  25
```

(2) INFORMATION FOR SEQ ID NO:39:

(i) SEQUENCE CHARACTERISTICS:
(A) LENGTH: 28 amino acids
(B) TYPE: amino acid
(D) TOPOLOGY: unknown (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:39:

```
Gln Ser Gly Gln Arg Gly Xaa Cys Xaa Gly Glu Ile Asn Arg Ser Gly
1               5                   10                  15

Lys Gly Arg Lys Ser Arg Tyr Ser Ser Lys Gly Leu
            20                  25
```

(2) INFORMATION FOR SEQ ID NO:40:

(i) SEQUENCE CHARACTERISTICS:
(A) LENGTH: 129 base pairs
(B) TYPE: nucleic acid
(C) STRANDEDNESS: single
(D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:40:

```
CTGCCCACTC TGAGGTCATA ACCTGCTGGT TGGAGCCATT CTTCAGAAAA TGGCTCTATA     60

AGTATTTCTT TTCTGATTTT CCAGTCTGGA AGTAGCATTT TACCACCGAA ACCTTTATTT    120

TTAATTTAA                                                            129
```

(2) INFORMATION FOR SEQ ID NO:41:

(i) SEQUENCE CHARACTERISTICS:
(A) LENGTH: 42 amino acids
(B) TYPE: amino acid
(D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:41:

```
Xaa Ile Lys Asn Lys Gly Phe Gly Gly Lys Met Leu Leu Pro Asp Trp
1               5                   10                  15

Lys Ile Arg Lys Glu Ile Leu Ile Glu Pro Phe Ser Glu Glu Trp Leu
            20                  25                  30

Gln Pro Ala Gly Tyr Asp Leu Arg Val Gly
        35                  40
```

-continued (2) INFORMATION FOR SEQ ID NO:42:

(i) SEQUENCE CHARACTERISTICS:
(A) LENGTH: 740 base pairs
(B) TYPE: nucleic acid
(C) STRANDEDNESS: single
(D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:42:

```
TCCTCCAAGG GAATACGCCT TAATCCTAAC CCTCGAGAGG ATAAAGTTGC CCGACGATGT     60

TATGGGGGAT ATGAAGATAA GGAGCAGTTT AGCAAGAGAA GGGGTTATTG GTTCTTTTGC    120

TTGGGTTGAC CCAGGATGGG ATGGAAACTT AACACTAATG CTCTACAATG CCTCAAATGA    180

ACCTGTCGAA TTAAGATATG GAGAGAGATT TGTGCAGATC GCATTTATAA GGCTAGAGGG    240

TCCGGCAAGA AACCCTTACA GAGGAAACTA TCAGGGGAGC ACAAGGTTAG CGTTTTCAAA    300

GAGAAAGAAA CTCTAGCGTC TTTTCAATAG CATCCTCAAT ATCTCGTGTG AAGTAATCAA    360

TGTAAATACT TGCTGGGTGG GTTTTTAGGG ATTCAAACTC GTAAGATGGG CCTGTATAGC    420

AGAAAACTAT TTTTGCCTCT TCTTCATTTA TCTTTCTGTG AATAAAAAAT CCAACATCCA    480

CACTAGTTCC AAAAGATATT GTTTGCGTGA TTACCAACAA GATCTTGGCA TTATTTTTGA    540

TCTTATACTC TATTCTCCTT TCTCCCTCCA ATTTGCCCAA AATAAACCTG GGTAGTATAC    600

ATTCACTCCT CTCTTTTAAA TTCCTATAAA TTCGTACATA GTTTAGAAAA ATGTCAAATT    660

CTTTNTTCCC TGTTAAATTA ACCNCNAAAT CTTTATNANN AANCTTTTTA TAATTCCCAA    720

AACCCCTAAT TTTCCCCTTN                                                740
```

(2) INFORMATION FOR SEQ ID NO:43:

(i) SEQUENCE CHARACTERISTICS:
(A) LENGTH: 246 amino acids
(B) TYPE: amino acid
(C) STRANDEDNESS: unknown
(D) TOPOLOGY: unknown (ii) MOLECULE TYPE: peptide (iii) HYPOTHETICAL: YES (iv) ANTI-SENSE: NO (v) FRAGMENT TYPE: N-terminal (xi) SEQUENCE DESCRIPTION: SEQ ID NO:43:

```
Leu Gln Gly Asn Thr Pro Xaa Ser Xaa Pro Ser Arg Gly Xaa Ser Cys
1               5                   10                  15

Pro Thr Met Leu Trp Gly Ile Xaa Arg Xaa Gly Ala Val Xaa Gln Glu
            20                  25                  30

Lys Gly Leu Leu Val Leu Leu Leu Gly Leu Thr Gln Asp Gly Met Glu
        35                  40                  45

Thr Xaa His Xaa Cys Ser Thr Met Pro Gln Met Asn Leu Ser Asn Xaa
    50                  55                  60

Asp Met Glu Arg Asp Leu Cys Arg Ser His Leu Xaa Gly Xaa Arg Val
65                  70                  75                  80

Arg Gln Glu Thr Leu Thr Glu Glu Thr Ile Arg Gly Ala Gln Gly Xaa
                85                  90                  95
```

-continued

Arg Phe Gln Arg Glu Arg Asn Ser Ser Val Phe Ser Ile Ala Ser Ser
100 105 110

Ile Ser Arg Val Lys Xaa Ser Met Xaa Ile Leu Ala Gly Trp Val Phe
115 120 125

Arg Asp Ser Asn Ser Xaa Asp Gly Pro Val Xaa Gln Lys Thr Ile Phe
130 135 140

Ala Ser Ser Ser Phe Ile Phe Leu Xaa Ile Lys Asn Pro Thr Ser Thr
145 150 155 160

Leu Val Pro Lys Asp Ile Val Cys Val Ile Thr Asn Lys Ile Leu Ala
165 170 175

Leu Phe Leu Ile Leu Tyr Ser Ile Leu Leu Ser Pro Ser Asn Leu Pro
180 185 190

Lys Ile Asn Leu Gly Ser Ile His Ser Leu Leu Ser Phe Lys Phe Leu
195 200 205

Xaa Ile Arg Thr Xaa Phe Arg Lys Met Ser Asn Ser Xaa Phe Pro Val
210 215 220

Lys Leu Thr Xaa Lys Ser Leu Xaa Xaa Xaa Phe Leu Xaa Phe Pro Lys
225 230 235 240

Pro Leu Ile Phe Pro Xaa
245

(2) INFORMATION FOR SEQ ID NO:44:

(i) SEQUENCE CHARACTERISTICS:
(A) LENGTH: 246 amino acids
(B) TYPE: amino acid
(D) TOPOLOGY: unknown (ii) MOLECULE TYPE: peptide (iii) HYPOTHETICAL: YES (xi) SEQUENCE DESCRIPTION: SEQ ID NO:44:

Pro Pro Arg Glu Tyr Ala Leu Ile Leu Thr Leu Glu Arg Ile Lys Leu
1 5 10 15

Pro Asn Asn Val Met Gly Asp Met Lys Ile Arg Ser Ser Leu Ala Arg
20 25 30

Glu Gly Val Ile Gly Ser Phe Ala Trp Val Asp Pro Gly Trp Asp Gly
35 40 45

Asn Leu Thr Leu Met Leu Tyr Asn Ala Ser Asn Glu Pro Val Glu Leu
50 55 60

Arg Tyr Gly Glu Arg Phe Val Gln Ile Ala Phe Ile Arg Leu Glu Gly
65 70 75 80

Pro Ala Arg Asn Pro Tyr Arg Gly Asn Tyr Gln Gly Ser Thr Arg Leu
85 90 95

Ala Phe Ser Lys Arg Lys Lys Leu Xaa Arg Leu Phe Asn Ser Ile Leu
100 105 110

Asn Ile Ser Cys Glu Val Ile Asn Val Asn Thr Cys Trp Val Gly Phe
115 120 125

Xaa Gly Phe Lys Leu Val Arg Trp Ala Cys Ile Ala Glu Asn Tyr Phe
130 135 140

Cys Leu Phe Phe Ile Tyr Leu Ser Val Asn Lys Lys Ser Asn Ile His
145 150 155 160

Thr Ser Ser Lys Arg Tyr Cys Leu Arg Asp Tyr Gln Gln Asp Leu Gly
165 170 175

Ile Ile Phe Asp Leu Ile Leu Tyr Ser Pro Phe Ser Leu Gln Phe Ala

-continued

```
        180                 185                 190

Gln Asn Lys Pro Gly Xaa Tyr Thr Phe Thr Pro Leu Phe Xaa Ile Pro
        195                 200                 205

Ile Asn Ser Tyr Ile Val Xaa Lys Asn Val Lys Phe Phe Xaa Pro Cys
    210                 215                 220

Xaa Ile Asn Xaa Xaa Ile Phe Xaa Xaa Xaa Leu Phe Ile Ile Pro Lys
225                 230                 235                 240

Thr Pro Asn Phe Pro Leu
                245
```

(2) INFORMATION FOR SEQ ID NO:45:

(i) SEQUENCE CHARACTERISTICS:
(A) LENGTH: 246 amino acids
(B) TYPE: amino acid
(D) TOPOLOGY: unknown (ii) MOLECULE TYPE: peptide (iii) HYPOTHETICAL: YES (xi) SEQUENCE DESCRIPTION: SEQ ID NO:45:

```
Ser Ser Lys Gly Ile Arg Leu Asn Pro Asn Pro Arg Glu Asp Lys Val
1               5                   10                  15

Ala Arg Arg Cys Tyr Gly Gly Tyr Glu Asp Lys Glu Gln Phe Ser Lys
            20                  25                  30

Arg Arg Gly Tyr Trp Phe Phe Cys Leu Gly Xaa Pro Arg Met Gly Trp
        35                  40                  45

Lys Leu Asn Thr Asn Ala Leu Gln Cys Leu Lys Xaa Thr Cys Arg Ile
    50                  55                  60

Lys Ile Trp Arg Glu Ile Cys Ala Asp Arg Ile Tyr Lys Ala Arg Gly
65                  70                  75                  80

Ser Gly Lys Lys Pro Leu Gln Arg Lys Leu Ser Gly Glu His Lys Val
                85                  90                  95

Ser Val Phe Lys Glu Lys Glu Thr Leu Ala Ser Phe Gln Xaa His Pro
            100                 105                 110

Gln Tyr Leu Val Xaa Ser Asn Gln Cys Lys Tyr Leu Leu Gly Gly Phe
        115                 120                 125

Leu Gly Ile Gln Thr Arg Lys Met Gly Leu Tyr Ser Arg Lys Leu Phe
    130                 135                 140

Leu Pro Leu Leu His Leu Ser Phe Cys Glu Xaa Lys Ile Gln His Pro
145                 150                 155                 160

His Xaa Phe Gln Lys Ile Leu Phe Ala Xaa Leu Pro Thr Arg Ser Trp
                165                 170                 175

His Tyr Phe Xaa Ser Tyr Thr Leu Phe Ser Phe Leu Pro Pro Ile Cys
            180                 185                 190

Pro Lys Xaa Thr Trp Val Val Tyr Ile His Ser Ser Leu Leu Asn Ser
        195                 200                 205

Tyr Lys Phe Val His Ser Leu Glu Lys Cys Gln Ile Leu Xaa Ser Leu
    210                 215                 220

Leu Asn Xaa Pro Xaa Asn Leu Tyr Xaa Xaa Xaa Phe Tyr Asn Ser Gln
225                 230                 235                 240

Asn Pro Xaa Phe Ser Pro
                245
```

(2) INFORMATION FOR SEQ ID NO:46:

-continued (i) SEQUENCE CHARACTERISTICS:
(A) LENGTH: 31 amino acids
(B) TYPE: amino acid
(C) STRANDEDNESS: unknown
(D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:46:

```
Met Leu His His Val Lys Leu Ile Tyr Ala Thr Lys Ser Arg Lys Leu
1               5                   10                  15

Val Gly Lys Lys Ile Val Xaa Xaa Xaa Pro Gly Ser Ile Ala Ala
            20                  25                  30
```

(2) INFORMATION FOR SEQ ID NO:47:

(i) SEQUENCE CHARACTERISTICS:
(A) LENGTH: 17 amino acids
(B) TYPE: amino acid
(C) STRANDEDNESS: unknown
(D) TOPOLOGY: unknown (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:47:

```
Lys Tyr Asp Val Val Ile Met Ala Ala Ala Val Ser Asp Phe Arg Phe
1               5                   10                  15

Lys
```

(2) INFORMATION FOR SEQ ID NO:48:

(i) SEQUENCE CHARACTERISTICS:
(A) LENGTH: 24 amino acids
(B) TYPE: amino acid
(C) STRANDEDNESS: unknown
(D) TOPOLOGY: unknown (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:48:

```
Ala Asp Leu Val Val Gly Asn Thr Leu Glu Ala Phe Gly Ser Glu Glu
1               5                   10                  15

Asn Gln Val Val Leu Ile Gly Arg
            20
```

(2) INFORMATION FOR SEQ ID NO:49:

(i) SEQUENCE CHARACTERISTICS:
(A) LENGTH: 21 base pairs
(B) TYPE: nucleic acid
(C) STRANDEDNESS: single
(D) TOPOLOGY: unknown -continued (ii) MOLECULE TYPE: DNA (genomic)

(iii) HYPOTHETICAL: NO (iv) ANTI-SENSE: NO (xi) SEQUENCE DESCRIPTION: SEQ ID NO:49:

CTATTGAGTA CGAACGCCAT C 21

(2) INFORMATION FOR SEQ ID NO:50:

(i) SEQUENCE CHARACTERISTICS:
(A) LENGTH: 20 base pairs
(B) TYPE: nucleic acid
(C) STRANDEDNESS: single
(D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:50:

GTCACGCTTG CTCCACTCCG 20

(2) INFORMATION FOR SEQ ID NO:51:

(i) SEQUENCE CHARACTERISTICS:
(A) LENGTH: 437 amino acids
(B) TYPE: amino acid
(D) TOPOLOGY: unknown (ii) MOLECULE TYPE: protein (iii) HYPOTHETICAL: NO (iv) ANTI-SENSE: NO (vi) ORIGINAL SOURCE:
(A) ORGANISM: Methanococcus Jannaschii (xi) SEQUENCE DESCRIPTION: SEQ ID NO:51:

```
Met Ile Ser Glu Ile Met His Pro Thr Lys Leu Leu Lys Gly Thr Lys
1               5                   10                  15

Ser Lys Leu Leu Glu Asn Lys Lys Ile Leu Val Ala Val Thr Ser Ser
            20                  25                  30

Ile Ala Ala Ile Glu Thr Pro Lys Leu Met Arg Glu Leu Ile Arg His
        35                  40                  45

Gly Ala Glu Val Tyr Cys Ile Ile Thr Glu Glu Thr Lys Lys Ile Ile
    50                  55                  60

Gly Lys Glu Ala Leu Lys Phe Gly Cys Gly Asn Glu Val Tyr Glu Glu
65                  70                  75                  80

Ile Thr Gly Xaa Xaa Xaa Xaa Xaa Asp Ile Glu His Ile Leu Leu Tyr
                85                  90                  95

Xaa Xaa Xaa Xaa Asn Glu Cys Asp Cys Leu Leu Ile Tyr Pro Ala Thr
            100                 105                 110

Ala Asn Ile Ile Ser Lys Ile Asn Leu Gly Ile Ala Asp Asn Ile Val
        115                 120                 125

Asn Thr Thr Ala Leu Met Phe Phe Gly Asn Lys Pro Ile Phe Ile Val
    130                 135                 140

Pro Ala Met His Glu Asn Met Phe Asn Xaa Xaa Ala Ile Lys Arg His
145                 150                 155                 160
```

-continued

```
Ile Asp Lys Leu Lys Glu Lys Asp Lys Ile Tyr Ile Ile Ser Pro Lys
                165                 170                 175

Phe Glu Glu Xaa Xaa Xaa Xaa Xaa Xaa Gly Lys Ala Lys Val Ala Asn
            180                 185                 190

Ile Glu Asp Val Val Lys Ala Val Ile Glu Lys Ile Gly Asn Asn Leu
        195                 200                 205

Lys Lys Glu Gly Asn Arg Val Leu Ile Leu Asn Gly Gly Thr Val Glu
    210                 215                 220

Phe Ile Asp Lys Val Arg Val Ile Ser Asn Leu Ser Ser Gly Lys Met
225                 230                 235                 240

Gly Val Ala Leu Ala Glu Ala Phe Cys Lys Glu Gly Phe Tyr Val Glu
                245                 250                 255

Val Ile Thr Ala Met Gly Leu Glu Pro Pro Tyr Tyr Ile Lys Asn His
            260                 265                 270

Lys Val Leu Thr Ala Lys Glu Met Leu Asn Lys Ala Ile Glu Xaa Xaa
        275                 280                 285

Leu Xaa Ala Lys Asp Phe Asp Ile Ile Ile Ser Ser Ala Ala Ile Ser
    290                 295                 300

Asp Phe Thr Val Glu Ser Xaa Phe Glu Gly Lys Leu Ser Ser Glu Glu
305                 310                 315                 320

Glu Xaa Xaa Xaa Xaa Leu Ile Leu Lys Leu Lys Arg Xaa Asn Pro Lys
                325                 330                 335

Val Leu Glu Glu Leu Arg Arg Ile Tyr Lys Asp Xaa Lys Val Ile Ile
            340                 345                 350

Gly Phe Lys Ala Glu Tyr Asn Leu Asp Glu Lys Glu Leu Ile Asn Arg
        355                 360                 365

Ala Lys Glu Arg Leu Asn Lys Tyr Asn Leu Asn Met Ile Ile Ala Asn
    370                 375                 380

Asp Leu Ser Lys Xaa Xaa His Tyr Phe Gly Asp Asp Tyr Ile Glu Val
385                 390                 395                 400

Tyr Ile Ile Thr Lys Tyr Glu Val Glu Lys Ile Ser Gly Ser Lys Lys
                405                 410                 415

Xaa Glu Ile Ser Glu Arg Ile Val Glu Lys Val Lys Lys Leu Val Lys
            420                 425                 430

Ser Xaa Xaa Xaa Xaa
        435
```

(2) INFORMATION FOR SEQ ID NO:52:

(i) SEQUENCE CHARACTERISTICS:
(A) LENGTH: 444 amino acids
(B) TYPE: amino acid
(D) TOPOLOGY: unknown (ii) MOLECULE TYPE: protein (iii) HYPOTHETICAL: NO (iv) ANTI-SENSE: NO (vi) ORIGINAL SOURCE:
(A) ORGANISM: Escherichia coli (xi) SEQUENCE DESCRIPTION: SEQ ID NO:52:

```
Met Lys Ala Arg Gln Gln Lys Tyr Cys Asp Lys Ile Ala Asn Phe Trp
1               5                   10                  15

Cys His Pro Thr Gly Lys Ile Ile Met Ser Leu Ala Gly Lys Lys Ile
            20                  25                  30
```

-continued

```
Val Leu Gly Val Ser Gly Gly Ile Ala Ala Tyr Lys Thr Pro Glu Leu
        35                  40                  45

Val Arg Arg Leu Arg Asp Arg Gly Ala Asp Val Arg Val Ala Met Thr
    50                  55                  60

Glu Ala Ala Lys Ala Phe Ile Thr Pro Leu Ser Leu Gln Ala Val Ser
65                  70                  75                  80

Gly Tyr Pro Val Ser Asp Ser Leu Leu Asp Pro Ala Ala Glu Ala Ala
                85                  90                  95

Met Gly His Ile Glu Leu Gly Xaa Xaa Xaa Xaa Lys Trp Ala Asp Leu
            100                 105                 110

Val Ile Leu Ala Pro Ala Thr Ala Asp Leu Ile Ala Arg Val Ala Ala
        115                 120                 125

Gly Met Ala Asn Asp Leu Val Ser Thr Ile Cys Leu Ala Thr Pro Xaa
    130                 135                 140

Xaa Ala Pro Val Ala Val Leu Pro Ala Met Asn Gln Gln Met Tyr Arg
145                 150                 155                 160

Ala Ala Ala Thr Gln His Asn Leu Glu Val Leu Ala Xaa Ser Arg Gly
                165                 170                 175

Leu Leu Ile Trp Gly Pro Asp Ser Gly Ser Gln Ala Cys Gly Asp Ile
            180                 185                 190

Gly Pro Gly Arg Xaa Xaa Asp Pro Leu Thr Ile Val Asp Met Ala Val
        195                 200                 205

Ala His Phe Ser Pro Val Asn Asp Leu Lys His Leu Asn Ile Met Ile
    210                 215                 220

Thr Ala Gly Pro Thr Arg Glu Pro Leu Asp Pro Val Arg Tyr Ile Ser
225                 230                 235                 240

Asn His Ser Ser Gly Lys Met Gly Phe Ala Ile Ala Ala Ala Ala Ala
                245                 250                 255

Arg Arg Gly Ala Asn Val Thr Leu Val Ser Gly Pro Val Ser Leu Pro
            260                 265                 270

Thr Pro Pro Phe Val Lys Arg Val Asp Val Met Thr Ala Leu Glu Met
        275                 280                 285

Glu Ala Ala Val Asn Xaa Xaa Ala Ser Val Gln Gln Gln Asn Ile Phe
    290                 295                 300

Ile Gly Cys Ala Ala Val Ala Asp Tyr Arg Ala Ala Thr Val Ala Pro
305                 310                 315                 320

Glu Lys Ile Lys Lys Gln Ala Thr Gln Gly Asp Glu Leu Thr Ile Lys
                325                 330                 335

Met Val Lys Xaa Asn Pro Asp Ile Val Ala Gly Val Ala Ala Leu Lys
            340                 345                 350

Asp His Arg Pro Tyr Val Val Gly Phe Ala Ala Glu Thr Asn Asn Xaa
        355                 360                 365

Xaa Xaa Xaa Val Glu Glu Tyr Ala Arg Gln Lys Arg Ile Arg Lys Asn
    370                 375                 380

Leu Asp Leu Ile Cys Ala Asn Asp Val Ser Gln Pro Thr Gln Gly Phe
385                 390                 395                 400

Asn Ser Asp Asn Asn Ala Leu His Leu Phe Trp Gln Asp Gly Asp Lys
                405                 410                 415

Val Leu Pro Leu Glu Arg Lys Glu Leu Leu Gly Gln Leu Leu Leu Asp
            420                 425                 430

Glu Ile Val Thr Arg Tyr Asp Glu Lys Asn Arg Arg
        435                 440
```

-continued (2) INFORMATION FOR SEQ ID NO:53:

(i) SEQUENCE CHARACTERISTICS:
(A) LENGTH: 14 amino acids
(B) TYPE: amino acid
(D) TOPOLOGY: unknown (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:53:

```
Xaa Gly Xaa Xaa Asp Xaa Xaa Xaa Xaa Gly Xaa Xaa Xaa Xaa
1               5                   10
```

(2) INFORMATION FOR SEQ ID NO:54:

(i) SEQUENCE CHARACTERISTICS:
(A) LENGTH: 14 amino acids
(B) TYPE: amino acid
(D) TOPOLOGY: unknown (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:54:

```
Phe Ala Trp Val Asp Pro Gly Trp Asp Gly Asn Thr Leu Met
1               5                   10
```

(2) INFORMATION FOR SEQ ID NO:55:

(i) SEQUENCE CHARACTERISTICS:
(A) LENGTH: 14 amino acids
(B) TYPE: amino acid
(D) TOPOLOGY: unknown (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:55:

```
Ala Gly Trp Ile Asp Ala Gly Phe Lys Gly Lys Ile Thr Leu
1               5                   10
```

(2) INFORMATION FOR SEQ ID NO:56:

(i) SEQUENCE CHARACTERISTICS:
(A) LENGTH: 14 amino acids
(B) TYPE: amino acid
(D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:56:

```
Ser Ala Val His Asp Pro Gly Tyr Glu Gly Arg Pro Glu Tyr
```

-continued

```
1               5                   10

(2) INFORMATION FOR SEQ ID NO:57:

     (i) SEQUENCE CHARACTERISTICS:
          (A) LENGTH: 14 amino acids
          (B) TYPE: amino acid
          (D) TOPOLOGY: unknown

    (ii) MOLECULE TYPE: peptide

   (iii) HYPOTHETICAL: NO

    (iv) ANTI-SENSE: NO

    (xi) SEQUENCE DESCRIPTION: SEQ ID NO:57:

Pro Thr Ile Val Asp Ala Gly Phe Glu Gly Gln Leu Thr Ile
1               5                   10

(2) INFORMATION FOR SEQ ID NO:58:

     (i) SEQUENCE CHARACTERISTICS:
          (A) LENGTH: 14 amino acids
          (B) TYPE: amino acid
          (D) TOPOLOGY: unknown

    (ii) MOLECULE TYPE: peptide

   (iii) HYPOTHETICAL: NO

    (iv) ANTI-SENSE: NO

    (xi) SEQUENCE DESCRIPTION: SEQ ID NO:58:

Ala His Arg Ile Asp Pro Gly Trp Ser Gly Cys Ile Val Leu
1               5                   10

(2) INFORMATION FOR SEQ ID NO:59:

     (i) SEQUENCE CHARACTERISTICS:
          (A) LENGTH: 24 base pairs
          (B) TYPE: nucleic acid
          (C) STRANDEDNESS: single
          (D) TOPOLOGY: unknown

    (ii) MOLECULE TYPE: DNA (genomic)

   (iii) HYPOTHETICAL: NO

    (iv) ANTI-SENSE: YES

    (xi) SEQUENCE DESCRIPTION: SEQ ID NO:59:

GAGTTAAATG CCTACACTGT ATCT                                            24

(2) INFORMATION FOR SEQ ID NO:60:

     (i) SEQUENCE CHARACTERISTICS:
          (A) LENGTH: 24 base pairs
          (B) TYPE: nucleic acid
          (C) STRANDEDNESS: single
          (D) TOPOLOGY: unknown

    (ii) MOLECULE TYPE: DNA (genomic)

   (iii) HYPOTHETICAL: NO

    (iv) ANTI-SENSE: NO

    (xi) SEQUENCE DESCRIPTION: SEQ ID NO:60:

CAGGACTCAG AAGCTGCTAT CGAA                                            24
```

-continued

```
(2) INFORMATION FOR SEQ ID NO:61:

     (i) SEQUENCE CHARACTERISTICS:
          (A) LENGTH: 24 base pairs
          (B) TYPE: nucleic acid
          (C) STRANDEDNESS: single
          (D) TOPOLOGY: unknown

    (ii) MOLECULE TYPE: DNA (genomic)

   (iii) HYPOTHETICAL: NO

    (iv) ANTI-SENSE: NO

    (xi) SEQUENCE DESCRIPTION: SEQ ID NO:61:

CTGCACGTGC CCTGTAGGAT TTGT                                         24
```